US009493472B2

(12) United States Patent
Allerheiligen et al.

(10) Patent No.: US 9,493,472 B2
(45) Date of Patent: Nov. 15, 2016

(54) SUBSTITUTED BENZOXAZOLES

(71) Applicant: BAYER PHARMA AKTIENGESELLSCHAFT, Berlin (DE)

(72) Inventors: Swen Allerheiligen, Essen (DE); Anja Buchmüller, Essen (DE); Karen Engel, Rossdorf (DE); Christoph Gerdes, Köln (DE); Kersten Matthias Gericke, Wuppertal (DE); Michael Gerisch, Wuppertal (DE); Stefan Heitmeier, Wülfrath (DE); Alexander Hillisch, Solingen (DE); Tom Kinzel, Düsseldorf (DE); Philip Lienau, Berlin (DE); Bernd Riedl, Wuppertal (DE); Susanne Röhrig, Hilden (DE); Martina Victoria Schmidt, Köln (DE); Julia Strassburger, Wuppertal (DE); Adrian Tersteegen, Wuppertal (DE)

(73) Assignee: Bayer Pharma Aktiengesellschaft, Berlin (DE)

( * ) Notice: Subject to any disclaimer, the term of this patent is extended or adjusted under 35 U.S.C. 154(b) by 0 days.

(21) Appl. No.: 14/895,793

(22) PCT Filed: May 30, 2014

(86) PCT No.: PCT/EP2014/061229
§ 371 (c)(1),
(2) Date: Dec. 3, 2015

(87) PCT Pub. No.: WO2014/195231
PCT Pub. Date: Dec. 11, 2014

(65) Prior Publication Data
US 2016/0137647 A1 May 19, 2016

(30) Foreign Application Priority Data
Jun. 3, 2013 (EP) .................... 13170208

(51) Int. Cl.
C07D 487/04 (2006.01)
A61K 31/4985 (2006.01)
A61K 31/495 (2006.01)
A61K 31/5386 (2006.01)
A61K 31/5377 (2006.01)
A61K 31/423 (2006.01)
A61K 31/454 (2006.01)
C07D 413/06 (2006.01)
C07D 263/58 (2006.01)
C07D 417/06 (2006.01)

(52) U.S. Cl.
CPC .......... C07D 487/04 (2013.01); A61K 31/423 (2013.01); A61K 31/454 (2013.01); A61K 31/495 (2013.01); A61K 31/4985 (2013.01); A61K 31/5377 (2013.01); A61K 31/5386 (2013.01); C07D 263/58 (2013.01); C07D 413/06 (2013.01); C07D 417/06 (2013.01)

(58) Field of Classification Search
None
See application file for complete search history.

(56) References Cited

U.S. PATENT DOCUMENTS

| 5,552,421 | A | 9/1996 | Lazer et al. |
| 6,710,055 | B2 | 3/2004 | Hauel et al. |
| 7,608,629 | B2 | 10/2009 | Blanco-Pillado et al. |
| 8,822,458 | B2 | 9/2014 | Straub et al. |
| 2003/0225131 | A1 | 12/2003 | Burgey et al. |
| 2006/0292073 | A1 | 12/2006 | Goodman et al. |

FOREIGN PATENT DOCUMENTS

| EP | 0535521 | 4/1993 |
| WO | 98/37075 | 8/1998 |
| WO | 01/47919 | 7/2001 |
| WO | 2004/094380 | 11/2004 |
| WO | 2007/140982 | 12/2007 |

OTHER PUBLICATIONS

International Search Report and Written Opinion mailed in PCT Application No. PCT/EP2014/061229, Jul. 7, 2014, 10 pages.
"Pschyrembel: Klinisches Worterbuch", 257.Auflage; Walter de Gruyter Verlag, Seite 610, Stichwort "Heparin", 1994, 2 pages.
"Stichwort "Heparin"", Rompp Lexikon Chemle—Version 1.5, Stuttgart/New York: Georg Thieme Verlag Stuttgart, 1998, 2 pages.
Ansell, et al., "Managing oral anticoagulant therapy", Chest, 119, 2001, pp. 22S-38S.
Artursson, et al., "Correlation between oral drug absorption in humans and apparent drug permeability coefficients in human intestinal epithelial (Caco-2) cells", Biochem. Biophys.175 (3), Mar. 29, 1991, pp. 880-885.
Berry, et al., "Antithrombotic actions of argatroban in rat models of venous, 'mixed' and arterial thrombosis, and its effects on the tail transection bleeding time", Br. J. Pharmacol. 113, 1994, pp. 1209-1214.
Braunwald (Editor), Eugene, "Heart Disease: a Textbook of Cardiovascular Medicine (5th edition)", 5. Auflage; W.B. Saunders Company, Philadelphia, 1997, 23 pages.
Casimiro-Garcia, et al., "Progress in the discovery of Factor Xa inhibitors", Expert Opin. Ther. Patents 16(2), 2006, pp. 119-145.
Chen, et al., "One-pot alpha-nucleophilic fluorination of acetophenones in a deep eutectic solvent", Journal of Fluorine Chemistry 131, 2010, pp. 340-344.
Feringa, et al., "1.4-Additions of Amines to 5-Methoxyfuran-Z(5H)-One: An Efficient Synthesis of Amino Diols", Heterocycles 27, No. 5, 1988, pp. 1197-1205.

(Continued)

Primary Examiner — Brian J Davis
(74) Attorney, Agent, or Firm — Aseem Mehta

(57) ABSTRACT

The invention relates to substituted benzoxazoles and to processes for their preparation and to their use for preparing medicaments for the treatment and/or prophylaxis of diseases, in particular of cardiovascular disorders, preferably of thrombotic or thromboembolic disorders.

17 Claims, No Drawings

(56) References Cited

OTHER PUBLICATIONS

Hirsh, Jack et al., "Oral Anticoagulants: Mechanism of Action, Clinical Effectiveness, and Optimal Therapeutic Range", Chest, 119, 1 (Supplement), Jan. 2001, pp. 8S-21S.

Horiuchi et al., "New Resolving Agents 2-Benzylamino Alcohols Synthesized from Natural Amino Acids", Agr. Biol. Chem. 37 (7), Feb. 12, 1973, pp. 1713-1716.

Kern, et al., "Drug Metabolism in Hepatocyte Sandwich Cultures of Rats and Humans", Biochemical Pharmacology, vol. 54,, 1997, pp. 761-772.

Lange, et al., "Asymmtric 1,4-Additions to 5-Alkoxy-2(5H)-Furanones Enantioselective Synthesis and Absolute Configuration Determination of beeta-Amino-g-Butyrolactones and Amino Diols", Tetrahedron vol. 45, No. 21, 1989, pp. 6799-6818.

Lok, et al., "Facile Rearrangements of Alkynylamino Heterocycles with Noble Metal Cations", J. Org. Chem. 61, 1996, pp. 3289-3297.

Oble, et al., "Carbonyl-Inserted Organo-Hybrids of a Dawson-Type Phosphovanadotungstate: Scope and Chemoselective Oxidation Catalysis", Org. Lett., vol. 13, No. 22,, 2011, pp. 5990-5993.

Ogura, et al., "A Versatile Synthesis of Four-, Five-, and Six-membered Cyclic Ketones Using Methyl Methylthiomethyl Sulfoxide", Bull. Chem. Soc. Jpn. 57, Jun. 1984, pp. 1637-1642.

Posakony, et al., "Fluoroamines via Chiral Cyclic Sulfamidates", Synthesis, No. 6, 2002, pp. 766-770.

Shoup, et al., "Synthesis of [F-18-]-1-Amino-3-Fluorocyclobutane-1- carboxylic Acid (FACBC): A Pet Tracer for Tumor Delineation", Labelled. Cpd. Radiopharm. 42, 1999, pp. 215-225.

Thvedt, et al., "Microwave assisted fluorination: an improved method for side chain fluorination of substituted 1-arylethanones", Tetrahedron 65 (46), 2009, pp. 9550-9556.

Wells, et al., "Interactions of Warfarin with Drugs and Food", Ann. Intern. Med., 121, 1994, pp. 676-683.

SUBSTITUTED BENZOXAZOLES

The invention relates to substituted benzoxazoles and to processes for their preparation and to their use for preparing medicaments for the treatment and/or prophylaxis of diseases, in particular of cardiovascular disorders, preferably of thrombotic or thromboembolic disorders.

Blood coagulation is a protective mechanism of the organism which helps to "seal" defects in the wall of the blood vessels quickly and reliably. Thus, loss of blood can be avoided or kept to a minimum. Haemostasis after injury of the blood vessels is effected mainly by the coagulation system in which an enzymatic cascade of complex reactions of plasma proteins is triggered. Numerous blood coagulation factors are involved in this process, each of which factors converts, on activation, the respectively next inactive precursor into its active form. At the end of the cascade comes the conversion of soluble fibrinogen into insoluble fibrin, resulting in the formation of a blood clot. In blood coagulation, traditionally the intrinsic and the extrinsic system, which end in a final joint reaction path, are distinguished. Here, factors Xa and IIa (thrombin) play key roles: Factor Xa bundles the signals of the two coagulation paths since it is formed both via factor VIIa/tissue factor (extrinsic path) and via the tenase complex (intrinsic path) by conversion of factor X. The activated serine protease Xa cleaves prothrombin to thrombin which, via a series of reactions, transduces the impulses from the cascade to the coagulation state of the blood: Thrombin directly cleaves fibrinogen to fibrin. It activates factor XIII, required for stabilization of the fibrin clot, to factor XIIIa. In addition, thrombin is a potent trigger of platelet aggregation (via PAR-1 activation), which also contributes considerably to haemostasis. By activating TAFI (thrombin-activatable fibrinolysis inhibitor) to TAFIa, thrombin in a complex with thrombomodulin inhibits the dissolution of the clot. Activation of factors V and VIII potentiates the production of thrombin and thus in turn amplifies the coagulation reaction.

In addition to unbound thrombin in the blood, bound forms are also known. During the formation of a fibrin clot, thrombin and prothrombinase (factor Xa in a complex) are bound to the fibrin skeleton. These enzyme molecules are still active and cannot be inhibited by endogenous antithrombin III. Thus, in this manner, clots still have a general coagulative potential.

In addition, thrombin, in particular via activation of PAR-1 receptors on endothelial cells, is also involved in inflammatory processes which, in interaction with the coagulation system, accelerates both processes.

Uncontrolled activation of the coagulation system or defect inhibition of the activation processes may lead to the formation of local thromboses or embolisms in vessels (arteries, veins, lymph vessels) or cardiac cavities. In addition, systemic hypercoagulability may lead to system-wide formation of thrombi and finally to consumption coagulopathy in the context of a disseminated intravasal coagulation. Thromboembolic complications are furthermore encountered in microangiopathic haemolytic anaemias, extracorporeal circulatory systems, such as haemodialysis, and also prosthetic heart valves and stents.

In the course of many cardiovascular and metabolic disorders, owing to systemic factors such as hyperlipidaemia, diabetes or smoking, owing to changes in blood flow with stasis, for example in atrial fibrillation, or owing to pathological changes in vessel walls, for example endothelial dysfunctions or atherosclerosis there is an increased tendency for coagulation and platelet activation which, via formation of fibrin- and platelet-rich thrombi, may lead to thromboembolic disorders and thrombotic complications with life-threatening conditions. Accordingly, thromboembolic disorders are the most frequent cause of morbidity and mortality in most industrialized countries [Heart Disease: A Textbook of Cardiovascular Medicine, Eugene Braunwald, 5. edition, 1997, W.B. Saunders Company, Philadelphia].

The anticoagulants known from the prior art, for example substances for inhibiting or preventing blood coagulation, have various disadvantages. In the therapy and prophylaxis of thromboembolic disorders, use is made, firstly, of heparin which is administered parenterally or subcutaneously. Because of more favourable pharmacokinetic properties, preference is these days increasingly given to low-molecular-weight heparin; however, the known disadvantages described hereinbelow encountered in heparin therapy cannot be avoided either in this manner. Thus, heparin is orally ineffective and has only a comparatively short half-life. In addition, there is a high risk of bleeding, there may in particular be cerebral haemorrhages and bleeding in the gastrointestinal tract, and there may be thrombopenia, alopecia medicomentosa or osteoporosis [Pschyrembel, Klinisches Wörterbuch [clinical dictionary], 257th edition, 1994, Walter de Gruyter Verlag, page 610, keyword "Heparin"; Römpp Lexikon Chemie, version 1.5, 1998, Georg Thieme Verlag Stuttgart, keyword "Heparin"]. Low-molecular-weight heparins do have a lower probability of leading to the development of heparin-induced thrombocytopenia; however, they can likewise only be administered subcutaneously. This also applies to fondaparinux, a synthetically produced selective factor Xa inhibitor having a long half-life.

A second class of anticoagulants are the vitamin K antagonists. These include, for example, 1,3-indanediones and in particular compounds such as warfarin, phenprocoumon, dicumarol and other cumarin derivatives which nonselectively inhibit the synthesis of various products of certain vitamin K-dependent coagulation factors in the liver. Owing to the mechanism of action, the onset of action is very slow (latency to the onset of action 36 to 48 hours). The compounds can be administered orally; however, owing to the high risk of bleeding and the narrow therapeutic index complicated individual adjustment and monitoring of the patient are required [J. Hirsh, J. Dalen, D. R. Anderson et al., "Oral anticoagulants: Mechanism of action, clinical effectiveness, and optimal therapeutic range" Chest 2001, 119, 8S-21S; J. Ansell, J. Hirsh, J. Dalen et al., "Managing oral anticoagulant therapy" Chest 2001, 119, 22S-38S; P. S. Wells, A. M. Holbrook, N. R. Crowther et al., "Interactions of warfarin with drugs and food" Ann. Intern. Med. 1994, 121, 676-683]. In addition, other side-effects such as gastrointestinal problems, hair loss and skin necroses have been described.

More recent approaches for oral anticoagulants are in various phases of clinical evaluation or in clinical use; however, they have also displayed disadvantages such as, for example, highly variable bioavailability, liver damage and bleeding complications, in particular in patients with damaged kidneys.

For antithrombotic medicaments, the therapeutic width is of importance: The distance between the therapeutically active dose for coagulation inhibition and the dose where bleeding may occur should be as big as possible so that maximum therapeutic activity is achieved at a minimum risk profile.

In particular under therapeutic conditions with thrombi already present, it may be advantageous to inhibit also the factor IIa present in the thrombus, and thereby promote a more rapid degradation of the thrombus. Using, for example, argatroban or hirudin as FIIa inhibitors, the advantageous effect of FIIa inhibition on an existing thrombus alone or in the presence of tissue plaminogen activator (tPA) has been demonstrated in various in-vitro and in-vivo models.

Accordingly, it is an object of the present invention to provide novel compounds as thrombin inhibitors for the treatment of cardiovascular disorders, in particular of thrombotic or thromboembolic disorders, in humans and animals, which compounds have a broad therapeutic width and good pharmacokinetic properties.

WO 98/37075 describes inter alia benzoxazole derivatives having an amidinobenzylamino substituent as thrombin inhibitors. Amidino-substituted thrombin inhibitors have a short half-life and low oral bioavailability. As such, the compounds are only suitable for parenteral administration and, when administered orally, have to be employed as prodrugs (A. Casimiro-Garcia, D. A. Dudley, R. J. Heemstra, K. J. Filipski, C. F. Bigge, J. J. Edmunds, *Expert Opin. Ther. Patents* 2006, 16(2), 119-145).

WO 2007/140982 describes the use of benzoxazoles as thrombin inhibitors.

EP-A 0 535 521 describes the use of benzoxazoles as leukotriene biosynthesis inhibitors for the treatment of inflammatory disorders.

The invention provides compounds of the formula

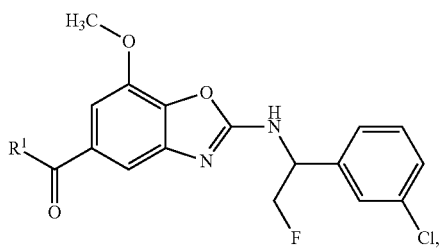

(I)

in which
R$^1$ represents a group of the formula

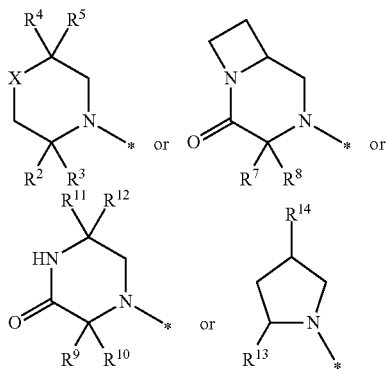

where * is the point of attachment to the carbonyl group,
X represents an oxygen atom, a sulphur atom or CH—R$^6$,
where
R$^6$ represents hydroxyl,
R$^2$ represents hydrogen, C$_1$-C$_6$-alkyl, C$_3$-C$_6$-cycloalkyl or phenyl, where alkyl and cycloalkyl may be substituted by a substituent selected from the group consisting of hydroxy, methoxy, cyano, hydroxycarbonyl, aminocarbonyl, methylsulphonyl, difluoromethoxy and trifluoromethoxy,
or
where alkyl and cycloalkyl may be substituted by 1 to 3 fluorine substituents,
R$^3$ represents hydrogen or C$_1$-C$_4$-alkyl,
or
R$^2$ and R$^3$ together with the carbon atom to which they are attached form a cyclopropyl ring, cyclobutyl ring or cyclopentyl ring,
where the cyclobutyl ring and the cyclopentyl ring may be substituted by a hydroxyl substituent,
R$^4$ represents hydrogen or C$_1$-C$_6$-alkyl,
where alkyl may be substituted by a hydroxyl substituent,
R$^5$ represents C$_1$-C$_4$-alkyl,
or
R$^4$ and R$^5$ together with the carbon atom to which they are attached form a cyclopropyl ring, cyclobutyl ring or cyclopentyl ring,
where the cyclobutyl ring and the cyclopentyl ring may be substituted by a hydroxyl substituent,
R$^7$ represents hydrogen or C$_1$-C$_6$-alkyl,
where alkyl may be substituted by a hydroxyl or cyano substituent,
or
where alkyl may be substituted by 1 to 3 fluorine substituents,
R$^8$ represents hydrogen,
R$^9$ represents hydrogen or C$_1$-C$_6$-alkyl,
where alkyl may be substituted by a hydroxyl or cyano substituent,
or
where alkyl may be substituted by 1 to 3 fluorine substituents,
R$^{10}$ represents hydrogen,
R$^{11}$ represents C$_1$-C$_4$-alkyl,
where alkyl may be substituted by a hydroxyl substituent,
R$^{12}$ represents hydrogen or C$_1$-C$_4$-alkyl,
or
R$^{11}$ and R$^{12}$ together with the carbon atom to which they are attached form a cyclopropyl ring, cyclobutyl ring or cyclopentyl ring,
where the cyclobutyl ring and the cyclopentyl ring may be substituted by a hydroxyl substituent,
R$^{13}$ represents hydroxymethyl or hydroxyethyl,
R$^{14}$ represents methoxy or ethoxy,
and the salts thereof, the solvates thereof and the solvates of the salts thereof.

Compounds according to the invention are the compounds of the formula (I) and the salts, solvates and solvates of the salts thereof, and also the compounds encompassed by formula (I) and specified hereinafter as working example(s), and the salts, solvates and solvates of the salts thereof, to the extent that the compounds encompassed by formula (I) and specified hereinafter are not already salts, solvates and solvates of the salts.

The compounds according to the invention may, depending on their structure, exist in different stereoisomeric forms, i.e. in the form of configurational isomers or else optionally as conformational isomers (enantiomers and/or diastereomers, including those in the case of atropisomers). The present invention therefore encompasses the enantiomers and diastereomers, and the respective mixtures thereof. The stereoisomerically uniform constituents can be isolated from such mixtures of enantiomers and/or diastereomers in a known manner; chromatography processes are preferably used for this, in particular HPLC chromatography on an achiral or chiral phase.

Where the compounds according to the invention can occur in tautomeric forms, the present invention encompasses all the tautomeric forms.

The present invention also encompasses all suitable isotopic variants of the compounds according to the invention. An isotopic variant of a compound according to the invention is understood here to mean a compound in which at least one atom within the compound according to the invention has been exchanged for another atom of the same atomic number, but with a different atomic mass than the atomic mass which usually or predominantly occurs in nature. Examples of isotopes which can be incorporated into a compound according to the invention are those of hydrogen, carbon, nitrogen, oxygen, phosphorus, sulphur, fluorine, chlorine, bromine and iodine, such as $^2$H (deuterium), $^3$H (tritium), $^{13}$C, $^{14}$C, $^{15}$N, $^{17}$O, $^{18}$O, $^{32}$P, $^{33}$P, $^{33}$S, $^{34}$S, $^{35}$S, $^{36}$S, $^{18}$F, $^{36}$Cl, $^{82}$Br, $^{123}$I, $^{124}$I, $^{129}$I, and $^{131}$I. Particular isotopic variants of a compound according to the invention, especially those in which one or more radioactive isotopes have been incorporated, may be beneficial, for example, for the examination of the mechanism of action or of the active ingredient distribution in the body; due to comparatively easy preparability and detectability, especially compounds labelled with $^3$H or $^{14}$C isotopes are suitable for this purpose. Furthermore, the incorporation of isotopes, for example of deuterium, can lead to particular therapeutic advantages as a consequence of greater metabolic stability of the compound, for example an extension of the half-life in the body or a reduction in the active dose required; such modifications of the compounds according to the invention may therefore, in some cases, also constitute a preferred embodiment of the present invention. Isotopic variants of the compounds according to the invention can be prepared by the processes known to those skilled in the art, for example by the methods described below and the procedures described in the working examples, by using corresponding isotopic modifications of the respective reagents and/or starting compounds.

In the context of the present invention, preferred salts are physiologically acceptable salts of the compounds according to the invention. Also included, however, are salts which are themselves unsuitable for pharmaceutical applications but can be used, for example, for the isolation or purification of the compounds according to the invention.

Physiologically acceptable salts of the compounds according to the invention include acid addition salts of mineral acids, carboxylic acids and sulphonic acids, for example salts of hydrochloric acid, hydrobromic acid, sulphuric acid, phosphoric acid, methanesulphonic acid, ethanesulphonic acid, toluenesulphonic acid, benzenesulphonic acid, naphthalenedisulphonic acid, acetic acid, trifluoroacetic acid, propionic acid, lactic acid, tartaric acid, malic acid, citric acid, fumaric acid, maleic acid and benzoic acid.

Physiologically acceptable salts of the compounds according to the invention also include salts of conventional bases, by way of example and with preference alkali metal salts (e.g. sodium and potassium salts), alkaline earth metal salts (e.g. calcium and magnesium salts) and ammonium salts derived from ammonia or organic amines having 1 to 16 carbon atoms, by way of example and with preference ethylamine, diethylamine, triethylamine, ethyldiisopropylamine, monoethanolamine, diethanolamine, triethanolamine, dicyclohexylamine, dimethylaminoethanol, procaine, dibenzylamine, N-methylmorpholine, arginine, lysine, ethylenediamine, N-methylpiperidine and choline.

In the context of the invention, solvates refer to those forms of the compounds according to the invention which, in the solid or liquid state, form a complex by coordination with solvent molecules. Hydrates are a specific form of solvates in which the coordination is with water.

Moreover, the present invention also encompasses prodrugs of the compounds according to the invention. The term "prodrugs" includes compounds which may themselves be biologically active or inactive but are converted to compounds according to the invention while resident in the body (for example metabolically or hydrolytically).

In the context of the present invention, the term "treatment" or "treating" includes inhibition, retardation, checking, alleviating, attenuating, restricting, reducing, suppressing, repelling or healing of a disease, a condition, a disorder, an injury or a health problem, or the development, the course or the progression of such states and/or the symptoms of such states. The term "therapy" is understood here to be synonymous with the term "treatment".

The terms "prevention", "prophylaxis" or "preclusion" are used synonymously in the context of the present invention and refer to the avoidance or reduction of the risk of contracting, experiencing, suffering from or having a disease, a condition, a disorder, an injury or a health problem, or a development or progression of such states and/or the symptoms of such states.

The treatment or prevention of a disease, a condition, a disorder, an injury or a health problem may be partial or complete.

In the context of the present invention, the substituents, unless specified otherwise, are each defined as follows:

Alkyl represents a straight-chain or branched alkyl radical having 1 to 6 carbon atoms, preferably 1 to 4 carbon atoms, by way of example and with preference methyl, ethyl, n-propyl, isopropyl, n-butyl, isobutyl, 1-methylpropyl, tert-butyl, n-pentyl, isopentyl, 1-ethylpropyl, 1-methylbutyl, 2-methylbutyl, 3-methylbutyl, n-hexyl, 1-methylpentyl, 2-methylpentyl, 3-methylpentyl, 4-methylpentyl, 3,3-dimethylbutyl, 1-ethylbutyl and 2-ethylbutyl.

Cycloalkyl represents a monocyclic cycloalkyl group having 3 to 6 carbon atoms, by way of example and with preference cyclopropyl, cyclobutyl, cyclopentyl and cyclohexyl may be mentioned for cycloalkyl.

In the formulae of the group which may represent $R^1$, the end point of the line marked by * does not represent a carbon atom or a $CH_2$ group, but is part of the bond to the atom to which $R^1$ is attached.

Preference is given to compounds of the formula (I) in which $R^1$ represents a group of the formula

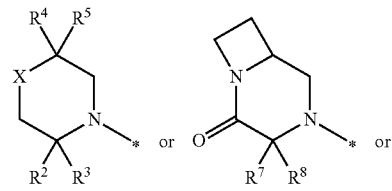

-continued

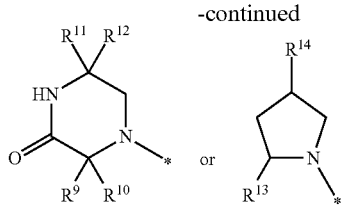

where * is the point of attachment to the carbonyl group,
X represents an oxygen atom or CH—$R^6$,
 where
  $R^6$ represents hydroxyl,
$R^2$ represents hydrogen, $C_1$-$C_4$-alkyl or $C_3$-$C_6$-cycloalkyl,
 where alkyl may be substituted by a hydroxyl or hydroxycarbonyl substituent,
 and
 where cycloalkyl may be substituted by a hydroxyl substituent,
$R^3$ represents hydrogen or $C_1$-$C_4$-alkyl,
or
$R^2$ and $R^3$ together with the carbon atom to which they are attached form a cyclobutyl ring,
 where the cyclobutyl ring may be substituted by a hydroxyl substituent,
$R^4$ represents hydrogen or $C_1$-$C_4$-alkyl,
 where alkyl may be substituted by a hydroxyl substituent,
$R^5$ represents $C_1$-$C_4$-alkyl,
$R^7$ represents hydrogen or $C_1$-$C_4$-alkyl,
$R^8$ represents hydrogen,
$R^9$ represents hydrogen or $C_1$-$C_4$-alkyl,
 where alkyl may be substituted by a hydroxyl substituent,
$R^{10}$ represents hydrogen,
$R^{11}$ and $R^{12}$ together with the carbon atom to which they are attached form a cyclopropyl ring,
$R^{13}$ represents hydroxymethyl or hydroxyethyl,
$R^{14}$ represents methoxy or ethoxy,
and the salts thereof, the solvates thereof and the solvates of the salts thereof.

Preference is also given to compounds of the formula (I) in which
$R^1$ represents a group of the formula

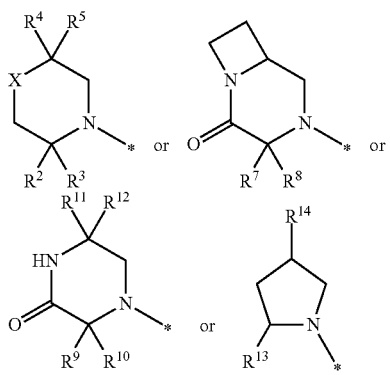

where * is the point of attachment to the carbonyl group,
X represents an oxygen atom,
$R^2$ represents methyl or ethyl,
 where methyl and ethyl are substituted by a hydroxyl substituent,
$R^3$ represents hydrogen,
or
$R^2$ and $R^3$ together with the carbon atom to which they are attached form a cyclopropyl ring,
 where the cyclobutyl ring is substituted by a hydroxyl substituent,
$R^4$ represents hydrogen or methyl,
$R^5$ represents methyl,
$R^7$ represents hydrogen or methyl,
$R^8$ represents hydrogen,
$R^9$ represents methyl,
$R^{10}$ represents hydrogen,
$R^{11}$ and $R^{12}$ together with the carbon atom to which they are attached form a cyclopropyl ring,
$R^{13}$ represents hydroxymethyl or hydroxyethyl,
$R^{14}$ represents ethoxy,
and the salts thereof, the solvates thereof and the solvates of the salts thereof.

Preference is also given to compounds of the formula (I) in which
$R^1$ represents a group of the formula

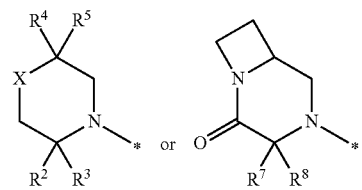

where * is the point of attachment to the carbonyl group,
X represents an oxygen atom, a sulphur atom or CH—$R^6$,
 where
  $R^6$ represents hydroxyl,
$R^2$ represents hydrogen, $C_1$-$C_6$-alkyl, $C_3$-$C_6$-cycloalkyl or phenyl,
 where alkyl and cycloalkyl may be substituted by a substituent selected from the group consisting of hydroxy, methoxy, cyano, hydroxycarbonyl, aminocarbonyl, methylsulphonyl, difluoromethoxy and trifluoromethoxy,
 or
 where alkyl and cycloalkyl may be substituted by 1 to 3 fluorine substituents,
$R^3$ represents hydrogen or $C_1$-$C_4$-alkyl,
or
$R^2$ and $R^3$ together with the carbon atom to which they are attached form a cyclopropyl ring, cyclobutyl ring or cyclopentyl ring,
 where the cyclobutyl ring and the cyclopentyl ring may be substituted by a hydroxyl substituent,
$R^4$ represents hydrogen or $C_1$-$C_6$-alkyl,
 where alkyl may be substituted by a hydroxyl substituent,
$R^5$ represents $C_1$-$C_4$-alkyl,
or
$R^4$ and $R^5$ together with the carbon atom to which they are attached form a cyclopropyl ring, cyclobutyl ring or cyclopentyl ring,
 where the cyclobutyl ring and the cyclopentyl ring may be substituted by a hydroxyl substituent, $R^7$ represents hydrogen or $C_1$-$C_6$-alkyl,
where alkyl may be substituted by a hydroxyl or cyano substituent,
or
where alkyl may be substituted by 1 to 3 fluorine substituents,
$R^8$ represents hydrogen,
and the salts thereof, the solvates thereof and the solvates of the salts thereof.

Preference is also given to compounds of the formula (I) in which
$R^1$ represents a group of the formula

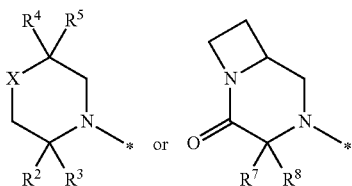

where * is the point of attachment to the carbonyl group,
X represents an oxygen atom or CH—$R^6$,
where
$R^6$ represents hydroxyl,
$R^2$ represents hydrogen, $C_1$-$C_4$-alkyl or $C_3$-$C_6$-cycloalkyl,
where alkyl may be substituted by a hydroxyl or hydroxycarbonyl substituent,
and
where cycloalkyl may be substituted by a hydroxyl substituent,
$R^3$ represents hydrogen or $C_1$-$C_4$-alkyl,
or
$R^2$ and $R^3$ together with the carbon atom to which they are attached form a cyclobutyl ring,
where the cyclobutyl ring may be substituted by a hydroxyl substituent,
$R^4$ represents hydrogen or $C_1$-$C_4$-alkyl,
where alkyl may be substituted by a hydroxyl substituent,
$R^5$ represents $C_1$-$C_4$-alkyl,
$R^7$ represents hydrogen or $C_1$-$C_4$-alkyl,
$R^8$ represents hydrogen,
and the salts thereof, the solvates thereof and the solvates of the salts thereof.

Preference is also given to compounds of the formula (I) in which
$R^1$ represents a group of the formula

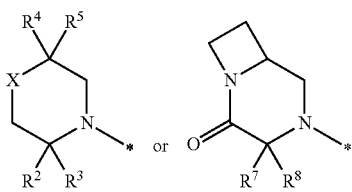

where * is the point of attachment to the carbonyl group,
X represents an oxygen atom or CH—$R^6$,
where
$R^6$ represents hydroxyl,
$R^2$ represents hydrogen, methyl, ethyl or cyclobutyl,
where methyl and ethyl may be substituted by a hydroxyl or hydroxycarbonyl substituent,
and
where cyclobutyl may be substituted by a hydroxyl substituent,
$R^3$ represents hydrogen or methyl,
or
$R^2$ and $R^3$ together with the carbon atom to which they are attached form a cyclobutyl ring,
where the cyclobutyl ring may be substituted by a hydroxyl substituent,
$R^4$ represents hydrogen, methyl, ethyl or propyl,
where methyl, ethyl and propyl may be substituted by a hydroxyl substituent,
$R^5$ represents methyl,
$R^7$ represents hydrogen, methyl or ethyl,
$R^8$ represents hydrogen,
and the salts thereof, the solvates thereof and the solvates of the salts thereof.

Preference is also given to compounds of the formula (I) in which
$R^1$ represents a group of the formula

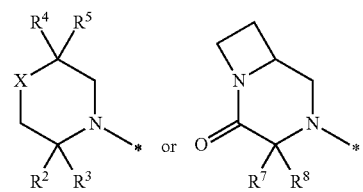

where * is the point of attachment to the carbonyl group,
X represents an oxygen atom,
$R^2$ represents methyl or ethyl,
where methyl and ethyl are substituted by a hydroxyl substituent,
$R^3$ represents hydrogen,
or
$R^2$ and $R^3$ together with the carbon atom to which they are attached form a cyclobutyl ring,
where the cyclobutyl ring is substituted by a hydroxyl substituent,
$R^4$ represents hydrogen or methyl,
$R^5$ represents methyl,
$R^7$ represents hydrogen or methyl,
$R^8$ represents hydrogen,
and the salts thereof, the solvates thereof and the solvates of the salts thereof.

Preference is also given to compounds of the formula (I) in which
$R^1$ represents a group of the formula

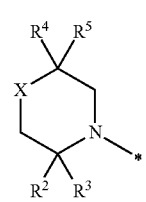

where * is the point of attachment to the carbonyl group,
X represents an oxygen atom, a sulphur atom or CH—$R^6$,
where
$R^6$ represents hydroxyl,
$R^2$ represents hydrogen, $C_1$-$C_6$-alkyl, $C_3$-$C_6$-cycloalkyl or phenyl, where alkyl and cycloalkyl may be substituted by a substituent selected from the group consisting of hydroxy, methoxy, cyano, hydroxycarbonyl, aminocarbonyl, methylsulphonyl, difluoromethoxy and trifluoromethoxy,
or
where alkyl and cycloalkyl may be substituted by 1 to 3 fluorine substituents,
$R^3$ represents hydrogen or $C_1$-$C_4$-alkyl,
or
$R^2$ and $R^3$ together with the carbon atom to which they are attached form a cyclopropyl ring, cyclobutyl ring or cyclopentyl ring,
where the cyclobutyl ring and the cyclopentyl ring may be substituted by a hydroxyl substituent,
$R^4$ represents hydrogen or $C_1$-$C_6$-alkyl,
where alkyl may be substituted by a hydroxyl substituent,
$R^5$ represents $C_1$-$C_4$-alkyl,
or
$R^4$ and $R^5$ together with the carbon atom to which they are attached form a cyclopropyl ring, cyclobutyl ring or cyclopentyl ring,
where the cyclobutyl ring and the cyclopentyl ring may be substituted by a hydroxyl substituent,
and the salts thereof, the solvates thereof and the solvates of the salts thereof.

Preference is also given to compounds of the formula (I) in which
$R^1$ represents a group of the formula

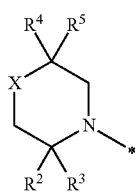

where * is the point of attachment to the carbonyl group,
X represents an oxygen atom or CH—$R^6$,
where
$R^6$ represents hydroxyl,
$R^2$ represents hydrogen, methyl, ethyl or cyclobutyl,
where methyl and ethyl may be substituted by a hydroxyl or hydroxycarbonyl substituent,
and
where cyclobutyl may be substituted by a hydroxyl substituent,
$R^3$ represents hydrogen or methyl,
or
$R^2$ and $R^3$ together with the carbon atom to which they are attached form a cyclobutyl ring,
where the cyclobutyl ring may be substituted by a hydroxyl substituent,
$R^4$ represents hydrogen, methyl, ethyl or propyl,
where methyl, ethyl and propyl may be substituted by a hydroxyl substituent,
$R^5$ represents methyl,
and the salts thereof, the solvates thereof and the solvates of the salts thereof.

Preference is also given to compounds of the formula (I) in which
$R^1$ represents a group of the formula

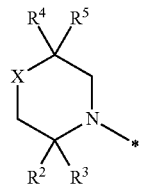

where * is the point of attachment to the carbonyl group,
X represents an oxygen atom,
$R^2$ represents methyl, ethyl or cyclobutyl,
where methyl and ethyl are substituted by a hydroxyl substituent,
and
where cyclobutyl is substituted by a hydroxyl substituent,
$R^3$ represents hydrogen,
$R^4$ represents hydrogen or methyl,
and
$R^5$ represents methyl,
or
$R^2$ represents methyl,
$R^3$ represents hydrogen or methyl,
$R^4$ represents methyl, ethyl or propyl,
where methyl, ethyl and propyl are substituted by a hydroxyl substituent,
and
$R^5$ represents methyl,
or
$R^2$ and $R^3$ together with the carbon atom to which they are attached form a cyclobutyl ring,
where the cyclobutyl ring is substituted by a hydroxyl substituent,
$R^4$ represents hydrogen or methyl,
and
$R^5$ represents methyl,
and the salts thereof, the solvates thereof and the solvates of the salts thereof.

Preference is also given to compounds of the formula (I) in which
$R^1$ represents a group of the formula

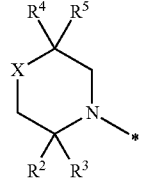

where * is the point of attachment to the carbonyl group,
X represents an oxygen atom,
$R^2$ represents methyl or ethyl,
where methyl and ethyl are substituted by a hydroxyl substituent,
$R^3$ represents hydrogen,
or
$R^2$ and $R^3$ together with the carbon atom to which they are attached form a cyclobutyl ring, where the cyclobutyl ring is substituted by a hydroxyl substituent,
$R^4$ represents hydrogen or methyl,
$R^5$ represents methyl,
and the salts thereof, the solvates thereof and the solvates of the salts thereof.

Preference is also given to compounds of the formula (I) in which
$R^1$ represents a group of the formula

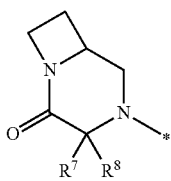

where * is the point of attachment to the carbonyl group,
$R^7$ represents hydrogen or $C_1$-$C_6$-alkyl,
where alkyl may be substituted by a hydroxyl or cyano substituent,
or
where alkyl may be substituted by 1 to 3 fluorine substituents,
$R^8$ represents hydrogen,
and the salts thereof, the solvates thereof and the solvates of the salts thereof.

Preference is also given to compounds of the formula (I) in which
$R^1$ represents a group of the formula

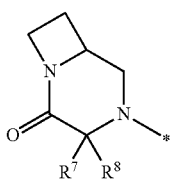

where * is the point of attachment to the carbonyl group,
$R^7$ represents hydrogen, methyl or ethyl,
$R^8$ represents hydrogen,
and the salts thereof, the solvates thereof and the solvates of the salts thereof.

Preference is also given to compounds of the formula (I) in which
$R^1$ represents a group of the formula

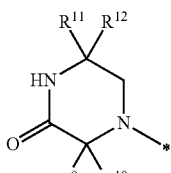

where * is the point of attachment to the carbonyl group,
$R^9$ represents hydrogen or $C_1$-$C_6$-alkyl,
where alkyl may be substituted by a hydroxyl or cyano substituent,
or
where alkyl may be substituted by 1 to 3 fluorine substituents, $R^{10}$ represents hydrogen,
$R^{11}$ represents $C_1$-$C_4$-alkyl,
where alkyl may be substituted by a hydroxyl substituent,
$R^{12}$ represents hydrogen or $C_1$-$C_4$-alkyl,
or
$R^{11}$ and $R^{12}$ together with the carbon atom to which they are attached form a cyclopropyl ring, cyclobutyl ring or cyclopentyl ring,
where the cyclobutyl ring and the cyclopentyl ring may be substituted by a hydroxyl substituent,
and the salts thereof, the solvates thereof and the solvates of the salts thereof.

Preference is also given to compounds of the formula (I) in which
$R^1$ represents a group of the formula

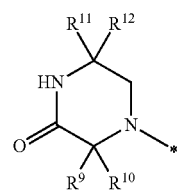

where * is the point of attachment to the carbonyl group,
$R^9$ represents methyl,
$R^{10}$ represents hydrogen,
$R^{11}$ and $R^{12}$ together with the carbon atom to which they are attached form a cyclopropyl ring,
and the salts thereof, the solvates thereof and the solvates of the salts thereof.

Preference is also given to compounds of the formula (I) in which
$R^1$ represents a group of the formula

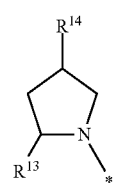

where * is the point of attachment to the carbonyl group,
$R^{13}$ represents hydroxymethyl or hydroxyethyl,
$R^{14}$ represents methoxy or ethoxy,
and the salts thereof, the solvates thereof and the solvates of the salts thereof.

Preference is also given to compounds of the formula (I) in which
$R^1$ represents a group of the formula

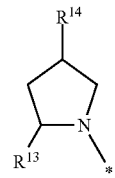

where * is the point of attachment to the carbonyl group,
$R^{13}$ represents hydroxymethyl or hydroxyethyl, $R^{14}$ represents ethoxy,
and the salts thereof, the solvates thereof and the solvates of the salts thereof.

Preference is also given to compounds of the formula (Ia)

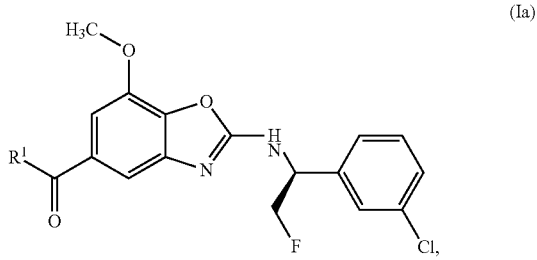

in which $R^1$ is as defined above.

Preference is also given to
(2-{[1-(3-chlorophenyl)-2-fluoroethyl]amino}-7-methoxy-1,3-benzoxazol-5-yl)[(5S)-5-(2-hydroxyethyl)-2-methylmorpholin-4-yl]methanone [enantiomerically pure isomer 2]
or
(2-{[1-(3-chlorophenyl)-2-fluoroethyl]amino}-7-methoxy-1,3-benzoxazol-5-yl)[5-(3-hydroxycyclobutyl)-2-methylmorpholin-4-yl]methanone [enantiomerically pure isomer 4]
or
(2-{[1-(3-chlorophenyl)-2-fluoroethyl]amino}-7-methoxy-1,3-benzoxazol-5-yl)(cis-2-hydroxy-7-methyl-8-oxa-5-azaspiro[3.5]non-5-yl)methanone [enantiomerically pure isomer 2]
or
4-[(2-{[1-(3-chlorophenyl)-2-fluorethyl]amino}-7-methoxy-1,3-benzoxazol-5-yl)carbonyl]-3-methyl-1,4-diazabicyclo[4.2.0]octan-2-one [enantiomerically pure isomer]
or
{(3S)-4-[(2-{[1-(3-chlorophenyl)-2-fluoroethyl]amino}-7-methoxy-1,3-benzoxazol-5-yl)carbonyl]-6-methylmorpholin-3-yl}acetic acid [enantiomerically pure isomer]
or
(2-{[1-(3-chlorophenyl)-2-fluoroethyl]amino}-7-methoxy-1,3-benzoxazol-5-yl)[(5R)-5-(2-hydroxyethyl)-2,2-dimethylmorpholin-4-yl]methanone [diastereomer mixture, 2 isomers]
or one of the salts, the solvates or the solvates of the salts of these compounds.

Particular preference is given to (2-{[1-(3-chlorophenyl)-2-fluoroethyl]amino}-7-methoxy-1,3-benzoxazol-5-yl)[(5S)-5-(2-hydroxyethyl)-2-methylmorpholin-4-yl]methanone [enantiomerically pure isomer 2] having the formula below

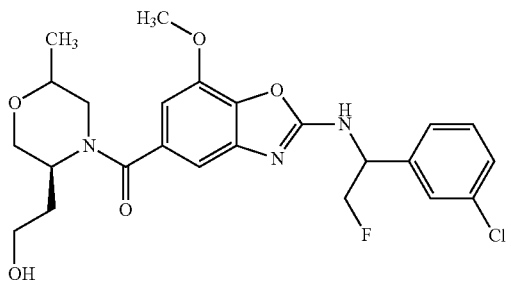 [SMILES: COc1cc(C(=O)N2CC(C)OC[C@@H]2CCO)cc2nc(NC(CF)c3cccc(Cl)c3)oc12]

or one of the salts thereof, solvates thereof or solvates of the salts thereof.

Particular preference is also given to (2-{[(1S)-1-(3-chlorophenyl)-2-fluoroethyl]amino}-7-methoxy-1,3-benzoxazol-5-yl)[(2S,5S)-5-(2-hydroxyethyl)-2-methylmorpholin-4-yl]methanone having the formula below

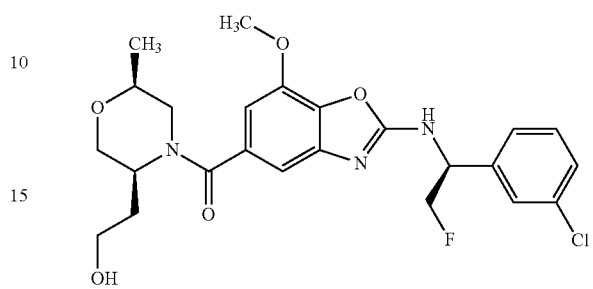

or one of the salts thereof, solvates thereof or solvates of the salts thereof.

The invention also provides the compound 2-(6-methylmorpholin-3-yl)ethanol [racemate] having the formula below

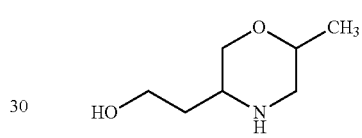

or one of the salts thereof, solvates thereof or solvates of the salts thereof.

The compound 2-(6-methylmorpholin-3-yl)ethanol [racemate] can be separated into its enantiomers by methods known to the person skilled in the art, for example by chromatography on a chiral phase.

Preference is also given to the compound 2-[(3S,6S)-6-methylmorpholin-3-yl]ethanol of the formula below

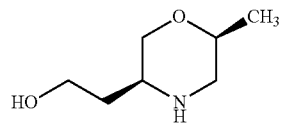

or one of the salts thereof, solvates thereof or solvates of the salts thereof.

The invention further provides a process for preparing the compounds of the formula (I), or the salts thereof, solvates thereof and the solvates of the salts thereof, wherein the compound of the formula

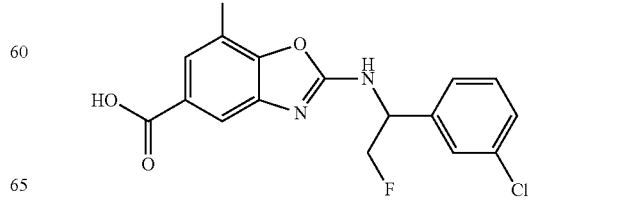

is reacted with compounds of the formula $$R^1\text{—}H \quad \text{(III)}$$

in which
R$^1$ has the meaning given above
with dehydrating agents.

The reaction is generally carried out in inert solvents, if appropriate in the presence of a base, preferably in a temperature range from 0° C. to room temperature at atmospheric pressure.

Suitable dehydrating agents here are, for example, carbodiimides such as N,N'-diethyl-, N,N'-dipropyl-, N,N'-diisopropyl-, N,N'-dicyclohexylcarbodiimide, N-(3-dimethylaminoisopropyl)-N'-ethylcarbodiimide hydrochloride (EDC) (optionally in the presence of pentafluorophenol (PFP)), N-cyclohexylcarbodiimid-N'-propyloxymethyl-polystyrene (PS-carbodiimide) or carbonyl compounds such as carbonyldiimidazole, or 1,2-oxazolium compounds such as 2-ethyl-5-phenyl-1,2-oxazolium 3-sulphate or 2-tert-butyl-5-methyl-isoxazolium perchlorate, or acylamino compounds such as 2-ethoxy-1-ethoxycarbonyl-1,2-dihydroquinoline, or propanephosphonic anhydride, or isobutyl chloroformate, or bis-(2-oxo-3-oxazolidinyl)phosphoryl chloride or benzotriazolyloxytri(dimethylamino)phosphonium hexafluorophosphate, or O-(benzotriazol-1-yl)-N,N,N',N'-tetramethyluronium hexafluorophosphate (HBTU), 2-(2-oxo-1-(2H)-pyridyl)-1,1,3,3-tetramethyluronium tetrafluoroborate (TPTU), (benzotriazol-1-yloxy)bisdimethylaminomethylium fluoroborate (TBTU) or O-(7-azabenzotriazol-1-yl)-N,N,N',N'-tetramethyluronium hexafluorophosphate (HATU), or 1-hydroxybenzotriazole (HOBt), or benzotriazol-1-yloxytris(dimethylamino)phosphonium hexafluorophosphate (BOP), or mixtures of these, with bases. The condensation is preferably carried out using HATU.

Bases are, for example, alkali metal carbonates such as sodium carbonate or potassium carbonate, or sodium bicarbonate or potassium bicarbonate, or organic bases such as trialkylamines, for example triethylamine, N-methylmorpholine, N-methylpiperidine, 4-dimethylaminopyridine or diisopropylethylamine; preference is given to diisopropylethylamine.

Inert solvents are, for example, halogenated hydrocarbons such as dichloromethane or trichloromethane, hydrocarbons such as benzene, or other solvents such as nitromethane, dioxane, dimethylformamide, dimethyl sulphoxide or acetonitrile, or mixtures of the solvents; preference is given to dimethylformamide.

The compounds of the formula (III) are known, can be synthesized from the corresponding starting compounds by known processes or can be prepared analogously to the processes described in the Examples section.

The compound of the formula (II) is known or can be prepared by reacting the compounds of the formula

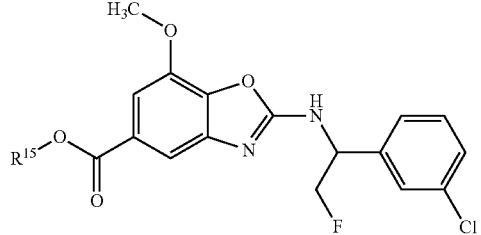

(IV)

in which
R$^{15}$ represents methyl or ethyl,
with a base.

The reaction is generally carried out in inert solvents, preferably in a temperature range of from 0° C. to room temperature at atmospheric pressure.

Bases are, for example, alkali metal hydroxides such as sodium hydroxide, lithium hydroxide or potassium hydroxide, or alkali metal carbonates such as caesium carbonate, sodium carbonate or potassium carbonate; preference is given to sodium hydroxide.

Inert solvents are, for example, halogenated hydrocarbons such as dichloromethane, trichloromethane, carbon tetrachloride, trichloroethane, tetrachloroethane, 1,2-dichloroethane or trichloroethylene, ethers such as diethyl ether, methyl tert-butyl ether, 1,2-dimethoxyethane, dioxane, tetrahydrofuran, glycol dimethyl ether or diethylene glycol dimethyl ether, alcohols such as methanol, ethanol, n-propanol, isopropanol, n-butanol or tert-butanol, hydrocarbons such as benzene, xylene, toluene, hexane, cyclohexane or mineral oil fractions, or other solvents such as dimethylformamide, dimethylacetamide, dimethyl sulphoxide, acetonitrile or pyridine, or mixtures of solvents; preference is given to dioxane.

The compounds of the formula (IV) are known or can be prepared by reacting compounds of the formula

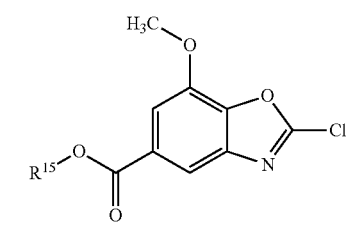

(V)

in which
R$^{15}$ represents methyl or ethyl,
with the compound of the formula

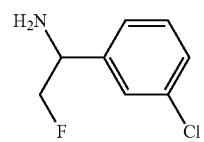

(VI)

in the presence of a base.

The reaction is generally carried out in inert solvents, preferably in a temperature range of from room temperature to reflux of the solvents at atmospheric pressure.

The compounds of the formulae (V) and (VI) are known, can be synthesized from the corresponding starting compounds by known processes or can be prepared analogously to the processes described in the Examples section.

The preparation of the starting compounds and of the compounds of the formula (I) can be illustrated by the synthesis scheme below.

Scheme 1:

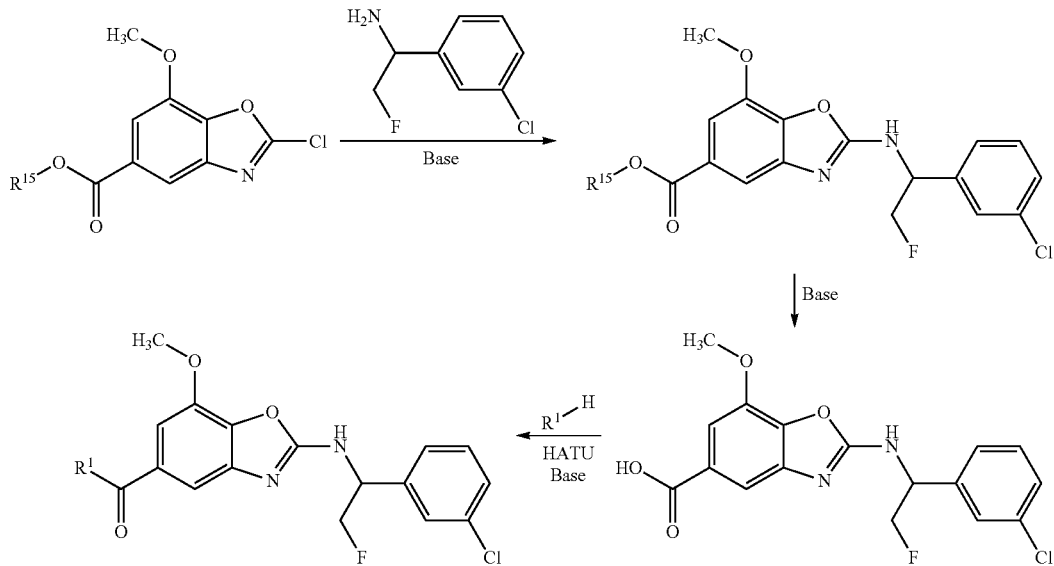

The compounds according to the invention have an unforeseeable useful spectrum of pharmacological activity and good pharmacokinetic properties. They are compounds modulating the proteolytic activity of the serine protease thrombin. The compounds according to the invention inhibit the thrombin-catalysed enzymatic cleavage of substrates which play an essential role in the activation of blood coagulation, platelet aggregation (via PAR-1 activation of the platelets) and thrombin-induced inflammation, fibrosis and angionesis processes.

They are therefore suitable for use as medicaments for the treatment and/or prophylaxis of diseases in humans and animals.

The present invention furthermore provides the use of the compounds according to the invention for the treatment and/or prophylaxis of disorders, in particular cardiovascular disorders, preferably thrombotic or thromboembolic disorders and/or thrombotic or thromboembolic complications.

As a key enzyme at the end of the coagulation cascade, thrombin translates, via a series of conversions, the impulses of the cascade into the coagulation state of the blood. By conversion of fibrinogen into insoluble fibrin, fibrin clots are formed, which are likewise stabilized by thrombin-activated factor XIIIa. By activating TAFI (thrombin-activatable fibrinolysis inhibitor) to TAFIa, thrombin in a complex with thrombomodulin inhibits the dissolution of the clot. Activation of factors V and VIII potentiates the production of thrombin and thus in turn amplifies the coagulation reaction. In addition, thrombin is a potent trigger of platelet aggregation (via PAR-1 activation), which also contributes considerably to haemostasis.

Accordingly, the compounds according to the invention are suitable for the treatment and/or prophylaxis of disorders or complications which arise or may arise from the formation of clots.

For the purpose of the present invention, the "thrombotic or thromboembolic disorders" include disorders which occur both in the arterial and in the venous vasculature and which can be treated with the compounds according to the invention, in particular disorders in the coronary arteries of the heart, such as acute coronary syndrome (ACS), myocardial infarction with ST segment elevation (STEMI) and without ST segment elevation (non-STEMI), stable angina pectoris, unstable angina pectoris, reocclusions and restenoses after coronary interventions such as angioplasty, stent implantation or aortocoronary bypass, but also thrombotic or thromboembolic disorders in further vessels leading to peripheral arterial occlusive disorders, pulmonary embolisms, venous thromboembolisms, venous thromboses, in particular in deep leg veins and kidney veins, transitory ischaemic attacks and also thrombotic stroke and thromboembolic stroke.

Stimulation of the coagulation system may occur by various causes or associated disorders. In the context of surgical interventions, immobility, confinement to bed, infection or cancer or cancer therapy, inter alia, the coagulation system can be highly activated, and there may be thrombotic complications, in particular venous thromboses. The compounds according to the invention are therefore suitable for the prophylaxis of thromboses in the context of surgical interventions in patients suffering from cancer. The compounds according to the invention are therefore also suitable for the prophylaxis of thromboses in patients having an activated coagulation system, for example in the stimulation situations described.

Accordingly, the compounds according to the invention are also suitable for the prevention and treatment of cardiogenic thromboembolisms such as, for example, brain ischaemias, stroke and systemic thromboembolisms and ischaemias, in patients with acute, intermittent or persistent cardiac arrhythmias such as, for example, atrial fibrillation, and those undergoing cardioversion, furthermore in patients with heart valve disorders or with artificial heart valves.

Thromboembolic complications are furthermore encountered in microangiopathic haemolytic anaemias, extracorporeal circulatory systems, such as haemodialysis, and also prosthetic heart valves.

Moreover, the compounds according to the invention are particularly suitable for the treatment of disorders where a clot is already present, since the thrombin incorporated in the clot stabilizes the clot. Since the inhibition of these thrombin molecules accelerates the degradation of the clot, the compounds according to the invention can be used for the treatment of existing clots. These clots may be formed in the entire vascular system and may cause grave complications in various organs, in particular via ischaemia, inflammatory reactions or formation of embolisms, for example myocardial infarction or stroke, but also pulmonary embolism or post-thrombotic syndrome in particular after deep vein thromboses in the leg. Accordingly, the compounds according to the invention are also suitable for the treatment of venous and arterial occlusions of the occular blood vessels caused by clots, for example age-related macular degeneration.

By virtue of the synergistic effects observed with lytic therapeutic principles such as the tissue plasminogen activator (tPA), the compounds are suitable for adjunctive use in the context of thrombolysis therapy.

Moreover, the compounds according to the invention are suitable for the treatment and/or prophylaxis of disorders involving microclot formation, for example fibrin deposits in cerebral blood vessels which may lead to dementia disorders such as vascular dementia or Alzheimer's disease. Here, the clot may contribute to the disorder both via occlusions and by binding further disease-relevant factors.

Moreover, the compounds according to the invention are suitable in particular for the treatment and/or prophylaxis of disorders where, in addition to the pro-coagulant component, the pro-inflammatory component of thrombin action plays an essential role. Mutual enhancement of coagulation and inflammation in particular can be prevented by the compounds according to the invention, thus decisively lowering the probability of thrombotic complications. Here, the treatment and/or prophylaxis in the context of atherosclerotic vascular disorders, inflammations in the context of rheumatic disorders of the locomotor system, inflammatory disorders of the lung, such as pulmonary fibroses, inflammatory disorders of the kidney, such as glomerulonephritides, inflammatory disorders of the intestine, such as Crohn's disease or ulcerative colitis, or disorders which may be present in the context of a diabetic underlying disease, such as diabetic retinopathy or nephropathy, may be considered, inter alia.

Moreover, the compounds according to the invention can be used for inhibiting tumour growth and the formation of metastases, and also for the prophylaxis and/or treatment of thromboembolic complications, such as, for example, venous thromboembolisms, for tumour patients, in particular those undergoing major surgical interventions or chemo- or radiotherapy.

Moreover, the compounds according to the invention are also suitable for the prophylaxis and/or treatment of pulmonary hypertension.

In the context of the present invention, the term "pulmonary hypertension" includes pulmonary arterial hypertension, pulmonary hypertension associated with disorders of the left heart, pulmonary hypertension associated with pulmonary disorders and/or hypoxia and pulmonary hypertension owing to chronic thromboembolisms (CTEPH).

"Pulmonary arterial hypertension" comprises idiopathic pulmonary arterial hypertension (IPAH, formerly also referred to as primary pulmonary hypertension), familial pulmonary arterial hypertension (FPAH) and associated pulmonary-arterial hypertension (APAH), which is associated with collagenoses, congenital systemic-pulmonary shunt vitia, portal hypertension, HIV infections, the ingestion of certain drugs and medicaments, with other disorders (thyroid disorders, glycogen storage disorders, Morbus Gaucher, hereditary teleangiectasia, haemoglobinopathies, myeloproliferative disorders, splenectomy), with disorders having a significant venous/capillary contribution, such as pulmonary-venoocclusive disorder and pulmonary-capillary haemangiomatosis, and also persisting pulmonary hypertension of neonatants.

Pulmonary hypertension associated with disorders of the left heart comprises a diseased left atrium or ventricle and mitral or aorta valve defects.

Pulmonary hyptertension associated with pulmonary disorders and/or hypoxia comprises chronic obstructive pulmonary disorders, interstitial pulmonary disorder, sleep apnoea syndrome, alveolar hypoventilation, chronic high-altitude sickness and inherent defects.

Pulmonary hypertension owing to chronic thromboembolisms (CTEPH) comprises the thromboembolic occlusion of proximal pulmonary arteries, the thromboembolic occlusion of distal pulmonary arteries and non-thrombotic pulmonary embolisms (tumour, parasites, foreign bodies).

The present invention furthermore provides the use of the compounds according to the invention for preparing medicaments for the treatment and/or prophylaxis of pulmonary hypertension associated with sarcoidosis, histiocytosis X and lymphangiomatosis.

Moreover, the substances according to the invention may also be suitable for treating pulmonary and hepatic fibroses.

Moreover, the compounds according to the invention may also be suitable for the treatment and/or prophylaxis of disseminated intravascular coagulation in the context of an infectious disease, and/or of systemic inflammatory syndrome (SIRS), septic organ dysfunction, septic organ failure and multiorgan failure, acute respiratory distress syndrome (ARDS), acute lung injury (ALI), septic shock and/or septic organ failure.

In the course of an infection, there may be a generalized activation of the coagulation system (disseminated intravascular coagulation or consumption coagulopathy, hereinbelow referred to as "DIC") with microthrombosis in various organs and secondary haemorrhagic complications. Moreover, there may be endothelial damage with increased permeability of the vessels and seeping of fluids and proteins into the extravasal lumen. As the infection progresses, there may be failure of an organ (for example kidney failure, liver failure, respiratory failure, central-nervous deficits and cardiovascular failure) or multiorgan failure.

In the case of DIC, there is a massive activation of the coagulation system at the surface of damaged endothelial cells, the surfaces of foreign bodies or injured extravascular tissue. As a consequence, there is coagulation in small vessels of various organs with hypoxia and subsequent organ dysfunction. A secondary effect is the consumption of coagulation factors (for example factor X, prothrombin and fibrinogen) and platelets, which reduces the coagulability of the blood and may result in heavy bleeding.

The compounds according to the invention are very particularly suitable for the treatment and/or prophylaxis of acute coronary syndrome (ACS), venous thromboembolisms, venous thromboses, in particular in deep leg veins and kidney veins, pulmonary embolisms, stroke and/or thrombosis prophylaxis in the context of surgical interventions, in particular in the context of surgical interventions in patients suffering from cancer.

The present invention further provides for the use of the compounds according to the invention for the treatment and/or prophylaxis of disorders, in particular the disorders mentioned above.

The present invention further provides for the use of the compounds according to the invention for producing a medicament for treatment and/or prophylaxis of disorders, in particular the disorders mentioned above.

The present invention further provides a method for the treatment and/or prophylaxis of disorders, especially the disorders mentioned above, using a therapeutically effective amount of a compound according to the invention.

The present invention further provides the compounds according to the invention for use in a method for the treatment and/or prophylaxis of disorders, especially the disorders mentioned above, using a therapeutically effective amount of a compound according to the invention.

The present invention further provides medicaments comprising a compound according to the invention and one or more further active compounds.

In addition, the compounds according to the invention can also be used for preventing coagulation ex vivo, for example for the protection of organs to be transplanted against organ damage caused by formation of clots and for protecting the organ recipient against thromboemboli from the transplanted organ, for preserving blood and plasma products, for cleaning/pretreating catheters and other medical auxiliaries and instruments, for coating synthetic surfaces of medical auxiliaries and instruments used in vivo or ex vivo or for biological samples which may comprise factor IIa.

The present invention further provides a method for preventing the coagulation of blood in vitro, in particular in banked blood or biological samples which may contain factor IIa, which method is characterized in that an anticoagulatory effective amount of the compound according to the invention is added.

The present invention further provides medicaments comprising a compound according to the invention and one or more further active compounds, especially for the treatment and/or prophylaxis of the disorders mentioned above. Preferred examples of active compounds suitable for combinations include:

- lipid-lowering substances, in particular HMG-CoA-(3-hydroxy-3-methylglutaryl-coenzyme A) reductase inhibitors such as, for example, lovastatin (Mevacor), simvastatin (Zocor), pravastatin (Pravachol), fluvastatin (Lescol) and atorvastatin (Lipitor);
- coronary therapeutics/vasodilatators, in particular ACE (angiotensin converting enzyme) inhibitors such as, for example, captopril, lisinopril, enalapril, ramipril, cilazapril, benazepril, fosinopril, quinapril and perindopril, or AII (angiotensin II) receptor antagonists such as, for example, embusartan, losartan, valsartan, irbesartan, candesartan, eprosartan and temisartan, or β-adrenoceptor antagonists such as, for example, carvedilol, alprenolol, bisoprolol, acebutolol, atenolol, betaxolol, carteolol, metoprolol, nadolol, penbutolol, pindolol, propanolol and timolol, or alpha-1-adrenoceptor antagonists such as, for example, prazosine, bunazosine, doxazosine and terazosine, or diuretics such as, for example, hydrochlorothiazide, furosemide, bumetanide, piretanide, torasemide, amiloride and dihydralazine, or calcium channel blockers such as, for example, verapamil and diltiazem, or dihydropyridine derivatives such as, for example, nifedipin (Adalat) and nitrendipine (Bayotensin), or nitro preparations such as, for example, isosorbide 5-mononitrate, isosorbide dinitrate and glycerol trinitrate, or substances causing an increase in cyclic guanosine monophosphate (cGMP) such as, for example, stimulators of soluble guanylate cyclase, for example riociguat;
- plasminogen activators (thrombolytics/fibrinolytics) and compounds which promote thrombolysis/fibrinolysis such as inhibitors of the plasminogen activator inhibitor (PAI inhibitors) or inhibitors of the thrombin-activated fibrinolysis inhibitor (TAFI inhibitors) such as, for example, tissue plasminogen activator (t-PA, for example Actilyse®), streptokinase, reteplase and urokinase;
- anticoagulatory substances (anticoagulants), such as, for example, heparin (UFH), low-molecular-weight heparins (NMH), such as, for example, tinzaparin, certoparin, parnaparin, nadroparin, ardeparin, enoxaparin, reviparin, dalteparin, danaparoid, semuloparin (AVE 5026), adomiparin (M118) and EP-42675/ORG42675;
- direct thrombin inhibitors (DTI) such as, for example, Pradaxa (dabigatran), atecegatran (AZD-0837), DP-4088, SSR-182289A, argatroban, bivalirudin and tanogitran (BIBT-986 and prodrug BIBT-1011), hirudin;
- direct factor Xa inhibitors such as, for example, rivaroxaban, apixaban, edoxaban (DU-176b), betrixaban (PRT-54021), R-1663, darexaban (YM-150), otamixaban (FXV-673/RPR-130673), letaxaban (TAK-442), razaxaban (DPC-906), DX-9065a, LY-517717, idraparinux and fondaparinux;
- platelet aggregation-inhibiting substances (platelet aggregation inhibitors, thrombocyte aggregation inhibitors) such as, for example, acetylsalicylic acid (for example Aspirin), ticlopidine (Ticlid), clopidogrel (Plavix), prasugrel, ticagrelor, cangrelor, elinogrel, vorapaxar;
- fibrinogen receptor antagonists (glycoprotein-IIb/IIIa antagonists) such as, for example, abciximab, eptifibatide, tirofiban, lamifiban, lefradafiban and fradafiban;
- recombinant human activated protein C such as, for example, Xigris;
- and also antiarrhythmics.

The present invention furthermore provides a combination comprising (A) a compound of the formula (I) and (B) 5-chloro-N-({(5S)-2-oxo-3-[4-(3-oxo-4-morpholinyl)-phenyl]-1,3-oxazolidin-5-yl}methyl)-2-thiophenecarboxamide (rivaroxaban) [WO 01/47919] having the structural formula

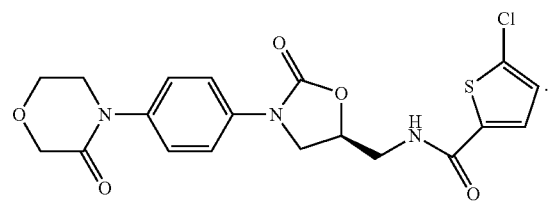 [SMILES: O=C(NC[C@H]1CN(c2ccc(N3CCOCC3=O)cc2)C(=O)O1)c1ccc(Cl)s1]

The present invention also provides a combination comprising (A) (2-{[1-(3-chlorophenyl)-2-fluoroethyl]amino}-7-methoxy-1,3-benzoxazol-5-yl)[(5S)-5-(2-hydroxyethyl)-2-methylmorpholin-4-yl]methanone [enantiomerically pure isomer 2] having the formula below

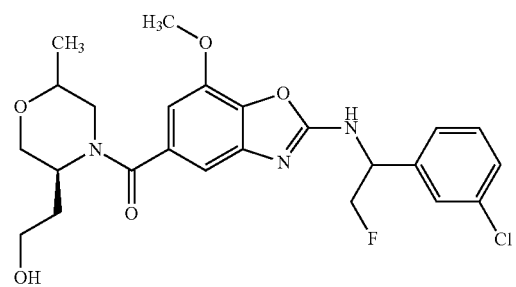 [SMILES: COc1cc(C(=O)N2CC(C)OC[C@@H]2CCO)cc2nc(NC(CF)c3cccc(Cl)c3)oc12]

or one of the salts thereof, solvates thereof or solvates of the salts thereof and (B) 5-chloro-N-({(5S)-2-oxo-3-[4-(3-oxo-4-morpholinyl)phenyl]-1,3-oxazolidin-5-yl}methyl)-2-thiophenecarboxamide (rivaroxaban) having the structural formula

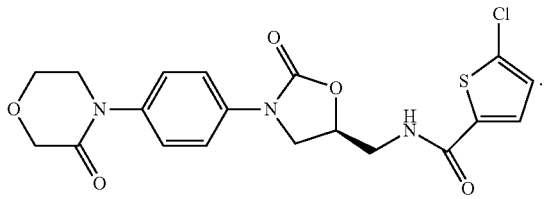 [SMILES: O=C(NC[C@H]1CN(c2ccc(N3CCOCC3=O)cc2)C(=O)O1)c1ccc(Cl)s1]

The present invention furthermore provides a combination comprising (A) (2-{[(1S)-1-(3-chlorophenyl)-2-fluoroethyl]amino}-7-methoxy-1,3-benzoxazol-5-yl)[(2S,5S)-5-(2-hydroxyethyl)-2-methylmorpholin-4-yl]methanone having the formula below

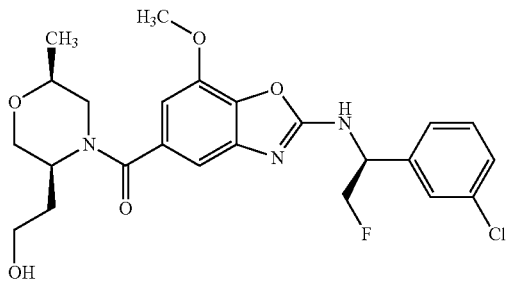 [SMILES: COc1cc(C(=O)N2C[C@H](C)OC[C@@H]2CCO)cc2nc(N[C@H](CF)c3cccc(Cl)c3)oc12]

or one of the salts thereof, solvates thereof or solvates of the salts thereof
and (B) 5-chloro-N-({(5S)-2-oxo-3-[4-(3-oxo-4-morpholinyl)phenyl]-1,3-oxazolidin-5-yl}methyl)-2-thiophenecarboxamide (rivaroxaban) having the structural formula

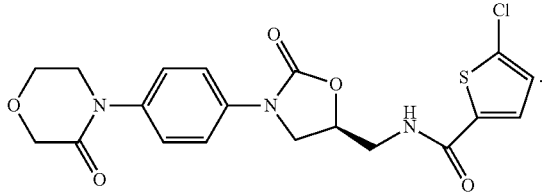

The present invention furthermore provides a combination comprising (A) (2-{[(1S)-1-(3-chlorophenyl)-2-fluoroethyl]amino}-7-methoxy-1,3-benzoxazol-5-yl)[(2S,5S)-5-(2-hydroxyethyl)-2-methylmorpholin-4-yl]methanone having the formula below

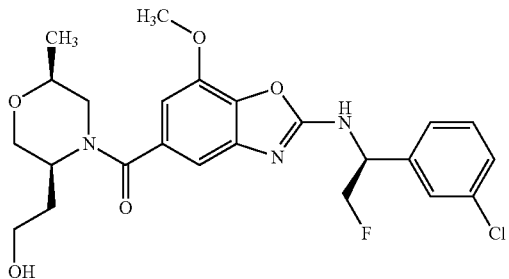 [SMILES: COc1cc(C(=O)N2C[C@H](C)OC[C@@H]2CCO)cc2nc(N[C@H](CF)c3cccc(Cl)c3)oc12]

and (B) 5-chloro-N-({(5S)-2-oxo-3-[4-(3-oxo-4-morpholinyl)phenyl]-1,3-oxazolidin-5-yl}methyl)-2-thiophenecarboxamide (rivaroxaban) having the structural formula

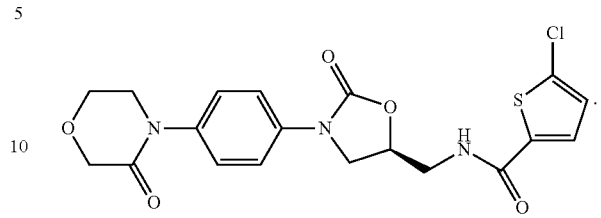

"Combinations" mean for the purpose of the invention not only dosage forms which contain all the components (so-called fixed combinations), and combination packs which contain the components separate from one another, but also components which are administered simultaneously or sequentially, as long as they are employed for the prophylaxis and/or treatment of the same disease. It is likewise possible to combine two or more active compounds with one another, i.e. they are in each case two-component or multi-component combinations.

In the combination, the active compounds (2-{[(1S)-1-(3-chlorophenyl)-2-fluoroethyl]amino}-7-methoxy-1,3-benzoxazol-5-yl)[(2S,5S)-5-(2-hydroxyethyl)-2-methylmorpholin-4-yl]methanone and 5-chloro-N-({(5S)-2-oxo-3-[4-(3-oxo-4-morpholinyl)phenyl]-1,3-oxazolidin-5-yl}methyl)-2-thiophenecarboxamide (rivaroxaban) are preferably each employed in a subtherapeutic amount.

In the combination, the active compounds (2-{[(1S)-1-(3-chlorophenyl)-2-fluoroethyl]amino}-7-methoxy-1,3-benzoxazol-5-yl)[(2S,5S)-5-(2-hydroxyethyl)-2-methylmorpholin-4-yl]methanone and 5-chloro-N-({(5S)-2-oxo-3-[4-(3-oxo-4-morpholinyl)phenyl]-1,3-oxazolidin-5-yl}methyl)-2-thiophenecarboxamide (rivaroxaban) are preferably each employed in a subtherapeutic amount, where the subtherapeutic amount refers to the disorders for which the combination is used.

Preferably, 20 mg to 120 mg of (2-{[(1S)-1-(3-chlorophenyl)-2-fluoroethyl]amino}-7-methoxy-1,3-benzoxazol-5-yl)[(2S,5S)-5-(2-hydroxyethyl)-2-methylmorpholin-4-yl] methanone are employed in the combination per 24-hour period, particularly preferably 20 mg to 80 mg per 24-hour period.

Preferably, 2.5 mg to 10 mg of 5-chloro-N-({(5S)-2-oxo-3-[4-(3-oxo-4-morpholinyl)phenyl]-1,3-oxazolidin-5-yl}methyl)-2-thiophenecarboxamide (rivaroxaban) are employed in the combination per 24-hour period, particularly preferably 2.5 mg, 5 mg or 10 mg per 24-hour period.

The compounds according to the invention may act systemically and/or locally. For this purpose, they can be administered in a suitable manner, for example by the oral, parenteral, pulmonal, nasal, sublingual, lingual, buccal, rectal, dermal, transdermal, conjunctival or otic route, or as an implant or stent.

The compounds according to the invention can be administered in administration forms suitable for these administration routes.

Suitable administration forms for oral administration are those which function according to the prior art and deliver the compounds according to the invention rapidly and/or in modified fashion, and which contain the compounds according to the invention in crystalline and/or amorphized and/or dissolved form, for example tablets (uncoated or coated tablets, for example having enteric coatings or coatings which are insoluble or dissolve with a delay and control the release of the compound according to the invention), tablets which disintegrate rapidly in the mouth, or films/wafers, films/lyophilizates, capsules (for example hard or soft gelatin capsules), sugar-coated tablets, granules, pellets, powders, emulsions, suspensions, aerosols or solutions.

Parenteral administration can bypass an absorption step (e.g. intravenously, intraarterially, intracardially, intraspinally or intralumbally) or include an absorption (e.g. intramuscularly, subcutaneously, intracutaneously, percutaneously or intraperitoneally). Suitable administration forms for parenteral administration include injection and infusion formulations in the form of solutions, suspensions, emulsions, lyophilizates or sterile powders.

Oral administration is preferred.

Suitable administration forms for the other administration routes are, for example, pharmaceutical forms for inhalation (including powder inhalers, nebulizers), nasal drops, solutions or sprays; tablets for lingual, sublingual or buccal administration, films/wafers or capsules, suppositories, preparations for the ears or eyes, vaginal capsules, aqueous suspensions (lotions, shaking mixtures), lipophilic suspensions, ointments, creams, transdermal therapeutic systems (for example patches), milk, pastes, foams, dusting powders, implants or stents.

The compounds according to the invention can be converted to the administration forms mentioned. This can be done in a manner known per se, by mixing with inert, nontoxic, pharmaceutically suitable excipients. These auxiliaries include carriers (for example microcrystalline cellulose, lactose, mannitol), solvents (e.g. liquid polyethylene glycols), emulsifiers and dispersing or wetting agents (for example sodium dodecylsulphate, polyoxysorbitan oleate), binders (for example polyvinylpyrrolidone), synthetic and natural polymers (for example albumin), stabilizers (e.g. antioxidants, for example ascorbic acid), dyes (e.g. inorganic pigments, for example iron oxides) and flavour and/or odour correctants.

The present invention further provides medicaments comprising at least one compound according to the invention, preferably together with one or more inert nontoxic pharmaceutically suitable excipients, and the use thereof for the purposes mentioned above.

In the case of parenteral administration, it has generally been found to be advantageous to administer amounts of about 5 to 250 mg every 24 hours to achieve effective results. In the case of oral administration, the amount is about 5 to 500 mg every 24 hours.

It may nevertheless be necessary where appropriate to deviate from the stated amounts, specifically as a function of the body weight, route of administration, individual response to the active compound, nature of the preparation and time or interval over which administration takes place.

The percentages in the tests and examples which follow are, unless indicated otherwise, percentages by weight; parts are parts by weight. Solvent ratios, dilution ratios and concentration figures for liquid/liquid solutions are each based on volume. "w/v" means "weight/volume". For example, "10% w/v" means: 100 ml of solution or suspension comprise 10 g of substance.

A) EXAMPLES

Abbreviations br. d. broad doublet (in NMR)
br. m. broad multiplet (in NMR)
br. s. broad singlet (in NMR)
d day(s), doublet (in NMR)
TLC thin-layer chromatography
dd doublet of doublets (in NMR)
DMSO dimethyl sulphoxide
dt doublet of triplets (in NMR)
ESI electrospray ionization (in MS)
GC-MS gas chromatography-coupled mass spectroscopy
h hour(s)
HATU O-(7-azabenzotriazol-1-yl)-N,N,N',N'-tetramethyluronium hexafluorophosphate
HPLC high-pressure, high-performance liquid chromatography
conc. concentrated
LC-MS liquid chromatography-coupled mass spectroscopy
m multiplet (in NMR)
M molar
$m_c$ centred multiplet (in NMR)
min minute(s)
MS mass spectroscopy
N normal
NMR nuclear magnetic resonance spectroscopy
quant. quantitative
Q quartet (in NMR)
quin quintet (in NMR)
RP reversed phase
RT room temperature (20-25° C.)
$R_t$ retention time (in HPLC)
s singlet (in NMR)
t triplet (in NMR)
UV ultraviolet
UPLC ultra high pressure, ultra high performance chromatography LC-MS Methods:

Method 1A:

Instrument: Waters ACQUITY SQD UPLC System; column: Waters Acquity UPLC HSS T3 1.8µ 50×1 mm; mobile phase A: 1 l of water+0.25 ml of 99% strength formic acid, mobile phase B: 1 l of acetonitrile+0.25 ml of 99% strength formic acid; gradient: 0.0 min 90% A→1.2 min 5% A→2.0 min 5% A; oven: 50° C.; flow rate: 0.40 ml/min; UV detection: 208-400 nm.

Method 2A:

Instrument: Waters ACQUITY SQD UPLC System; column: Waters Acquity UPLC HSS T3 1.8µ 30×2 mm; mobile phase A: 1 l of water+0.25 ml of 99% strength formic acid, mobile phase B: 1 l of acetonitrile+0.25 ml of 99% strength formic acid; gradient: 0.0 min 90% A→1.2 min 5% A→2.0 min 5% A; oven: 50° C.; flow rate: 0.60 ml/min; UV detection: 208-400 nm.

Method 3A:

Instrument: Micromass Quattro Premier with Waters UPLC Acquity; column: Thermo Hypersil GOLD 1.9µ 50×1 mm; mobile phase A: 1 l of water+0.5 ml of 50% strength formic acid, mobile phase B: 1 l of acetonitrile+0.5 ml of 50% strength formic acid; gradient: 0.0 min 97% A→0.5 min 97% A→3.2 min 5% A→4.0 min 5% A; oven: 50° C.; flow rate: 0.3 ml/min; UV detection: 210 nm.

Method 4A:

MS instrument: Waters (Micromass) Quattro Micro; HPLC instrument: Agilent 1100 series; column: YMC-Triart C18 3µ 50×3 mm; mobile phase A: 1 l of water+0.01 mol of ammonium carbonate, mobile phase B: 1 l of acetonitrile; gradient: 0.0 min 100% A→2.75 min 5% A→4.5 min 5% A; oven: 40° C.; flow rate: 1.25 ml/min; UV detection: 210 nm.

Method 5A:

MS instrument: Waters (Micromass) QM; HPLC instrument: Agilent 1100 series; column: Agient ZORBAX Extend-C18 3.0×50 mm 3.5 micron; mobile phase A: 1 l of water+0.01 mol of ammonium carbonate, mobile phase B: 1 l of acetonitrile; gradient: 0.0 min 98% A→0.2 min 98% A→3.0 min 5% A→4.5 min 5% A; oven: 40° C.; flow rate: 1.75 ml/min; UV detection: 210 nm.

Method 6A:

MS instrument: Waters (Micromass) ZQ; HPLC instrument: Agilent 1100 series; column: Agient ZORBAX Extend-C18 3.0×50 mm 3.5 micron; mobile phase A: 1 l of water+0.01 mol of ammonium carbonate, mobile phase B: 1 l of acetonitrile; gradient: 0.0 min 98% A→0.2 min 98% A→3.0 min 5% A→4.5 min 5% A; oven: 40° C.; flow rate: 1.75 ml/min; UV detection: 210 nm.

Method 7A:

Instrument: Waters ACQUITY SQD UPLC System; column: Waters Acquity UPLC HSS T3 1.8μ 50×1 mm; mobile phase A: 1 l of water+0.25 ml of 99% strength formic acid, mobile phase B: 1 l of acetonitrile+0.25 ml of 99% strength formic acid; gradient: 0.0 min 95% A→6.0 min 5% A→7.5 min 5% A; oven: 50° C.; flow rate: 0.35 ml/min; UV detection: 210-400 nm.

GC-MS Methods:

Method 1B:

Instrument: Thermo DFS, Trace GC Ultra; column: Restek RTX-35, 15 m×200 μm×0.33 μm; constant helium flow rate: 1.20 ml/min; oven: 60° C.; inlet: 220° C.; gradient: 60° C., 30° C./min→300° C. (maintained for 3.33 min).

Method 2B:

Instrument: Micromass GCT, GC6890; column: Restek RTX-35, 15 m×200 μm×0.33 μm; constant helium flow rate: 0.88 ml/min; oven: 70° C.; inlet: 250° C.; gradient: 70° C., 30° C./min 310° C. (maintained for 3 min).

MS Methods:

Method 1C:

Instrument: Thermo Fisher-Scientific DSQ; chemical ionization; reactant gas $NH_3$; source temperature: 200° C.; ionization energy 70 eV.

Method 2C:

Instrument: Waters ZQ 2000; electrospray ionization; mobile phase A: 1 l of water+0.25 ml of 99% strength formic acid, mobile phase B: 1 l of acetonitrile+0.25 ml of 99% strength formic acid; 25% A, 75% B; flow rate: 0.25 ml/min.

Preparative Enantiomer/Diastereomer Separation on a Chiral Phase:

Method 1D:

Phase: Daicel Chiralpak AZ-H, 5 μm 250 mm×30 mm, mobile phase: isohexane/ethanol 50:50; flow rate: 40 ml/min; temperature: 20° C.; UV detection: 220 nm.

Method 2D:

Phase: Daicel Chiralpak AZ-H, 5 μm 250 mm×30 mm, mobile phase: isohexane/ethanol 50:50; flow rate: 40 ml/min; temperature: 25° C.; UV detection: 220 nm.

Method 3D:

Phase: Daicel Chiralpak AD-H SFC, 10 μm 250 mm×20 mm, mobile phase: carbon dioxide/ethanol 70:30; flow rate: 100 ml/min, makeup flow rate: 30 ml/min, backpressure: 80 bar; temperature: 40° C.; UV detection: 220 nm.

Method 4D:

Phase: Daicel Chiralpak AD-H, 5 μm 250 mm×20 mm, mobile phase: isohexane/isopropanol 70:30; flow rate: 20 ml/min; temperature: 25° C.; UV detection: 230 nm.

Method 5D:

Phase: Daicel Chiralpak AZ-H, 5 μm 250 mm×30 mm, mobile phase: isohexane/ethanol 90:10; flow rate: 40 ml/min; temperature: 25° C.; UV detection: 220 nm.

Method 6D:

Phase: Daicel Chiralpak AY-H, 5 μm 250 mm×20 mm, mobile phase: isohexane/ethanol 90:10; flow rate: 40 ml/min; temperature: 40° C.; UV detection: 220 nm.

Method 7D:

Phase: Daicel Chiralpak AS-H, 5 μm 250 mm×20 mm, mobile phase: isohexane/ethanol 70:30; flow rate: 20 ml/min; temperature: 25° C.; UV detection: 230 nm.

Method 8D:

Phase: Daicel Chiralpak AZ-H, 5 μm 250 mm×30 mm, mobile phase: isohexane/ethanol 50:50; flow rate: 20 ml/min; temperature: 25° C.; UV detection: 220 nm.

Method 9D:

Phase: Daicel Chiralpak OZ-H, 5 μm 250 mm×20 mm, mobile phase: isohexane/ethanol 50:50; flow rate: 15 ml/min; temperature: 30° C.; UV detection: 220 nm.

Method 10D:

Phase: Daicel Chiralpak OD-H, 5 μm 250 mm×20 mm, mobile phase: isohexane/ethanol 60:40; flow rate: 20 ml/min; temperature: 22° C.; UV detection: 230 nm.

Analytical Enantiomer/Diastereomer Separation on a Chiral Phase:

Method 1E:

Phase: Daicel Chiralcel OZ-H, 5 μm 250 mm×4.6 mm, mobile phase: isohexane/ethanol 50:50; flow rate: 1 ml/min; temperature: 30° C.; UV detection: 220 nm.

Method 2E:

Phase: Daicel Chiralcel AZ-H, 5 μm 250 mm×4.6 mm, mobile phase: isohexane/ethanol 50:50; flow rate: 1 ml/min; temperature: 30° C.; UV detection: 220 nm.

Method 3E:

Phase: Daicel Chiralpak AD-H SFC, 5 μm 250 mm×4.6 mm, mobile phase: carbon dioxide/ethanol 70:30; flow rate: 3 ml/min; temperature: 30° C.; UV detection: 220 nm.

Method 4E:

Phase: Daicel Chiralpak AD-H, 5 μm 250 mm×4.6 mm, mobile phase: isohexane/isopropanol 50:50; flow rate: 1 ml/min; temperature: 30° C.; UV detection: 220 nm.

Method 5E:

Phase: LUX Amylose-2, 5 μm 250 mm×4.6 mm; mobile phase: isohexane/ethanol 90:10; flow rate: 1 ml/min; temperature: 30° C.; UV detection: 220 nm.

Method 6E:

Phase: Daicel Chiralpak AS-H, 5 μm 250 mm×4.6 mm, mobile phase: isohexane/isopropanol 50:50; flow rate: 1 ml/min; temperature: 30° C.; UV detection: 220 nm.

Method 7E:

Phase: Daicel Chiralcel OD-H, 5 μm 250 mm×4.6 mm; mobile phase: isohexane/ethanol 80:20+0.2% diethylamine; flow rate: 1 ml/min; temperature: 40° C.; UV detection: 220 nm.

Method 8E:

Phase: Daicel Chiralpak AD-H, 5 μm 250 mm×4.6 mm, mobile phase: isohexane/ethanol 50:50; flow rate: 1 ml/min; temperature: 30° C.; UV detection: 220 nm.

Method 9E:

Phase: Daicel Chiralcel OZ-H, 5 μm 250 mm×4.6 mm; mobile phase: isohexane/ethanol 50:50; flow rate: 1 ml/min; temperature: 40° C.; UV detection: 220 nm.

Method 10E:

Phase: Daicel Chiralcel OD-H, 5 μm 250 mm×4.6 mm; mobile phase: isohexane/ethanol 50:50; flow rate: 1 ml/min; temperature: 30° C.; UV detection: 220 nm.

Method 11E:

Phase: Daicel Chiralcel AZ-H, 5 μm 250 mm×4.6 mm; mobile phase: isohexane/ethanol 90:10; flow rate: 1 ml/min; temperature: 30° C.; UV detection: 220 nm.

Preparative Purification:
Method 1F:
Phase: Sunfire C-18, 5 μm 250 mm×20 mm, mobile phase: water/acetonitrile gradient 80:20→5:95; flow rate: 23.75 ml/min+constant addition of 2% strength formic acid, flow rate: 1.25 ml/min, UV detection: 210 nm.
Preparative Diastereomer Separation on an Achiral Phase:
Method 1G:
Phase: Sunfire C-18, 5 μm 250 mm×20 mm, mobile phase: water/methanol 60:40, flow rate: 60 ml/min, temperature: 23° C., UV detection: 210 nm.
Microwave The microwave reactor used was a single-mode instrument of the Biotage Initiator Microwave Synthesizer type.

When compounds according to the invention are purified by preparative HPLC using the methods described above in which the mobile phases contain additives such as, for example, trifluoroacetic acid, formic acid or ammonia, the compounds according to the invention may be obtained in salt form, for example, as trifluoroacetate, formate or ammonium salt, provided the compounds according to the invention contain a sufficiently basic or acidic functionality. Such a salt can be converted into the free base or acid by various methods known to the person skilled in the art.

If, in the synthesis intermediates and working examples of the invention described below, a compound is given in the form of a salt of the corresponding base or acid, the exact stoichiometric composition of such a salt as obtained by the respective preparation and/or purification process is generally not known. Unless specified in more detail, additions to names and structural formulae, such as "hydrochloride", "trifluoroacetate", "sodium salt" or "×HCl", "×CF$_3$COOH", "×Na$^+$" are not to be understood stoichiometrically in the case of such salts, but have only descriptive character with regard to the salt-forming components comprised therein.

This applies correspondingly if the synthesis intermediates and working examples or salts thereof were obtained by the preparation and/or purification processes described in the form of solvates, for example hydrates, whose stoichiometric composition (if of a defined type) is not known.

Starting Materials

Example 1A

Methyl 7-methoxy-2-thioxo-2,3-dihydro-1,3-benzoxazole-5-carboxylate

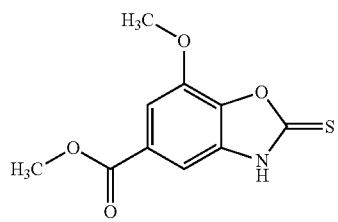 [SMILES: COC(=O)c1cc(OC)c2oc(=S)[nH]c2c1]

20.0 g (101 mmol) of methyl 3-amino-4-hydroxy-5-methoxybenzoate and 17.9 g (112 mmol) of potassium O-ethyl dithiocarbonate were dissolved in pyridine (400 ml), and the solution was stirred under reflux for 3 h (analogously to lit.: R. Lok et al., *J. Org. Chem.* 1996, 61, 3289-3297). The reaction mixture was then cooled and poured onto a mixture of ice (600 g) and concentrated aqueous hydrogen chloride solution (60 ml). The solid formed was filtered off under reduced pressure and washed with water (5×200 ml). The solid was dried initially at 50° C./40 mbar and then under high vacuum. Yield: 23.3 g (96% of theory).

LC-MS (Method 1A): R$_t$=0.79 min; MS (ESIpos): m/z=240 [M+H]$^+$;
$^1$H-NMR (400 MHz, DMSO-d$_6$): δ [ppm]=14.1 (br. s., 1H), 7.45 (d, 1H), 7.32 (d, 1H), 4.00 (s, 3H), 3.88 (s, 3H).

Example 2A

Methyl 2-chloro-7-methoxy-1,3-benzoxazole-5-carboxylate

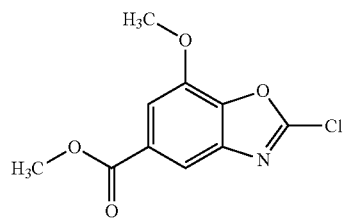 [SMILES: COC(=O)c1cc(OC)c2oc(Cl)nc2c1]

150 g (627 mmol) of 7-methoxy-2-thioxo-2,3-dihydro-1,3-benzoxazole-5-carboxylate were suspended in thionyl chloride (450 ml), catalytic amounts of N,N-dimethylformamide (1.0 ml) were added and the mixture was then stirred for 3 h (analogously to lit.: R. Lok et al., *J. Org. Chem.* 1996, 61, 3289-3297). More N,N-dimethylformamide (1.0 ml) was added, and the mixture was stirred at 70° C. until the evolution of gas had ceased (about 4 h). The reaction solution was concentrated under reduced pressure and the residue was coevaporated with dichloromethane (3×200 ml) to completely remove the thionyl chloride. The solid was dried under high vacuum and then purified by column chromatography on silica gel (dichloromethane). Alternatively, the crude product can also be used further directly. Yield: 125.6 g (82% of theory).

LC-MS (Method 1A): R$_t$=1.00 min; MS (ESIpos): m/z=242 [M+H]$^+$;
$^1$H-NMR (400 MHz, CDCl$_3$): δ [ppm]=7.99 (d, 1H), 7.62 (d, 1H), 4.07 (s, 3H), 3.96 (s, 3H).

Example 3A 1-(3-Chlorophenyl)-2-fluoroethanone

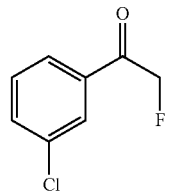 [SMILES: O=C(CF)c1cccc(Cl)c1]

Method 1:
50.7 g (161 mmol) of tetra-n-butylammonium fluoride trihydrate, 22.1 g (214 mmol) of zinc fluoride and 6.22 g (107 mmol) of potassium fluoride were initially charged in acetonitrile (850 ml) and stirred at 80° C. for 1 h (analogously to lit.: X. Zou et al., *J. Fluorine Chem.* 2010, 131, 340-344). 50.0 g (214 mmol) of 2-bromo-1-(3-chlorophenyl)ethanone in acetonitrile (210 mL) were then added dropwise at this temperature over a period of 3 h, and the mixture was subsequently stirred at 80° C. for a further 3 h. The reaction solution was cooled to RT and the precipitated salts were filtered off over a glass frit. The filtrate was concentrated under reduced pressure, water was added to the residue and the mixture was extracted repeatedly with tert-butyl methyl ether. Further precipitated salts were removed by filtration. The organic phases were dried over magnesium sulphate, filtered and concentrated under reduced pressure. The crude product was then purified by flash chromatography on silica gel (petroleum ether/ethyl acetate 10:1). Yield: 27.0 g (58% of theory, purity 80%).

GC-MS (Method 1B): $R_t$=3.73 min; MS (EIpos): m/z=172 [M]$^+$;

$^1$H-NMR (400 MHz, DMSO-d$_6$): δ [ppm]=7.91 (m$_c$, 1H), 7.85 (d$_{br}$, 1H), 7.77 (dd, 1H), 7.60 (m$_c$, 1H), 5.85 (d, 2H).

Method 2:

45.8 g (129 mmol) of 1-(chloromethyl)-4-fluoro-1,4-diazoniabicyclo[2.2.2]octane bistetrafluoroborate (Selectfluor) were added to 10.0 g (64.7 mmol) of 1-(3-chlorophenyl)ethanone in methanol (80.0 ml) and then, in ten portions, stirred in the microwave (Biotage Synthesizer) at 110° C. for 2.5 h (analogously to lit.: B. H. Hoff et al., *Tetrahedron* 2009, 65, 9550-9556.). 5 ml of water were then added to each portion, and the portions were stirred in the microwave at 110° C. for 1 h. The reaction mixtures were then combined, the methanol was removed under reduced pressure and the residue was diluted with water and then extracted with ethyl acetate. The organic phase was dried over sodium sulphate, filtered and concentrated under reduced pressure. The crude product was used for the next step without further purification. Yield: 12.5 g (86% of theory, purity 77%).

GC-MS (Method 2B): $R_t$=3.56 min; MS (EIpos): m/z=172 [M]$^+$.

Example 4A 1-(3-Chlorophenyl)-2-fluoroethanamine [racemate]

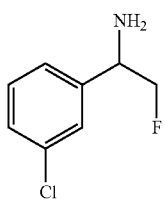 [SMILES: NC(CF)c1cccc(Cl)c1]

Method 1:

82.0 g (86.3 ml, 289 mmol) of titanium tetraisopropoxide were added dropwise to 24.9 g (144.0 mmol) of 1-(3-chlorophenyl)-2-fluoroethanone in 2 M ethanolic ammonia solution (361 ml, 722 mmol), the temperature being kept at 20° C. by ice cooling, and the mixture was then stirred at RT overnight. At 10° C., 8.19 g (216 mmol) of sodium borohydride were then added a little at a time, and the mixture was stirred at RT for 6 h. A further 1.64 g (43.2 mmol) of sodium borohydride were then added, and the mixture was stirred overnight. Semiconcentrated aqueous hydrogen chloride solution (300 ml) was added to the reaction solution, and the mixture was then diluted with water (1.0 l) (pH=2). The mixture was extracted with tert-butyl methyl ether (3×500 ml), and the organic phases were then dried over sodium sulphate, filtered and concentrated under reduced pressure. Yield: 10.5 g (purity: 58%).

The aqueous phase was adjusted to pH=10 with 45% strength aqueous sodium hydroxide solution, saturated with sodium chloride and extracted with tert-butyl methyl ether (3×500 ml). The combined organic phases were dried over sodium sulphate, filtered and concentrated under reduced pressure. This gave a further 12.9 g (51% of theory) of the desired product.

LC-MS (Method 5A): $R_t$=1.93 min; MS (ESIpos): m/z=174 [M+H]$^+$;

$^1$H-NMR (400 MHz, DMSO-d$_6$): δ [ppm]=7.50 (s, 1H), 7.40-7.27 (m, 3H), 4.45 (m$_c$, 1H), 4.32 (m$_c$, 1H), 4.12 (dt, 1H), 2.10 (br. s., 2H).

The product fractions were combined and used for the next step without further purification.

Method 2:

Under an atmosphere of argon, 8.20 g (38.0 mmol, purity: 80%) of 1-(3-chlorophenyl)-2-fluoroethanone were dissolved in 2 M ethanolic ammonia solution (95 ml, 190 mmol), 21.6 g (22.8 ml, 76.0 mmol) of titanium tetraisopropoxide were added and the mixture was stirred at RT for 16 h. 1.51 g (57.3 mmol) of sodium borohydride were then added, and the mixture was stirred at RT for 5 h. A further 700 mg (18.5 mmol) of sodium borohydride were added, and the mixture was stirred at RT overnight. Using 6 M aqueous hydrogen chloride solution, the reaction solution was adjusted to pH=2 and then extracted three times with tert-butyl methyl ether. The aqueous phase was adjusted to pH=10 with sodium hydroxide, saturated with sodium chloride and extracted four times with tert-butyl methyl ether. The combined organic phases were dried over sodium sulphate, filtered and concentrated under reduced pressure. The residue was taken up in dichloromethane and washed with saturated aqueous sodium bicarbonate solution. The organic phase was dried over sodium sulphate, filtered and concentrated under reduced pressure. The target compound was used for the next step without further purification. Yield: 7.32 g (90% of theory, purity: 81%).

LC-MS (Method 5A): $R_t$=1.92 min; MS (ESIpos): m/z=174 [M+H]$^+$.

Example 5A 1-(3-Chlorophenyl)-2-fluoroethanamine hydrochloride [racemate]

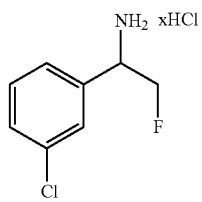

Method 1:

Under an atmosphere of argon, 6.52 g (6.87 ml, 23.0 mmol) of titanium tetraisopropoxide were added to 2.00 g (11.5 mmol) of 1-(3-chlorophenyl)-2-fluoroethanone in 2 M ethanolic ammonia solution (28.7 ml, 57.4 mmol), and the mixture was stirred at RT for 16 h. 654 mg (17.3 mmol) of sodium borohydride were then added, and the mixture was stirred at RT for 5 h. A further 350 mg (9.25 mmol) of sodium borohydride were added, and the mixture was stirred at RT overnight. The reaction solution was poured into 25% strength aqueous ammonia solution (100 ml) and then filtered through kieselguhr. tert-Butyl methyl ether (200 ml) was added to the filtrate, and the mixture was extracted. After phase separation, the aqueous phase was extracted with tert-butyl methyl ether (100 ml). The combined organic phases were dried over sodium sulphate, filtered and concentrated under reduced pressure. The crude product was dissolved in diethyl ether/tetrahydrofuran (5:1; 60 ml), and a 4 N solution of hydrogen chloride in 1,4-dioxane (10.0 ml) was then added. The solid formed was filtered off under reduced pressure, washed with a little diethyl ether and dried under high vacuum. Yield: 1.54 g (63% of theory).

LC-MS (Method 5A): $R_t$=1.94 min; MS (ESIpos): m/z=174 [M+H−HCl]$^+$;

$^1$H-NMR (400 MHz, DMSO-d$_6$): δ [ppm]=8.98 (br. s., 3H), 7.70 (s, 1H), 7.60-7.47 (m, 3H), 4.88-4.67 (m, 3H).

Method 2:

1.10 kg (1.16 l, 3.88 mol) of titanium tetraisopropoxide were added dropwise to 335 g (1.94 mol) of 1-(3-chlorophenyl)-2-fluoroethanone in 2 M ethanolic ammonia solution (4.85 l, 9.71 mol) (the temperature was kept at 20° C. by ice cooling), and the mixture was stirred at RT overnight. At 10° C., 110 g (2.91 mol) of sodium borohydride were then added in four portions, and the mixture was stirred at RT for 36 h. A further 29.4 g (776 mmol) of sodium borohydride were added, and the mixture was stirred at RT for 1 h. The reaction solution was poured into 2 M aqueous ammonia solution (4.85 l) and the precipitated salts were then filtered off over a frit under reduced pressure. tert-Butyl methyl ether (14 l) and water (50 l) were added to the filtrate, the mixture was extracted and 5% aqueous sodium chloride solution was then added to facilitate phase separation. After phase separation, the aqueous phase was re-extracted with tert-butyl methyl ether (5 l) and the combined organic phases were dried over sodium sulphate, filtered and concentrated under reduced pressure. The crude product was dissolved in diethyl ether/tetrahydrofuran (10:1; 1.1 l), and a 4 N solution of hydrogen chloride in 1,4-dioxane (385 ml) was then added with stirring and ice cooling. The precipitated white solid was filtered off under reduced pressure, washed with a little diethyl ether and dried under high vacuum. Yield: 261 g (77% of theory).

LC-MS (Method 5A): $R_t$=1.93 min; MS (ESIpos): m/z=174 [M+H−HCl]$^+$;

Example 6A tert-Butyl [1-(3-chlorophenyl)-2-fluoroethyl]carbamate [racemate]

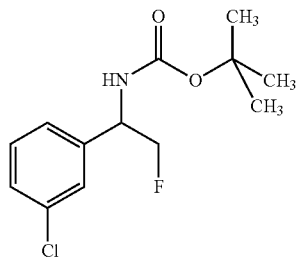 [SMILES: CC(C)(C)OC(=O)NC(CF)c1cccc(Cl)c1]

Method 1:

7.47 g (43.3 mmol) of 1-(3-chlorophenyl)-2-fluoroethanamine [racemate] were suspended in dichloromethane (150 ml), first 9.14 g (12.6 ml, 90.4 mmol) of triethylamine and then 10.3 g (47.3 mmol) of di-tert-butyl dicarbonate were added and the mixture was stirred at RT overnight. The reaction solution was then washed with 0.5 N aqueous hydrogen chloride solution (100 ml), saturated aqueous sodium bicarbonate solution (100 ml) and water (100 ml). The organic phase was dried over sodium sulphate, filtered and concentrated under reduced pressure. The crude product was purified by preparative RP-HPLC (water/acetonitrile). Yield: 7.23 g (61% of theory).

LC-MS (Method 1A): $R_t$=1.10 min; MS (ESIpos): m/z=218 [M+H−C$_4$H$_9$]$^+$;

$^1$H-NMR (400 MHz, DMSO-d$_6$): δ [ppm]=7.72 (d, 1H), 7.45 (s, 1H), 7.41-7.29 (m, 3H), 4.89 (m$_c$, 1H), 4.59-4.45 (m, 1H), 4.45-4.32 (m, 1H), 1.38 (s, 9H).

Method 2:

Under an atmosphere of argon, 41.5 g (198 mmol) of 1-(3-chlorophenyl)-2-fluoroethanamine hydrochloride [racemate] were suspended in dichloromethane (200 ml), and subsequently first 80.0 g (110 ml, 790 mmol) of triethylamine and then dichloromethane (200 ml) were added. 31.0 g (142 mmol) of di-tert-butyl dicarbonate in dichloromethane (100 ml) were added, and the mixture was stirred at RT overnight. A further 9.91 g (45.4 mmol) of di-tert-butyl dicarbonate were added, and the mixture was stirred until conversion was almost complete (monitored by TLC). The reaction solution was washed with 1 N aqueous hydrogen chloride solution (2×100 ml) and saturated aqueous sodium bicarbonate solution (100 ml). The organic phase was dried over sodium sulphate, filtered and concentrated under reduced pressure. Yield: 51.0 g (94% of theory).

LC-MS (Method 7A): $R_t$=3.25 min; MS (ESIpos): m/z=218 [M+H−C$_4$H$_9$]$^+$.

Example 7A tert-Butyl [1-(3-chlorophenyl)-2-fluoroethyl]carbamate [enantiomerically pure isomer 1]

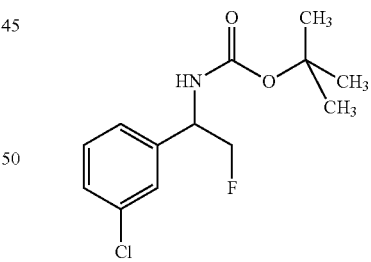

Enantiomer separation on a chiral phase of 7.23 g of the compound from Example 6A according to Method 6D gave 3.05 g of Example 7A (enantiomerically pure isomer 1) and 3.05 g of Example 8A (enantiomerically pure isomer 2).

HPLC (Method 6E): $R_t$=5.01 min, 99.0% ee;

LC-MS (Method 7A): $R_t$=3.26 min; MS (ESIpos): m/z=218 [M+H−C$_4$H$_9$]$^+$;

$^1$H-NMR (400 MHz, DMSO-d$_6$): δ [ppm]=7.72 (d, 1H), 7.45 (s, 1H), 7.42-7.27 (m, 3H), 4.89 (m$_c$, 1H), 4.59-4.45 (m, 1H), 4.44-4.31 (m, 1H), 1.38 (s, 9H).

Example 8A tert-Butyl [1-(3-chlorophenyl)-2-fluoroethyl]carbamate [enantiomerically pure isomer 2]

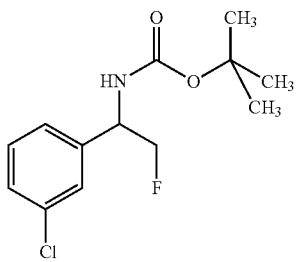 [SMILES: CC(C)(C)OC(=O)NC(CF)c1cccc(Cl)c1]

Enantiomer separation on a chiral phase of 7.23 g of the compound from Example 6A according to Method 6D gave 3.05 g of Example 7A (enantiomerically pure isomer 1) and 3.05 g of Example 8A (enantiomerically pure isomer 2).

HPLC (Method 6E): $R_t$=7.46 min, 99.0% ee;

LC-MS (Method 7A): $R_t$=3.26 min; MS (ESIpos): m/z=218 [M+H−$C_4H_9$]$^+$;

$^1$H-NMR (400 MHz, DMSO-$d_6$): δ [ppm]=7.72 (d, 1H), 7.45 (s, 1H), 7.42-7.28 (m, 3H), 4.89 ($m_c$, 1H), 4.58-4.45 (m, 1H), 4.44-4.30 (m, 1H), 1.38 (s, 9H).

Example 9A 1-(3-Chlorophenyl)-2-fluoroethanamine hydrochloride [enantiomerically pure isomer]

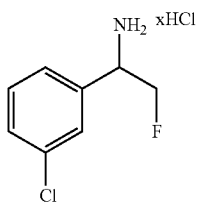 [SMILES: NC(CF)c1cccc(Cl)c1]

17.3 g (63.2 mmol) of tert-butyl [1-(3-chlorophenyl)-2-fluoroethyl]carbamate [enantiomerically pure isomer 2] were initially charged in 1,4-dioxane (50 ml), and 79 ml (316 mmol) of 4 N hydrogen chloride solution in 1,4-dioxane were then added at RT. A solid formed after a short period of time. 1,4-Dioxane (250 ml) and then 31.6 ml (126 mmol) of 4 N hydrogen chloride solution in 1,4-dioxane were added, and the mixture was stirred at RT overnight. The suspension formed was concentrated completely under reduced pressure, the residue was triturated with tert-butyl methyl ether (200 ml) and filtered and the filter residue was washed with tert-butyl methyl ether (2×50 ml). The solid formed was dried under high vacuum. Yield: 13.2 g (99% of theory).

Optical rotation: $[α]_D^{19.9}$=27.06° (c=0.51, methanol),

LC-MS (Method 5A): $R_t$=1.94 min; MS (ESIpos): m/z=174 [M+H]$^+$;

$^1$H-NMR (400 MHz, DMSO-$d_6$): δ [ppm]=8.91 (br. s., 3H), 7.68 (s, 1H), 7.55-7.47 (m, 3H), 4.89-4.66 (m, 3H).

Example 10A

Methyl 2-{[1-(3-chlorophenyl)-2-fluoroethyl]amino}-7-methoxy-1,3-benzoxazole-5-carboxylate [racemate]

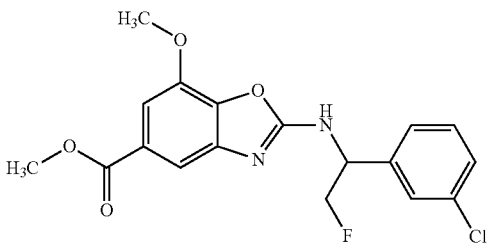 [SMILES: COC(=O)c1cc(OC)c2oc(NC(CF)c3cccc(Cl)c3)nc2c1]

At RT, 2.22 g (2.99 ml, 17.2 mmol) of N,N-diisopropylethylamine were added to 1.82 g (5.73 mmol, purity: 78%) of methyl 2-chloro-7-methoxy-1,3-benzoxazole-5-carboxylate and 2.03 g (5.73 mmol, purity: 49%) of 1-(3-chlorophenyl)ethanamine [racemate] in 1,4-dioxane (78 ml), and the mixture was then stirred for 1 h. The reaction solution was stirred under reflux for 5 h and then stirred at RT overnight. The mixture was then concentrated under reduced pressure, the residue was taken up in diethyl ether and a little dichloromethane was added, the mixture was stirred and the precipitated solid was filtered off under reduced pressure and washed with diethyl ether. Yield: 1.42 g (37% of theory, purity: 56%). The filtrate was purified by preparative RP-HPLC (acetonitrile/water), giving a further 665 mg (22% of theory, purity: 71%) of the desired product.

LC-MS (Method 1A): $R_t$=1.10 min; MS (ESIpos): m/z=379 [M+H]$^+$.

Example 11A

2-{[1-(3-Chlorophenyl)-2-fluoroethyl]amino}-7-methoxy-1,3-benzoxazole-5-carboxylic acid [racemate]

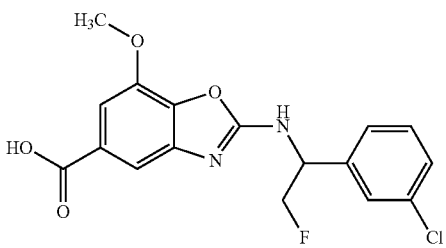 [SMILES: COc1cc(C(=O)O)cc2nc(NC(CF)c3cccc(Cl)c3)oc12]

628 mg (1.31 mmol, purity: 79%) of methyl 2-{[1-(3-chlorophenyl)-2-fluoroethyl]amino}-7-methoxy-1,3-benzoxazole-5-carboxylate [racemate] were dissolved in 1,4-dioxane (80 ml), and 1 N aqueous sodium hydroxide solution (20 ml) was then added. The mixture was stirred at RT for 18 h. Most of the 1,4-dioxane was then removed under reduced pressure and the residue was taken up in 1 N aqueous hydrogen chloride solution and extracted repeatedly with ethyl acetate. The organic phases were dried over sodium sulphate, filtered and concentrated under reduced pressure. The residue was triturated with acetonitrile and the precipitated solid was filtered off under reduced pressure and dried under high vacuum. Yield: 134 mg (17% of theory, purity 60%). The filtrate was purified by preparative RP-HPLC (acetonitrile/water), giving a second batch of product. Yield: 137 mg (23% of theory, purity 80%).

LC-MS (Method 1A): $R_t$=0.93 min; MS (ESIpos): m/z=365 [M+H]$^+$.

Example 12A

Methyl 2-{[1-(3-chlorophenyl)-2-fluoroethyl]amino}-7-methoxy-1,3-benzoxazole-5-carboxylate [enantiomerically pure isomer]

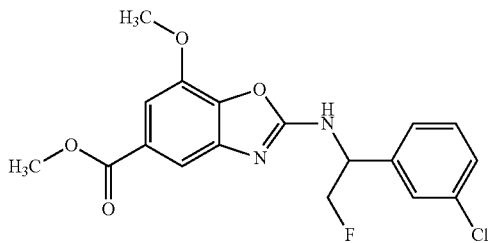 [SMILES: COC(=O)c1cc(OC)c2oc(NC(CF)c3cccc(Cl)c3)nc2c1]

Method 1:

Under argon, 15.2 g (62.8 mmol) of methyl 2-chloro-7-methoxy-1,3-benzoxazole-5-carboxylate were initially charged in N,N-dimethylformamide (100 ml), and 13.2 g (62.8 mmol) of 1-(3-chlorophenyl)-2-fluoroethanamine hydrochloride [Example 9A, enantiomerically pure isomer] and 32.5 g (43.8 ml, 251 mol) of N,N-diisopropylethylamine were then added at RT. The reaction solution was stirred at 70° C. (oil bath temperature) for 2 h, and a further 264 mg (1.26 mmol) of 1-(3-chlorophenyl)-2-fluoroethanamine hydrochloride [Example 9A] were added. The mixture was stirred at 70° C. (oil bath temperature) for 1 h and then cooled and poured into ice-water. After phase separation, tert-butyl methyl ether (500 ml) was added to the aqueous phase, and the mixture was stirred for 10 min. The suspension formed was filtered through a glass frit under reduced pressure and the solid was repeatedly triturated with tert-butyl methyl ether and filtered under reduced pressure. The aqueous phase was extracted with tert-butyl methyl ether (2×300 ml) and the combined organic phases were concentrated under reduced pressure. The residue was once more triturated with tert-butyl methyl ether, filtered and concentrated under reduced pressure. Both solids fractions were then combined and dried under high vacuum. Yield: 18.4 g (77% of theory).

LC-MS (Method 5A): $R_t$=2.56 min; MS (ESIpos): m/z=379 [M+H]$^+$;

$^1$H-NMR (400 MHz, DMSO-$d_6$): δ [ppm]=9.10 (d, 1H), 7.59 (s, 1H), 7.50-7.35 (m, 4H), 7.31 (d, 1H), 5.26 ($m_c$, 1H), 4.82-4.53 (m, 2H), 3.96 (s, 3H), 3.84 (s, 3H).

Method 2:

Under argon, 125 g (517 mmol) of methyl 2-chloro-7-methoxy-1,3-benzoxazole-5-carboxylate were initially charged in N,N-dimethylformamide (850 ml), and 114 g (543 mmol) of 1-(3-chlorophenyl)-2-fluoroethanamine hydrochloride and 267 g (360 ml, 2.07 mol) of N,N-diisopropylethylamine were added at RT. The reaction solution was stirred at 70° C. (oil bath temperature) for 4 h, 8.69 g (41.4 mmol) of 1-(3-chlorophenyl)-2-fluoroethanamine hydrochloride were then added and the mixture was stirred at RT overnight (about 14 h). A further 1.09 g (5.17 mmol) of 1-(3-chlorophenyl)-2-fluoroethanamine hydrochloride were added, and the mixture was stirred at 70° C. (oil bath temperature) for 2 h and then concentrated under reduced pressure. The residue was taken up in tert-butyl methyl ether (2.0 l) and the organic phase was washed with water (3×1.0 l). Under reduced pressure, the organic phase was concentrated to about one third of its original volume, and the precipitated solid was then filtered off under reduced pressure. The solid precipitated in the aqueous phase was likewise filtered off under reduced pressure and then washed with tert-butyl methyl ether (2×100 ml). The combined solids were dried under high vacuum. Yield: 181 g (92% of theory).

Optical rotation: $[\alpha]_D^{20.2}$=77.20° (c=0.465, methanol);

LC-MS (Method 5A): $R_t$=2.57 min; MS (ESIpos): m/z=379 [M+H]$^+$;

$^1$H-NMR (400 MHz, DMSO-$d_6$): δ [ppm]=9.11 (d, 1H), 7.59 (s, 1H), 7.51-7.35 (m, 4H), 7.31 (s, 1H), 5.27 ($m_c$, 1H), 4.83-4.50 (m, 2H), 3.96 (s, 3H), 3.84 (s, 3H).

Example 13A

2-{[1-(3-Chlorophenyl)-2-fluoroethyl]amino}-7-methoxy-1,3-benzoxazole-5-carboxylic acid [enantiomerically pure isomer]

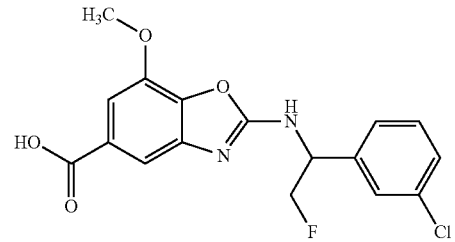 [SMILES: COc1cc(C(=O)O)cc2nc(NC(CF)c3cccc(Cl)c3)oc12]

181 g (478 mmol) of methyl 2-{[1-(3-chlorophenyl)-2-fluoroethyl]amino}-7-methoxy-1,3-benzoxazole-5-carboxylate [enantiomerically pure isomer] were initially charged in 1,4-dioxane (2.4 l), and a cold (about 8° C.) solution of 425 g (287 ml, 4.78 mol) of 45% strength aqueous sodium hydroxide solution in water (2.35 l) was then added. The mixture was stirred at RT for 4 h and then diluted with water (2.0 l). The reaction solution was extracted with tert-butyl methyl ether (2×1.0 l), ice was added to the aqueous phase and the aqueous phase was acidified with concentrated hydrogen chloride solution (about 450 ml). The mixture was stirred at 10° C. for 15 min, the precipitated solid was filtered off under reduced pressure and the residue was washed with water (2×1.0 l), left at RT overnight and then dried at 60° C. for 4 h and then at 50° C. under reduced pressure until the mass remained constant. Yield: 172 g (98% of theory, purity 89%).

LC-MS (Method 1A): $R_t$=0.92 min; MS (ESIpos): m/z=365 [M+H]$^+$;

$^1$H-NMR (400 MHz, DMSO-$d_6$): δ [ppm]=12.85 (br. s., 1H), 9.06 (d, 1H), 7.59 (s, 1H), 7.51-7.46 (m, 1H), 7.45-7.35 (m, 3H), 7.31 (d, 1H), 5.32-5.20 (m, 1H), 4.81-4.54 (m, 2H), 3.95 (s, 3H).

Example 14A

3-Methylpiperidin-4-ol [racemic trans-diastereomer, 2 isomers]

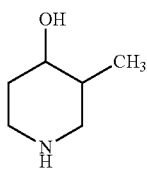

2.82 g (13.7 mmol) of 1-benzyl-3-methylpiperidin-4-ol [racemic trans-diastereomer, 2 isomers; lit.: M.-J. Blanco-Pilado et al., WO 2004/094380 A1] were initially charged in ethanol (250 ml), 1.46 g of palladium on carbon (10%) were added and the mixture was shaken at RT and a 3.5 bar hydrogen atmosphere in a Parr apparatus overnight. The reaction solution was filtered to remove the catalyst and the filtrate was concentrated under reduced pressure. Yield: 1.26 g (79% of theory).

GC-MS (Method 2B): $R_t$=2.23 min; MS (EIpos): m/z=115 [M]$^+$;

$^1$H-NMR (400 MHz, DMSO-d$_6$): δ [ppm]=4.48 (br. s., 1H), 2.95-2.75 (m, 3H), 2.37 (td, 1H), 2.05-1.96 (m, 1H), 1.68 (m$_c$, 1H), 1.27-1.13 (m, 2H), 0.83 (d, 3H).

Example 15A

N-Benzyl-2-chloro-N-(1,3-dihydroxypropan-2-yl)propanamide [racemate]

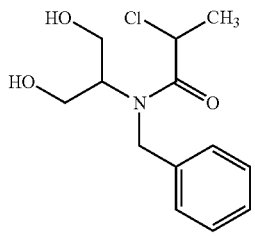 [SMILES: CC(Cl)C(=O)N(Cc1ccccc1)C(CO)CO]

60.5 g (334 mmol) of 2-(benzylamino)propane-1,3-diol [lit.: W. Lacôte et al., Org. Lett. 2011, 13, 5990-5993] were initially charged in isopropanol (0.93 l), the mixture was cooled to 0° C. and 50.7 g (69.8 ml, 501 mmol) of triethylamine were added. 50.9 g (38.9 ml, 401 mmol) of 2-chloropropionyl chloride [racemate] were then added dropwise. The reaction solution was allowed to warm to RT and then concentrated under reduced pressure. 0.5 N aqueous hydrogen chloride solution was added to the residue, and the mixture was extracted with dichloromethane. The organic phases were dried over sodium sulphate, filtered and concentrated under reduced pressure. The crude product was used for the next step without further purification. Yield: 91.7 g (94% of theory).

LC-MS (Method 1A): $R_t$=0.71 min; MS (ESIpos): m/z=272 [M+H]$^+$.

Example 16A

4-Benzyl-5-(hydroxymethyl)-2-methylmorpholin-3-one [diastereomer mixture, 4 isomers]

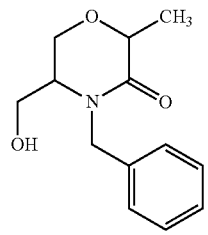 [SMILES: CC1OCC(CO)N(Cc2ccccc2)C1=O]

81.3 g (272 mmol, purity: 91%) of N-benzyl-2-chloro-N-(1,3-dihydroxypropan-2-yl)propanamide [racemate] were initially charged in isopropanol (600 ml), the mixture was cooled to 0° C. and 91.6 g (817 mmol) of potassium tert-butoxide were added. The reaction solution was allowed to warm to RT and was stirred at RT overnight. Most of the isopropanol was removed under reduced pressure and the residue was taken up in dichloromethane. The mixture was washed with water and the organic phase was dried over magnesium sulphate, filtered and concentrated under reduced pressure. The crude product was used for the next step without further purification. Yield: 61.7 g (96% of theory, diastereomer ratio about 7:3).

LC-MS (Method 2A): $R_t$=0.61 min (diastereomer 1, 2 isomers), $R_t$=0.62 min (diastereomer 2, 2 isomers);
MS (ESIpos): m/z=236 [M+H]$^+$.

Example 17A

4-Benzyl-5-({[tert-butyl(dimethyl)silyl]oxy}methyl)-2-methylmorpholin-3-one [diastereomer mixture, 4 isomers]

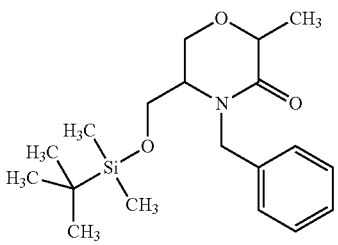 [SMILES: CC1OCC(CO[Si](C)(C)C(C)(C)C)N(Cc2ccccc2)C1=O]

21.5 g (91.4 mmol) of 4-benzyl-5-(hydroxymethyl)-2-methylmorpholin-3-one [diastereomer mixture, 4 isomers] were initially charged in N,N-dimethylformamide (126 ml), and 12.4 g (183 mmol) of imidazole and then 14.5 g (96.0 mmol) of tert-butyldimethylsilyl chloride were added at RT. The mixture was stirred for 2 h, and most of the solvent was then removed under reduced pressure. The residue was taken up in ethyl acetate/water and the organic phase was washed with water, 0.4 N aqueous hydrogen chloride solution, saturated aqueous sodium bicarbonate solution and water. The organic phase was dried over sodium sulphate, filtered and concentrated under reduced pressure. The crude product was used for the next step without further purification. Yield: 31.2 g (97% of theory, diastereomer ratio about 7:3).

LC-MS (Method 1A): $R_t$=1.41 min; MS (ESIpos): m/z=350 [M+H]$^+$;

$^1$H-NMR (400 MHz, DMSO-d$_6$): δ [ppm]=7.38-7.18 (m, 5H), 5.00 (d, 0.3H), 4.95 (d, 0.7H), 4.32-4.19 (m, 2H), 3.92-3.85 (m, 1H), 3.75-3.62 (m, 3H), 3.32-3.26 (m, 0.3H), 3.19-3.13 (m., 0.7H), 1.35 (d, 0.9H), 1.32 (d, 2.1H), 0.84-0.80 (m, 9H), 0.04-0.03 (m, 6H).

Example 18A

4-Benzyl-5-({[tert-butyl(dimethyl)silyl]oxy}methyl)-2,2-dimethylmorpholin-3-one [racemate]

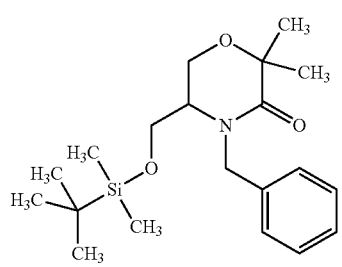

17.0 g (70.7 mmol) of 4-benzyl-5-({[tert-butyl(dimethyl)silyl]oxy}methyl)-2-methylmorpholin-3-one [diastereomer mixture, 4 isomers] were initially charged in tetrahydrofuran (340 ml), and 32.4 ml (58.4 mmol) of lithium diisopropylamide solution (1.8 M in tetrahydrofuran/n-heptane/ethylbenzene) were added at −78° C. The mixture was warmed slowly to 0° C., and 8.97 g (3.94 ml, 63.2 mmol) of iodomethane were then added. After 1.5 h, the mixture was again cooled to −78° C., and 5.40 ml (9.73 mmol) of lithium diisopropylamide solution (1.8 M in tetrahydrofuran/n-heptane/ethylbenzene) were added.

The mixture was then warmed to 0° C., and 2.07 g (0.91 ml, 14.6 mmol) of iodomethane were added. After 1 h, water was added to the reaction solution with cooling, the tetrahydrofuran was removed under reduced pressure, the residue was taken up in ethyl acetate and then washed with water and saturated aqueous sodium chloride solution. The organic phase was dried over sodium sulphate, filtered and concentrated under reduced pressure. The crude product was used for the next step without further purification. Yield: 19.8 g (98% of theory, purity: 88%).

LC-MS (Method 1A): $R_t$=1.45 min; MS (ESIpos): m/z=364 [M+H]$^+$.

Example 19A

4-Benzyl-5-(hydroxymethyl)-2,2-dimethylmorpholin-3-one [racemate]

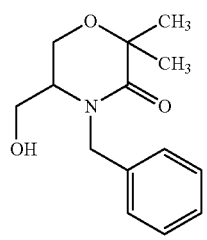 [SMILES: CC1(C)OCC(CO)N(Cc2ccccc2)C1=O]

18.1 g (43.8 mmol, purity: 88%) of 4-benzyl-5-({[tert-butyl(dimethyl)silyl]oxy}methyl)-2,2-dimethylmorpholin-3-one [racemate] were initially charged in tetrahydrofuran (329 ml), 110 ml (110 mmol) of tetra-n-butylammonium fluoride solution (1.0 M in tetrahydrofuran) were added at RT and the mixture was stirred overnight. The reaction solution was then concentrated under reduced pressure and the residue was taken up in ethyl acetate and washed with water. The organic phase was dried over sodium sulphate, filtered and concentrated under reduced pressure. The crude product was purified by column chromatography on silica gel (dichloromethane, dichloromethane/methanol 100:3). Yield: 9.99 g (89% of theory).

LC-MS (Method 1A): $R_t$=0.73 min; MS (ESIpos): m/z=250 [M+H]$^+$;

$^1$H-NMR (400 MHz, DMSO-d$_6$): δ [ppm]=7.43-7.35 (m, 2H), 7.34-7.21 (m, 3H), 5.09-4.98 (m, 2H), 4.23 (d, 1H), 3.90-3.75 (m, 2H), 3.65-3.55 (m, 2H), 3.15 (br. t., 1H), 1.42 (s, 3H), 1.39 (s, 3H).

Example 20A (4-Benzyl-6,6-dimethylmorpholin-3-yl)methanol [racemate]

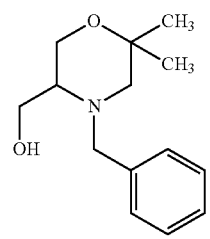 [SMILES: CC1(C)CN(Cc2ccccc2)C(CO)CO1]

1.00 g (4.01 mmol) of 4-benzyl-5-(hydroxymethyl)-2,2-dimethylmorpholin-3-one [racemate] was initially charged in tetrahydrofuran (39 ml), 8.02 ml (16.0 mmol) of 2 M borane/dimethyl sulphide complex solution in tetrahydrofuran were added under argon and the mixture was stirred under reflux for 2 h. The mixture was subsequently cooled to 0° C., methanol (10 ml) was added carefully and the mixture was stirred under reflux for 30 min. The mixture was then concentrated completely under reduced pressure, and the residue was taken up in acetonitrile and purified by preparative RP-HPLC (acetonitrile/water, isocratic).

Yield: 587 mg (58% of theory).

LC-MS (Method 5A): $R_t$=2.19 min; MS (ESIpos): m/z=236 [M+H]$^+$.

Example 21A (6,6-Dimethylmorpholin-3-yl)methanol [racemate]

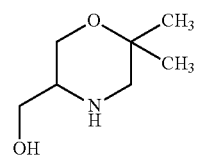

587 mg (2.49 mmol) of (4-benzyl-6,6-dimethylmorpholin-3-yl)methanol [racemate] were initially charged in ethanol (20 ml), 58.7 mg of palladium on carbon (10%) and 29.4 mg of palladium hydroxide on carbon (20%) were added under argon and the mixture was then stirred under an atmosphere of hydrogen at standard pressure overnight. The reaction solution was filtered through kieselguhr and the residue was washed with ethanol. The filtrate was concentrated under reduced pressure and the product was dried under high vacuum. Yield: 385 mg (quant.).

LC-MS (Method 6A): $R_t$=0.68 min; MS (ESIpos): m/z=146 [M+H]$^+$;

$^1$H-NMR (400 MHz, DMSO-d$_6$): δ [ppm]=4.54 (t, 1H), 3.46 (dd, 1H), 3.30-3.22 (m, 3H), 2.62-2.55 (m, 2H), 2.45 (d, 1H), 2.17 (br. s., 1H), 1.17 (s, 3H), 1.04 (s, 3H).

Example 22A

N-Benzyl-2-chloro-N-[(2R)-1-hydroxypropan-2-yl] propanamide [diastereomer mixture, 2 isomers]

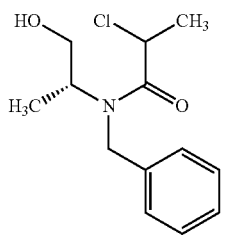 [SMILES: CC(Cl)C(=O)N(Cc1ccccc1)[C@H](C)CO]

16.4 g (99.3 mmol) of (2R)-2-(benzylamino)propan-1-ol [lit.: T. J. Tewson et al., *Synthesis* 2002, 6, 766-770] were initially charged in isopropanol (500 ml), the mixture was cooled to 0° C. and 20.1 g (27.7 ml, 199 mmol) of triethylamine were added. 13.9 g (10.8 ml, 109 mmol) of 2-chloropropionyl chloride [racemate] were then added dropwise, and the reaction solution was allowed to warm to RT, stirred overnight and then concentrated under reduced pressure. 0.5 N aqueous hydrogen chloride solution was added to the residue, and the mixture was extracted with ethyl acetate. The organic phases were dried over sodium sulphate, filtered and concentrated under reduced pressure. The crude product was used for the next step without further purification. Yield: 24.3 g (88% of theory, purity: 92%, diastereomer ratio about 1:1).

LC-MS (Method 1A): $R_t$=0.80 min (diastereomer 1), $R_t$=0.84 min (diastereomer 2);
MS (ESIpos): m/z=256 [M+H]$^+$.

Example 23A (5R)-4-Benzyl-2,5-dimethylmorpholin-3-one [diastereomer mixture, 2 isomers]

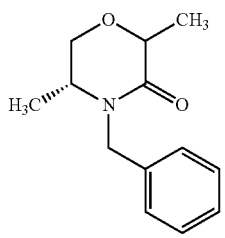 [SMILES: CC1OC[C@@H](C)N(Cc2ccccc2)C1=O]

30.0 g (109 mmol, purity: 93%) of N-benzyl-2-chloro-N-[(2R)-1-hydroxypropan-2-yl]propanamide [diastereomer mixture, 2 isomers] were initially charged in isopropanol (588 ml), the mixture was cooled to 0° C. and 49.0 g (436 mmol) of potassium tert-butoxide were added. The reaction solution was allowed to warm to RT and was stirred overnight. Most of the isopropanol was removed under reduced pressure, and the residue was taken up in water. The mixture was extracted with ethyl acetate, and the organic phases were dried over magnesium sulphate, filtered and concentrated under reduced pressure. The crude product was used for the next step without further purification. Yield: 22.8 g (93% of theory).

LC-MS (Method 1A): $R_t$=0.85 min; MS (ESIpos): m/z=220 [M+H]$^+$.

Example 24A (5R)-4-Benzyl-2,5-dimethylmorpholine [enantiomerically pure isomers 1+2]

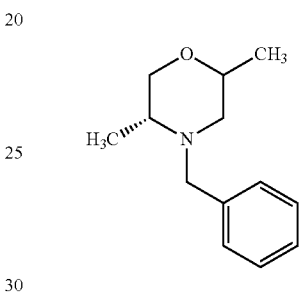

27.0 g (123 mmol) of (5R)-4-benzyl-2,5-dimethylmorpholin-3-one [diastereomer mixture, 2 isomers] were initially charged in tetrahydrofuran (400 ml), 184 ml (369 mmol) of 2 M borane/dimethyl sulphide complex solution in tetrahydrofuran were added under argon and the mixture was stirred under reflux for 2 h. The mixture was subsequently cooled to 0° C., methanol (200 ml) was added carefully and the mixture was stirred under reflux for 2 h. The mixture was then concentrated completely under reduced pressure, and the residue was taken up in acetonitrile and purified by preparative RP-HPLC (acetonitrile/water, isocratic) and separated into the diastereomers. This gave 2.60 g (10% of theory) of the enantiomerically pure diastereomer 1, which elutes first, and 9.00 g (35% of theory) of the enantiomerically pure diastereomer 2, which elutes later.

Enantiomerically Pure Isomer 1:
LC-MS (Method 6A): $R_t$=2.30 min; MS (ESIpos): m/z=206 [M+H]$^+$;
Enantiomerically Pure Isomer 2:
LC-MS (Method 6A): $R_t$=2.46 min; MS (ESIpos): m/z=206 [M+H]$^+$.

Example 25A (5R)-2,5-Dimethylmorpholine hydrochloride [enantiomerically pure isomer 1]

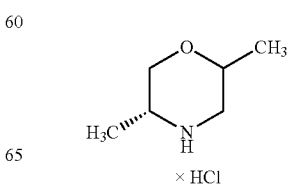

2.60 g (12.7 mmol) of (5R)-4-benzyl-2,5-dimethylmorpholine (Example 24A, enantiomerically pure isomer 1) were initially charged in ethanol (127 ml), and 2 N aqueous hydrogen chloride solution (10.0 ml) was added. Under argon, 363 mg of palladium on carbon (10%) and 181 mg of palladium hydroxide on carbon (20%) were added, and the mixture was then stirred under an atmosphere of hydrogen at standard pressure overnight. The reaction solution was filtered through kieselguhr and the filter residue was washed with ethanol. The filtrate was concentrated under reduced pressure and the desired product was dried under high vacuum. Yield: 2.35 g (quant.).

MS (Method 1C): m/z=116 [M+H−HCl]$^+$;

$^1$H-NMR (400 MHz, DMSO-d$_6$): δ [ppm]=9.80-9.34 (br. M., 2H), 3.94-3.71 (m, 2H), 3.48-3.38 (m, 1H), 3.23-3.11 (d, 2H), 2.66 (br. q., 1H), 1.15 (d, 3H), 1.11 (d, 3H).

Example 26A (5R)-2,5-Dimethylmorpholine hydrochloride [enantiomerically pure isomer 2]

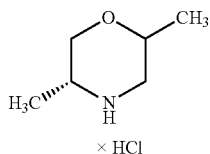

9.00 g (43.8 mmol) of (5R)-4-benzyl-2,5-dimethylmorpholine (Example 24A, enantiomerically pure isomer 2) were initially charged in ethanol (441 ml), and 2 N aqueous hydrogen chloride solution (40.0 ml) was added. Under argon, 1.26 g of palladium on carbon (10%) and 628 mg of palladium hydroxide on carbon (20%) were added, and the mixture was then stirred under an atmosphere of hydrogen at standard pressure overnight. The reaction solution was filtered through kieselguhr and the filter residue was washed with ethanol. The filtrate was concentrated under reduced pressure and the product was dried under high vacuum. Yield: 7.83 g (quant.).

MS (Method 1C): m/z=116 [M+H−HCl]$^+$;

$^1$H-NMR (400 MHz, DMSO-d$_6$): δ [ppm]=9.97 (br. s., 1H), 9.43 (br. s., 1H), 3.90-3.71 (m, 2H), 3.62 (d, 1H), 3.40 (d, 1H), 3.06-2.91 (m, 1H), 2.89-2.71 (m, 1H), 1.32 (d, 3H), 1.14 (d, 3H).

Example 27A (5R)-2-Allyl-4-benzyl-2,5-dimethylmorpholin-3-one [diastereomer mixture, 2 isomers]

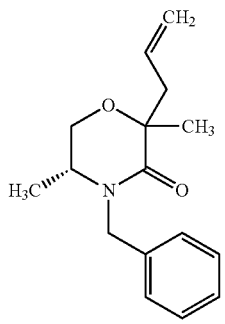 [SMILES: C=CCC1(C)OC[C@@H](C)N(Cc2ccccc2)C1=O]

22.8 g (104 mmol) of (5R)-4-benzyl-2,5-dimethylmorpholin-3-one [diastereomer mixture, 2 isomers] were initially charged in tetrahydrofuran (1.34 l), 146 ml (146 mmol) of 1 M lithium hexamethyldisilazide solution in tetrahydrofuran were added under argon and at −78° C. and the mixture was stirred for 15 min. At −78° C., 21.0 g (11.4 ml, 125 mmol) of allyl iodide were then added, and the reaction mixture was allowed to warm to RT and stirred for 3 h. The reaction was terminated by addition of saturated aqueous ammonium chloride solution, and the mixture was then extracted with ethyl acetate. The organic phase was washed with saturated aqueous sodium chloride solution, dried over sodium sulphate, filtered and concentrated under reduced pressure. The crude product was used for the next step without further purification. Yield: 27.5 g (77% of theory, purity: 75%).

LC-MS (Method 1A): R$_t$=0.99 min; MS (ESIpos): m/z=260 [M+H]$^+$.

Example 28A

[(5R)-4-Benzyl-2,5-dimethyl-3-oxomorpholin-2-yl]acetaldehyde [diastereomer mixture, 2 isomers]

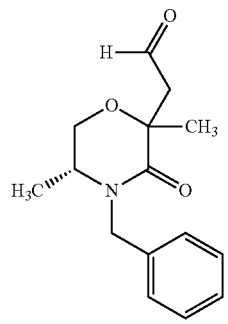 [SMILES: C[C@@H]1COC(C)(CC=O)C(=O)N1Cc1ccccc1]

27.4 g (79.9 mmol, purity: 75%) of (5R)-2-allyl-4-benzyl-2,5-dimethylmorpholin-3-one [diastereomer mixture, 2 isomers] were initially charged in tetrahydrofuran (620 ml) and water (370 ml), and 4.35 ml (1.60 mmol) of a 2.5% solution of osmium tetroxide in tert-butanol and 51.2 g (240 mmol) of sodium periodate were added at 0° C. The reaction solution was allowed to warm to RT and was stirred overnight. The reaction solution was filtered through kieselguhr and the filter residue was washed with tetrahydrofuran. The filtrate was concentrated under reduced pressure and the residue was taken up in ethyl acetate and water. After separation of the phases, the organic phase was washed with 1 N aqueous sodium sulphite solution (2×400 ml), dried over sodium sulphate, filtered and concentrated under reduced pressure. The crude product was used for the next step without further purification. Yield: 23.6 g of crude product.

LC-MS (Method 1A): R$_t$=0.81 min (diastereomer 1), R$_t$=0.84 min (diastereomer 2);

MS (ESIpos): m/z=262 [M+H]$^+$.

Example 29A (5R)-4-Benzyl-2-(2-hydroxyethyl)-2,5-dimethylmorpholin-3-one [diastereomer mixture, 2 isomers]

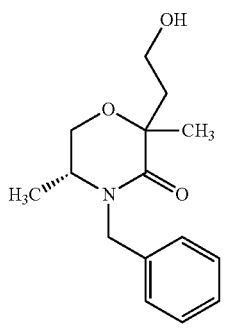 [SMILES: C[C@@H]1COC(C)(CCO)C(=O)N1Cc1ccccc1]

7.00 g (about 26.8 mmol, crude product) of [(5R)-4-benzyl-2,5-dimethyl-3-oxomorpholin-2-yl]acetaldehyde [diastereomer mixture, 2 isomers] were initially charged in methanol (200 ml), and 3.04 g (80.4 mmol) of sodium borohydride were added at 0° C. The reaction solution was allowed to warm to RT and stirred for 30 min. Water was then added to the reaction solution, most of the methanol was removed under reduced pressure and the residue was extracted with ethyl acetate. The organic phase was dried over sodium sulphate, filtered and concentrated under reduced pressure. The crude product was purified by preparative RP-HPLC (acetonitrile/water). Yield: 6.82 g (70% of theory, purity: 73%).

LC-MS (Method 1A): $R_t$=0.71 min; MS (ESIpos): m/z=264 [M+H]$^+$.

Example 30A

2-[(5R)-4-Benzyl-2,5-dimethylmorpholin-2-yl]ethanol [enantiomerically pure isomers 1+2]

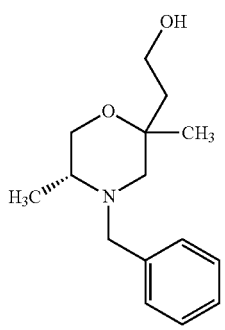 [SMILES: C[C@@H]1COC(C)(CCO)CN1Cc1ccccc1]

6.80 g (18.9 mmol, purity: 73%) of (5R)-4-benzyl-2-(2-hydroxyethyl)-2,5-dimethylmorpholin-3-one [diastereomer mixture, 2 isomers] were initially charged in tetrahydrofuran (191 ml), 37.7 ml (75.4 mmol) of 2 M borane/dimethyl sulphide complex solution in tetrahydrofuran were added under argon and the mixture was stirred under reflux for 2 h. The mixture was subsequently cooled to 0° C., methanol (37 ml) was added carefully and the mixture was stirred under reflux for 30 min. The mixture was concentrated completely under reduced pressure, and the residue was taken up in acetonitrile and subjected directly to purification and diastereomer separation by preparative RP-HPLC (acetonitrile/water, isocratic). Enantiomerically pure isomer 1 was the first compound eluted. Yield: 1.34 g (28% of theory, enantiomerically pure isomer 1). Enantiomerically pure isomer 2 was the second compound eluted. Yield: 2.28 g (47% of theory, enantiomerically pure isomer 2).

Enantiomerically Pure Isomer 1:
LC-MS (Method 4A): $R_t$=2.55 min; MS (ESIpos): m/z=250 [M+H]$^+$;

Enantiomerically Pure Isomer 2:
LC-MS (Method 4A): $R_t$=2.64 min; MS (ESIpos): m/z=250 [M+H]$^+$.

Example 31A

2-[(5R)-2,5-Dimethylmorpholin-2-yl]ethanol [enantiomerically pure isomer]

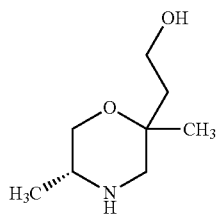

2.25 g (9.02 mmol) of 2-[(5R)-4-benzyl-2,5-dimethylmorpholin-2-yl]ethanol [enantiomerically pure isomer 2] from Example 30A were initially charged in ethanol (90.7 ml), 227 mg of palladium on carbon (10%) and 113 mg of palladium hydroxide on carbon (20%) were added under argon and the mixture was stirred under an atmosphere of hydrogen at standard pressure overnight. The reaction solution was filtered through kieselguhr and the filter residue was washed with ethanol. The filtrate was concentrated under reduced pressure and the product was dried under high vacuum. Yield: 1.46 g (quant.).

MS (Method 1C): m/z=160 [M+H]$^+$;

$^1$H-NMR (400 MHz, DMSO-d$_6$): δ [ppm]=4.21 (t, 1H), 3.53-3.44 (d, 2H), 3.34 (dd, 1H), 3.14 (t, 1H), 2.65-2.52 (m, 3H), 2.07 (br. s., 1H), 1.52 (td, 2H), 1.18 (s, 3H), 0.85 (d, 3H).

Example 32A (5R)-4-Benzyl-2-(2-hydroxypropyl)-2,5-dimethylmorpholin-3-one [diastereomer mixture, 4 isomers]

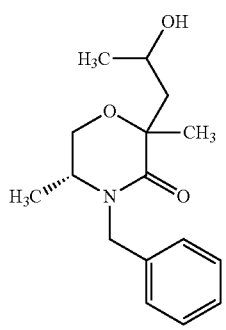 [SMILES: CC(O)CC1(C)OC[C@@H](C)N(Cc2ccccc2)C1=O]

16.8 g (about 64.3 mmol, crude product) of [(5R)-4-benzyl-2,5-dimethyl-3-oxomorpholin-2-yl]acetaldehyde [Example 28A, diastereomer mixture, 2 isomers] were initially charged in tetrahydrofuran (275 ml), and 77.2 ml (77.2 mmol) of a 1 M solution of methylmagnesium bromide in tetrahydrofuran were added at −78° C. The reaction solution was stirred at −78° C. for 15 min and then allowed to warm to RT. Saturated aqueous ammonium chloride solution (400 ml) was then added carefully to the reaction solution, most of the tetrahydrofuran was removed under reduced pressure and the residue was taken up in dichloromethane. After separation of the phases, the organic phase was washed with water, dried over sodium sulphate, filtered and concentrated under reduced pressure. The crude product was used for the next step without further purification. Yield: 16.2 g of crude product.

LC-MS (Method 1A): $R_t$=0.78, 0.80 min; MS (ESIpos): m/z=278 [M+H]$^+$.

Example 33A

1-[(5R)-4-Benzyl-2,5-dimethylmorpholin-2-yl]propan-2-ol [enantiomerically pure isomers 1+2+3+4]

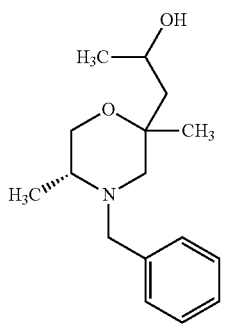 [SMILES: CC(O)CC1(C)CN(Cc2ccccc2)[C@H](C)CO1]

16.2 g (about 39.1 mmol, crude product) of (5R)-4-benzyl-2-(2-hydroxypropyl)-2,5-dimethylmorpholin-3-one [diastereomer mixture, 4 isomers] were initially charged in tetrahydrofuran (397 ml), 78.3 ml (157 mmol) of 2 M borane/dimethyl sulphide complex solution in tetrahydrofuran were added under argon and the mixture was stirred under reflux for 2 h. The mixture was subsequently cooled to 0° C., methanol (80 ml) was added carefully and the mixture was stirred under reflux for 30 min. The mixture was subsequently concentrated completely under reduced pressure, and the residue was taken up in acetonitrile and subjected directly to purification and diastereomer separation by preparative RP-HPLC (acetonitrile/water, isocratic). Here, the target compound eluted as third component. Yield: Target compound: 3.11 g (29% of theory; enantiomerically pure isomer 3); enantiomerically pure isomer 1: 2.12 g (20% of theory), enantiomerically pure isomer 2: 506 mg (5% of theory), enantiomerically pure isomer 4: 1.72 g (16% of theory).

Enantiomerically Pure Isomer 3:
LC-MS (Method 1A): $R_t$=0.39 min; MS (ESIpos): m/z=264 [M+H]$^+$;
$^1$H-NMR (400 MHz, DMSO-$d_6$): δ [ppm]=7.34-7.18 (m, 5H), 4.10 (d, 1H), 3.96 (d, 1H), 3.79 (m$_c$, 1H), 3.48 (dd, 1H), 3.36 (m$_c$, 1H), 3.04 (d, 1H), 2.46 (d, 1H), 2.28 (m$_c$, 1H), 1.88 (d, 1H), 1.44 (dd, 1H), 1.36 (dd, 1H), 1.23 (s, 3H), 1.01 (d, 3H), 0.98 (d, 3H).

Enantiomerically Pure Isomer 1:
LC-MS (Method 1A): $R_t$=0.43 min; MS (ESIpos): m/z=264 [M+H]$^+$;
$^1$H-NMR (400 MHz, DMSO-$d_6$): δ [ppm]=7.33-7.18 (m, 5H), 4.16 (d, 1H), 3.90 (d, 1H), 3.76 (m$_c$, 1H), 3.50 (dd, 1H), 3.26 (dd, 1H), 3.10 (d, 1H), 2.43 (d, 1H), 2.32 (m$_c$, 1H), 2.10 (dd, 1H), 1.84 (d, 1H), 1.27 (dd, 1H), 1.09-1.06 (m, 6H), 0.98 (d, 3H).

Enantiomerically Pure Isomer 2:
LC-MS (Method 1A): $R_t$=0.45 min; MS (ESIpos): m/z=264 [M+H]$^+$;
$^1$H-NMR (400 MHz, DMSO-$d_6$): δ [ppm]=7.32-7.20 (m, 5H), 4.11 (d, 1H), 3.92 (d, 1H), 3.57 (m$_c$, 1H), 3.51 (dd, 1H), 3.41 (dd, 1H), 3.06 (d, 1H), 2.47 (d, 1H), 2.34 (m$_c$, 1H), 1.85-1.74 (m, 2H), 1.59 (dd, 1H), 1.06 (s, 3H), 1.03-0.97 (t, 6H).

Enantiomerically Pure Isomer 4:
LC-MS (Method 1A): $R_t$=0.44 min; MS (ESIpos): m/z=264 [M+H]$^+$;
$^1$H-NMR (400 MHz, DMSO-$d_6$): δ [ppm]=7.49 (s, 5H), 4.69 (d, 1H), 4.28-4.15 (m, 2H), 3.86-3.73 (m, 3H), 3.63 (t, 1H), 3.32 (t, 1H), 3.21 (br. s., 1H), 2.84 (d, 1H), 1.52-1.38 (m, 4H), 1.28 (s, 3H), 1.01 (d, 3H).

Example 34A

1-[(5R)-2,5-Dimethylmorpholin-2-yl]propan-2-ol [enantiomerically pure isomer]

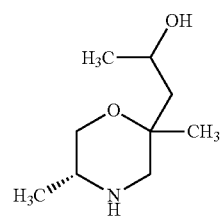

3.10 g (11.8 mmol) of 1-[(5R)-4-benzyl-2,5-dimethylmorpholin-2-yl]propan-2-ol [Example 33A, enantiomerically pure isomer 3] were initially charged in ethanol (118 ml), 296 mg of palladium on carbon (10%) and 148 mg of palladium hydroxide on carbon (20%) were added under argon and the mixture was stirred under an atmosphere of hydrogen at standard pressure overnight. The reaction solution was filtered through kieselguhr and the filter residue was washed with hot ethanol (100 ml). The filtrate was concentrated under reduced pressure and the product was dried under high vacuum. Yield: 2.06 g (quant.).

GC-MS (Method 1B): $R_t$=3.86 min; MS (EIpos): m/z=173 [M]$^+$;
$^1$H-NMR (400 MHz, DMSO-$d_6$): δ [ppm]=4.20 (d, 1H), 3.87 (br. s., 1H), 3.35 (dd, 1H), 3.16 (t, 1H), 2.67-2.53 (m, 3H), 2.05 (br. s., 1H), 1.44 (dd, 1H), 1.36 (dd, 1H), 1.23 (s, 3H), 1.04 (d, 3H), 0.85 (d, 3H).

Example 35A

N-Benzyl-2-chloro-N-(1,4-dihydroxybutan-2-yl) propanamide [diastereomer mixture, 4 isomers]

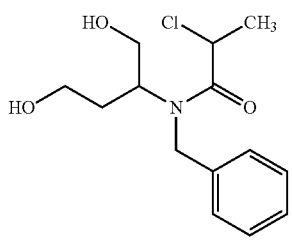 [SMILES: CC(Cl)C(=O)N(Cc1ccccc1)C(CO)CCO]

20.6 g (106 mmol) of 2-(benzylamino)butane-1,4-diol [racemate] [lit.: B. L. Feringa, B. de Lange, *Heterocycles* 1988, 27, 1197-1205] were initially charged in isopropanol (500 ml), the mixture was cooled to 0° C. and 21.4 g (29.4 ml, 211 mmol) of triethylamine were added. 16.1 g (12.6 ml, 127 mmol) of 2-chloropropionyl chloride [racemate] were then added dropwise. After 30 min of stirring, a further 10.4 g (8.37 ml, 84.4 mmol) of 2-chloropropionyl chloride [racemate] were added dropwise, and the reaction solution was allowed to warm to RT and then concentrated under reduced pressure. The residue was taken up in ethyl acetate (500 ml) and washed with 0.5 N aqueous hydrogen chloride solution (400 ml). The aqueous phase was extracted repeatedly with ethyl acetate. The organic phases were dried over sodium sulphate, filtered and concentrated under reduced pressure. The crude product was used for the next step without further purification. Yield: 37.5 g (78% of theory, purity: 63%, diastereomer ratio about 2:1).

LC-MS (Method 1A): $R_t$=0.71 min (diastereomer 1, 2 isomers), $R_t$=0.72 min (diastereomer 2, 2 isomers);
MS (ESIpos): m/z=286 [M+H]$^+$.

Example 36A

4-Benzyl-5-(2-hydroxyethyl)-2-methylmorpholin-3-one [diastereomer mixture, 4 isomers]

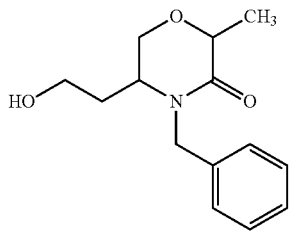

37.5 g (82.5 mmol, purity: 63%) of N-benzyl-2-chloro-N-(1,4-dihydroxybutan-2-yl)propanamide [diastereomer mixture, 4 isomers] were initially charged in isopropanol (500 ml), and the mixture was cooled to 0° C. 73.5 g (655 mmol) of potassium tert-butoxide were then added in one portion, and the mixture was stirred at 0° C. for 1 h. Most of the isopropanol was removed under reduced pressure, and the residue was taken up in ethyl acetate and washed with 1 N aqueous hydrogen chloride solution (400 ml). The organic phase was dried over sodium sulphate, filtered and concentrated under reduced pressure. The crude product was used for the next step without further purification. Yield: 28.8 g (quant., purity: 82%, diastereomer ratio about 2.5:1).

LC-MS (Method 7A): $R_t$=1.42 min (diastereomer 1, 2 isomers), $R_t$=1.46 min (diastereomer 2, 2 isomers);
MS (ESIpos): m/z=250 [M+H]$^+$.

Example 37A 2-(4-Benzyl-6-methylmorpholin-3-yl)ethanol [racemate]

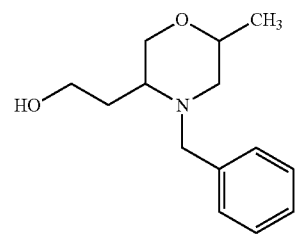 [SMILES: CC1CN(Cc2ccccc2)C(CCO)CO1]

28.8 g (94.7 mmol, purity: 82%) of 4-benzyl-5-(2-hydroxyethyl)-2-methylmorpholin-3-one [diastereomer mixture, 4 isomers] were initially charged in tetrahydrofuran (800 ml), 231 ml (462 mmol) of 2 M borane/dimethyl sulphide complex solution in tetrahydrofuran were added under argon and the mixture was then stirred under reflux for 2 h. The mixture was subsequently cooled to 0° C., methanol (220 ml) was added carefully and the mixture was stirred under reflux for 30 min. The mixture was subsequently concentrated completely under reduced pressure, and 6.0 g of the residue were taken up in acetonitrile and subjected to purification and diastereomer separation by preparative RP-HPLC (acetonitrile/water, isocratic). Here, the target compound eluted as second component (diastereomer 2, 2 isomers). Yield: Diastereomer 2 (2 isomer): 1.95 g; Diastereomer 1 (2 isomer): 698 mg Diastereomer 2 (2 Isomer):
LC-MS (Method 4A): $R_t$=2.33 min; MS (ESIpos): m/z=236 [M+H]$^+$.

Diastereomer 1 (2 Isomer):
LC-MS (Method 4A): $R_t$=2.23 min; MS (ESIpos): m/z=236 [M+H]$^+$.

Example 38A 2-(6-Methylmorpholin-3-yl)ethanol [racemate]

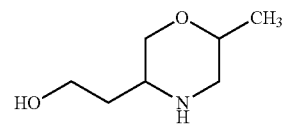

1.95 g (8.29 mmol) of 2-(4-benzyl-6-methylmorpholin-3-yl)ethanol [diastereomer 2, 2 isomers from Example 37A] were initially charged in ethanol (83 ml), 208 mg of palladium on carbon (10%) and 104 mg of palladium hydroxide on carbon (20%) were added under argon, and the mixture was then stirred under an atmosphere of hydrogen at standard pressure overnight. The reaction solution was filtered through kieselguhr and the filter residue was washed with ethanol. The filtrate was concentrated under reduced pressure and the product was dried under high vacuum. Yield: 1.37 g (quant.).

MS (Method 1C): m/z=146 [M+H]$^+$;

$^1$H-NMR (400 MHz, DMSO-d$_6$): δ [ppm]=3.53-3.41 (m, 5H), 2.69 (m$_c$, 1H), 2.60-2.43 (m, 2H), 1.82-1.69 (m, 1H), 1.58-1.44 (m, 1H), 1.03 (d, 3H), two protons not visible.

Example 39A

N-Benzyl-2-chloro-N-[(2S)-1,4-dihydroxybutan-2-yl]propanamide [diastereomer mixture, 2 isomers]

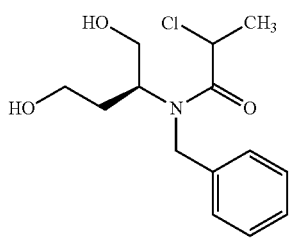 [SMILES: CC(Cl)C(=O)N(Cc1ccccc1)[C@H](CO)CCO]

45.1 g (199 mmol, purity: 86%) 2S)-2-(benzyl-amino)butane-1,4-diol [F. Horiuchi, M. Matsui, *Agr. Biol. Chem.* 1973, 37, 1713-1716] were initially charged in isopropanol (1.00 l), the mixture was cooled to 0° C. and 40.2 g (55.4 ml, 397 mmol) of triethylamine were added. 37.8 g (29.6 ml, 298 mmol) of 2-chloropropionyl chloride [racemate] were then added dropwise. After 30 min of stirring, a further 18.9 g (14.8 ml, 149 mmol) of 2-chloropropionyl chloride [racemate] were added dropwise, and the reaction solution was allowed to warm to RT and then concentrated under reduced pressure. The residue was taken up in ethyl acetate (1.00 l) and washed with water. The organic phase was dried over sodium sulphate, filtered and concentrated under reduced pressure. The crude product was used for the next step without further purification. Yield: 71.8 g (quant., purity: 82%, diastereomer ratio about 1:1).

LC-MS (Method 1A): R$_t$=0.65 min (enantiomerically pure isomer 1), R$_t$=0.67 min (enantiomerically pure isomer 2);

MS (ESIpos): m/z=286 [M+H]$^+$.

Example 40A (5S)-4-Benzyl-5-(2-hydroxyethyl)-2-methylmorpholin-3-one [diastereomer mixture, 2 isomers]

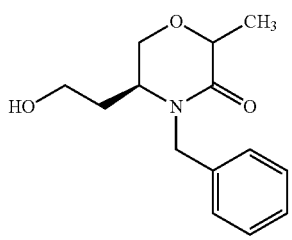 [SMILES: CC1OC[C@H](CCO)N(Cc2ccccc2)C1=O]

71.8 g (206 mmol, purity: 82%) of N-benzyl-2-chloro-N-[(2S)-1,4-dihydroxybutan-2-yl]propanamide [diastereomer mixture, 2 isomers] were initially charged in isopropanol (1.30 l), and the mixture was cooled to 0° C. 92.4 g (824 mmol) of potassium tert-butoxide were then added in one portion, and the mixture was stirred at 0° C. for 30 min. The reaction solution was allowed to warm to RT and the isopropanol was removed under reduced pressure. The residue was taken up in ethyl acetate (500 ml). Water (600 ml) was added, the mixture was extracted and, after phase separation, the aqueous phase was extracted with ethyl acetate (2×300 ml). The organic phases were dried over sodium sulphate, filtered and concentrated under reduced pressure. The crude product was used for the next step without further purification. Yield: 58.6 g (quant., purity: 90%, diastereomer ratio about 3:2).

LC-MS (Method 3A): R$_t$=1.51 min (enantiomerically pure isomer 1), R$_t$=1.53 min (enantiomerically pure isomer 2);

MS (ESIpos): m/z=250 [M+H]$^+$.

Example 41A

2-[(3S)-4-Benzyl-6-methylmorpholin-3-yl]ethanol [enantiomerically pure isomer]

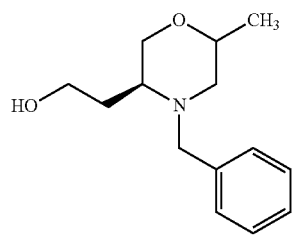 [SMILES: CC1CN(Cc2ccccc2)[C@@H](CCO)CO1]

30.0 g (108 mmol) of (5S)-4-benzyl-5-(2-hydroxyethyl)-2-methylmorpholin-3-one [diastereomer mixture, 2 isomers] were initially charged in tetrahydrofuran (1.10 l), 217 ml (433 mmol) of 2 M borane/dimethyl sulphide complex solution in tetrahydrofuran were added under argon and the mixture was stirred under reflux for 2 h. The mixture was subsequently cooled to 0° C., methanol (200 ml) was added carefully and the mixture was stirred under reflux for 30 min. The mixture was subsequently concentrated completely under reduced pressure, and the residue was taken up in acetonitrile and subjected to purification and diastereomer separation by preparative RP-HPLC (acetonitrile/water, isocratic). Here, the target compound eluted as second component (enantiomerically pure isomer 2). Yield: enantiomerically pure isomer 2: 12.1 g (47% of theory), enantiomerically pure isomer 1: 6.23 g (24% of theory).

Enantiomerically Pure Isomer 2:

LC-MS (Method 4A): R$_t$=2.33 min; MS (ESIpos): m/z=236 [M+H]$^+$;

$^1$H-NMR (400 MHz, DMSO-d$_6$): δ [ppm]=7.36-7.18 (m, 5H), 4.42 (t, 1H), 3.69-3.35 (m, 7H), 2.65-2.56 (m, 1H), 2.36-2.29 (m, 1H), 2.26-2.16 (m, 1H), 1.81-1.65 (m, 2H), 1.00 (d, 3H).

Enantiomerically Pure Isomer 1:

LC-MS (Method 4A): R$_t$=2.23 min; MS (ESIpos): m/z=236 [M+H]$^+$;

$^1$H-NMR (400 MHz, DMSO-d$_6$): δ [ppm]=7.37-7.19 (m, 5H), 4.49 (t, 1H), 4.10 (d, 1H), 3.76 (dd, 1H), 3.58-3.38 (m, 3H), 3.33-3.20 (m, 1H), 2.95 (d, 1H), 2.27 (m$_c$, 1H), 1.80 (m$_c$, 1H), 1.68 (dd, 1H), 1.48 (m$_c$, 1H), 0.94 (d, 3H).

Example 42A

2-[(3S)-6-Methylmorpholin-3-yl]ethanol [enantiomerically pure isomer]

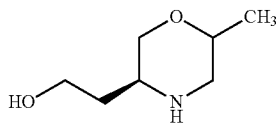

58.0 g (246 mmol) of 2-[(3S)-4-benzyl-6-methylmorpholin-3-yl]ethanol [enantiomerically pure isomer 2, Example 41A (the amount of substance used originates from several reactions analogously to Example 41A.)] were initially charged in ethanol (1.50 l), 2.90 g of palladium on carbon (10%) and 2.90 g of palladium hydroxide on carbon (20%) were added under argon and the mixture was then stirred under an atmosphere of hydrogen at standard pressure overnight. The reaction solution was filtered through kieselguhr and the filter residue was washed with hot ethanol (100 ml). The filtrate was concentrated under reduced pressure and the product was dried under high vacuum. Yield: 35.5 g (99% of theory).

Optical rotation: $[\alpha]_D^{19.5}$=89.7° (c=0.565, chloroform);
LC-MS (Method 5A): $R_t$=0.54 min; MS (ESIpos): m/z=146 $[M+H]^+$;
LC-MS (Method 1A): MS (ESIpos): m/z=146 $[M+H]^+$;
$^1$H-NMR (400 MHz, CDCl$_3$): δ [ppm]=3.88-3.80 (m, 2H), 3.71 (br. d., 1H), 3.63 (br. d., 1H), 3.50 (m$_c$, 1H), 3.12 (br. s., 2H), 2.94 (m$_c$, 1H), 2.81 (dd, 1H), 2.68 (dd, 1H), 2.39-2.25 (m, 1H), 1.45 (m$_c$, 1H), 1.15 (d, 3H).

Example 43A

Methyl [3-(benzyloxy)cyclobutylidene][(tert-butoxycarbonyl)amino]acetate

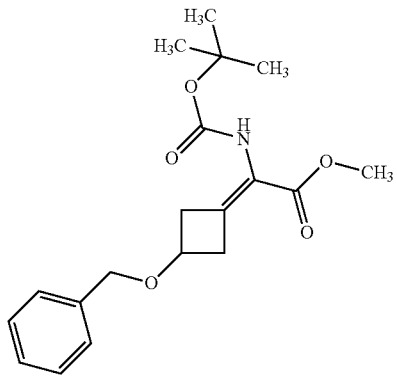 [SMILES: COC(=O)C(NC(=O)OC(C)(C)C)=C1CC(OCc2ccccc2)C1]

928 mg (3.12 mmol) of methyl [(tert-butoxycarbonyl)amino](dimethoxyphosphoryl)acetate [racemate] and 500 mg (2.84 mmol) of 3-(benzyloxy)cyclobutanone [K. Ogura, G. Tsuchihashi et al., *Bull. Chem. Soc. Jpn.* 1984, 57, 1637-1642] were initially charged in dichloromethane (50 ml), 605 mg (0.590 ml, 3.97) of 1,8-diazabicyclo[5.4.0]undec-7-ene were added at RT and the mixture was then stirred overnight. The reaction solution was concentrated under reduced pressure and the residue was taken up in ethyl acetate. The organic phase was washed with water, 0.5 N aqueous hydrogen chloride solution, saturated aqueous sodium bicarbonate solution and saturated aqueous sodium chloride solution, dried over sodium sulphate and filtered and concentrated under reduced pressure. The residue was purified by preparative RP-HPLC (acetonitrile/water). Yield: 651 mg (60% of theory).

LC-MS (Method 1A): $R_t$=1.15 min; MS (ESIpos): m/z=348 $[M+H]^+$;
$^1$H-NMR (400 MHz, DMSO-d$_6$): δ [ppm]=8.11 (br. s., 1H), 7.41-7.25 (m, 5H), 4.42 (s, 2H), 4.13 (quin, 1H), 3.63 (s, 3H), 3.25 (br. d., 1H), 2.99 (br. d., 1H), 2.85 (br. d., 1H), 2.65 (m, 1H), 1.37 (s, 9H).

Example 44A

Methyl [3-(benzyloxy)cyclobutyl][(tert-butoxycarbonyl)amino]acetate [cis and trans isomer mixture, 4 isomers]

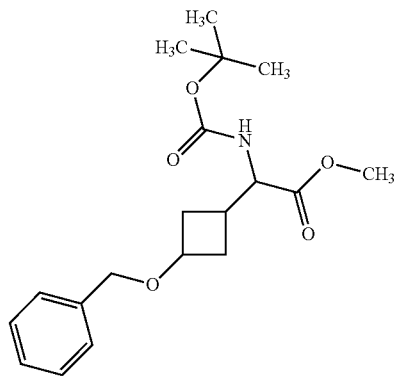 [SMILES: COC(=O)C(NC(=O)OC(C)(C)C)C1CC(OCc2ccccc2)C1]

650 mg (1.87 mmol) of methyl [3-(benzyloxy)cyclobutylidene][(tert-butoxycarbonyl)amino]acetate and 455 mg (18.7 mmol) of magnesium turnings were initially charged in methanol (50 ml) and reacted at RT in an ultrasonic bath [Elma, Transsonic T 780] for 3 h. Semisaturated aqueous ammonium chloride solution was added, and the reaction solution was extracted repeatedly with dichloromethane. The organic phases were dried over sodium sulphate, filtered and concentrated under reduced pressure. The crude product was used for the next step without further purification. Yield: 630 mg (96% of theory).

LC-MS (Method 1A): $R_t$=1.16 min; MS (ESIpos): m/z=350 $[M+H]^+$, 250 $[M+H-COOC(CH_3)_3]$;
$^1$H-NMR (400 MHz, DMSO-d$_6$): δ [ppm]=7.39-7.20 (m, 6H), 4.34 (s, 2H), 4.07 (quin, 0.3H), 3.99-3.73 (m, 1.7H), 3.60 (s, 3H), 2.34-1.94 (m, 3.5H), 1.74-1.59 (m, 1.5H), 1.45-1.27 (m, 9H).

Example 45A tert-Butyl {1-[3-(benzyloxy)cyclobutyl]-2-hydroxyethyl}carbamate [cis and trans isomer mixture, 4 isomers]

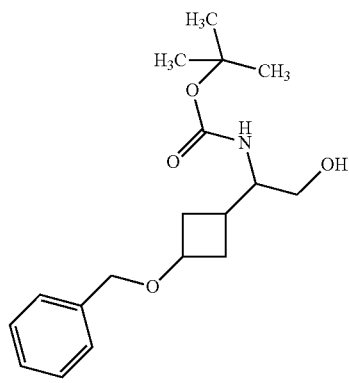 [SMILES: CC(C)(C)OC(=O)NC(CO)C1CC(OCc2ccccc2)C1]

620 mg (1.77 mmol) of methyl [3-(benzyloxy)cyclobutyl][(tert-butoxycarbonyl)amino]acetate [cis and trans isomer mixture, 4 isomers] were initially charged in tetrahydrofuran (6.0 ml), and 4.44 ml (8.87 mmol) of 2 M lithium borohydride solution in tetrahydrofuran were added at 0° C. The mixture was then stirred for 4 h and allowed to warm to RT during this time. The reaction was terminated by addition of ethyl acetate (50.0 ml) and the reaction solution was subsequently washed with 0.5 N aqueous hydrogen chloride solution. The organic phase was dried over sodium sulphate, filtered and concentrated under reduced pressure. The crude product was used for the next step without further purification. Yield: 560 mg (96% of theory).

LC-MS (Method 1A): $R_t$=0.99 min; MS (ESIpos): m/z=322 [M+H]$^+$, 222 [M+H−Boc];

$^1$H-NMR (400 MHz, DMSO-d$_6$): δ [ppm]=7.47-7.15 (m, 5H), 6.65-6.41 (m, 1H), 4.46 (br. s., 0.5H), 4.33 (s, 2H), 3.88-3.70 (m, 0.7H), 3.67-3.09 (m, 3.8H), 2.36-1.78 (m, 3.5H), 1.74-1.48 (m, 1.5H), 1.38 (s, 9H).

Example 46A

2-Amino-2-[3-(benzyloxy)cyclobutyl]ethanol trifluoroacetate [cis and trans isomer mixture, 4 isomers]

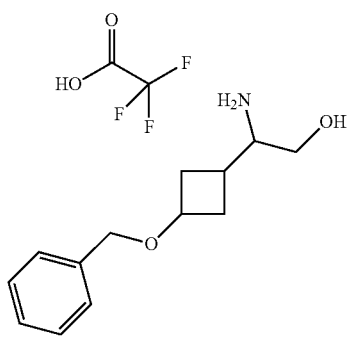

560 mg (1.74 mmol) of tert-butyl {1-[3-(benzyloxy)cyclobutyl]-2-hydroxyethyl}carbamate [cis and trans isomer mixture, 4 isomers] were initially charged in dichloromethane (8.0 ml), 1.0 ml (12.9 mmol) of trifluoroacetic acid was added at RT and the mixture was stirred for 2 h. The reaction solution was then concentrated completely under reduced pressure and excess trifluoroacetic acid was removed by repeated coevaporation with dichloromethane. The crude product was used for the next step without further purification. Yield: 580 mg (95% of theory).

LC-MS (Method 4A): $R_t$=2.10 min; MS (ESIpos): m/z=222 [M+H−TFA]$^+$.

Example 47A

N-{1-[3-(Benzyloxy)cyclobutyl]-2-hydroxyethyl}-2-chloropropanamide [diastereomer mixture, 8 isomers]

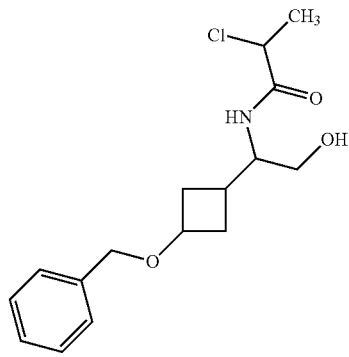 [SMILES: CC(Cl)C(=O)NC(CO)C1CC(OCc2ccccc2)C1]

580 mg (1.73 mmol) of 2-amino-2-[3-(benzyloxy)cyclobutyl]ethanol trifluoroacetate [cis and trans isomer mixture, 4 isomers] were initially charged in isopropanol (15 ml), the mixture was cooled to 0° C. and 700 mg (960 µl, 6.92 mmol) of triethylamine were added. 242 mg (190 µl, 1.90 mmol) of 2-chloropropionyl chloride [racemate] were then added dropwise, and the mixture was stirred at 0° C. for 1 h and then concentrated completely under reduced pressure. 0.5 N aqueous hydrogen chloride solution (50 ml) was added to the residue, and the mixture was extracted repeatedly with dichloromethane. The organic phases were dried over sodium sulphate, filtered and concentrated under reduced pressure. The crude product was used for the next step without further purification. Yield: 638 mg (91% of theory, purity 77%).

LC-MS (Method 4A): $R_t$=2.36 min; MS (ESIpos): m/z=312 [M+H]$^+$.

Example 48A

5-[3-(Benzyloxy)cyclobutyl]-2-methylmorpholin-3-one [diastereomer mixture, 8 isomers]

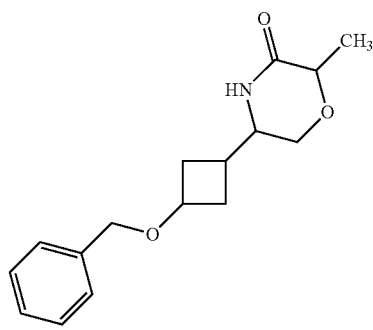 [SMILES: CC1OCC(C2CC(OCc3ccccc3)C2)NC1=O]

1.15 g (3.69 mmol) of N-{1-[3-(benzyloxy)cyclobutyl]-2-hydroxyethyl}-2-chloropropanamide [diastereomer mixture, 8 isomers] were initially charged in isopropanol (30.0 ml), the mixture was cooled to 0° C. and 1.66 g (14.8 mmol) of potassium tert-butoxide were then added in one portion. The mixture was allowed to warm to RT and then stirred at 50° C. for 1 h. Most of the isopropanol was removed under reduced pressure and the residue was taken up in ethyl acetate. The organic phase was washed with 1 N aqueous hydrogen chloride solution, dried over sodium sulphate, filtered and concentrated under reduced pressure. The residue was purified by preparative RP-HPLC (acetonitrile/water).

Yield: 953 mg (93% of theory).

LC-MS (Method 1A): $R_t$=0.88 min; MS (ESIpos): m/z=276 $[M+H]^+$;

$^1$H-NMR (400 MHz, CDCl$_3$): δ [ppm]=7.43-7.27 (m, 5H), 6.40 (br. s., 0.16H), 6.24 (br. s., 0.38H), 6.12-5.94 (m, 0.46H), 4.41 (s, 2H), 4.24-4.05 (m, 1.25H), 4.03-3.86 (m, 1.25H), 3.82-3.51 (m, 1.5H), 3.31-3.21 (m, 1H), 2.54-1.57 (m, 5H), 1.48-1.41 (m, 3H).

Example 49A

5-[3-(Benzyloxy)cyclobutyl]-2-methylmorpholine [diastereomer mixture, 8 isomers]

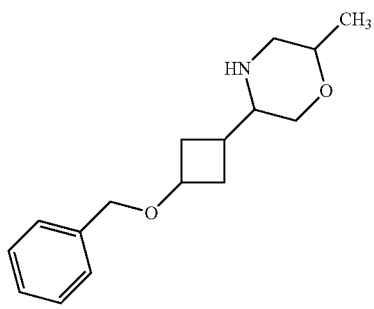 [SMILES: CC1CNC(C2CC(OCc3ccccc3)C2)CO1]

953 mg (3.46 mmol) of 5-[3-(benzyloxy)cyclobutyl]-2-methylmorpholin-3-one [diastereomer mixture, 8 isomers] were initially charged in tetrahydrofuran (10 ml), 6.92 ml (13.8 mmol) of 2 M borane/dimethyl sulphide complex solution in tetrahydrofuran were added under argon and the mixture was stirred under reflux for 3 h. The reaction solution was then carefully added dropwise to ethanol (50.0 ml) and stirred under reflux for 8 h. The mixture was then concentrated under reduced pressure, and the residue was taken up in acetonitrile and purified by preparative RP-HPLC (acetonitrile/water). Yield: 780 mg (84% of theory).

LC-MS (Method 1A): $R_t$=0.57, 0.60 min; MS (ESIpos): m/z=262 $[M+H]^+$;

$^1$H-NMR (400 MHz, DMSO-d$_6$): δ [ppm]=7.39-7.24 (m, 5H), 4.37-4.31 (m, 2H), 4.11-3.98 (m, 0.3H), 3.92-3.78 (m, 0.7H), 3.72-3.54 (m, 0.5H), 3.50-3.40 (m, 1.5H), 2.94-2.70 (m, 1H), 2.61 (td, 0.3H), 2.48-1.82 (m, 5.7H), 1.73-1.40 (m, 2H), 1.06-0.94 (m, 3H), one proton obscured.

Example 50A

Benzyl 5-[3-(benzyloxy)cyclobutyl]-2-methylmorpholine-4-carboxylate [diastereomer mixture, 4 isomers]

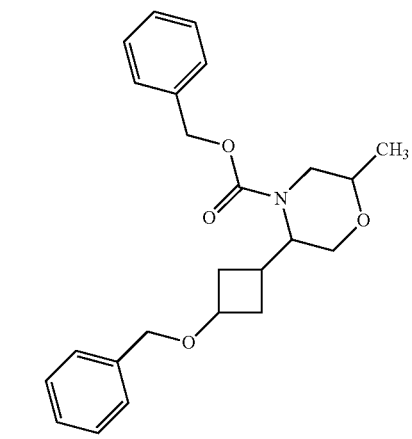 [SMILES: CC1CN(C(=O)OCc2ccccc2)C(C2CC(OCc3ccccc3)C2)CO1]

900 mg (3.44 mmol) of 5-[3-(benzyloxy)cyclobutyl]-2-methylmorpholine [diastereomer mixture, 8 isomers] and 890 mg (1.20 ml, 6.89 mmol) of N,N-diisopropylethylamine were initially charged in dichloromethane (45.0 ml), 881 mg (0.74 ml, 5.17 mmol) of benzyl chloroformate were added dropwise at 0° C. and the mixture was stirred overnight and allowed to warm to RT during this time. The reaction solution was concentrated under reduced pressure and the residue was taken up in acetonitrile. Purification and diastereomer separation by RP-HPLC on an achiral phase (acetonitrile/water) gave 537 mg (36% of theory) of the target compound of Example 50A (diastereomer mixture, 4 isomers) and 588 mg (43% of theory) of the target compound of Example 51A (diastereomer mixture, 4 isomers).

LC-MS (Method 1A): $R_t$=1.26 min; MS (ESIpos): m/z=396 $[M+H]^+$;

$^1$H-NMR (400 MHz, DMSO-d$_6$): δ [ppm]=7.41-7.24 (m, 10H), 5.22-5.01 (m, 2H), 4.33-4.26 (m, 2H), 4.09-3.66 (m, 4H), 3.51 (d, 1H), 3.29-3.10 (m, 2H), 2.82 (br. s., 0.3H), 2.48-1.79 (m, 3.3H), 1.69-1.52 (m, 1.4H), 1.14-1.07 (m, 3H).

Example 51A

Benzyl 5-[3-(benzyloxy)cyclobutyl]-2-methylmorpholine-4-carboxylate [diastereomer mixture, 4 isomers]

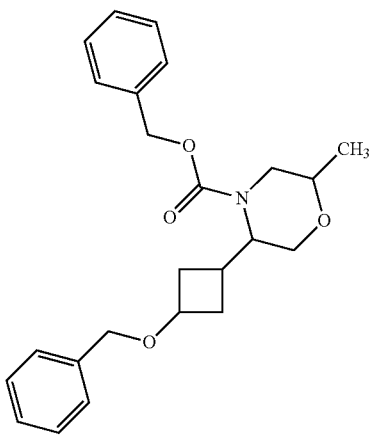 [SMILES: CC1CN(C(=O)OCc2ccccc2)C(C2CC(OCc3ccccc3)C2)CO1]

900 mg (3.44 mmol) of 5-[3-(benzyloxy)cyclobutyl]-2-methylmorpholine [diastereomer mixture, 8 isomers] and 890 mg (1.20 ml, 6.89 mmol) of N,N-diisopropylethylamine were initially charged in dichloromethane (45.0 ml), 881 mg (0.74 ml, 5.17 mmol) of benzyl chloroformate were added dropwise at 0° C. and the mixture was stirred overnight and allowed to warm to RT during this time. The reaction solution was concentrated under reduced pressure and the residue was taken up in acetonitrile. Purification and diastereomer separation by RP-HPLC on an achiral phase (acetonitrile/water) gave 537 mg (36% of theory) of the target compound of Example 50A (diastereomer mixture, 4 isomers) and 588 mg (43% of theory) of the target compound of Example 51A (diastereomer mixture, 4 isomers).

LC-MS (Method 1A): $R_t$=1.29 min; MS (ESIpos): m/z=396 [M+H]$^+$;

$^1$H-NMR (400 MHz, DMSO-$d_6$): δ [ppm]=7.44-7.22 (m, 10H), 5.20-4.98 (m, 2H), 4.36-4.20 (m, 2H), 4.14-3.34 (m, 6H), 2.88-2.57 (m, 1.5H), 2.44-1.53 (m, 4.5H), 1.10-1.03 (m, 3H).

Example 52A 3-(6-Methylmorpholin-3-yl)cyclobutanol [diastereomer mixture, 4 isomers]

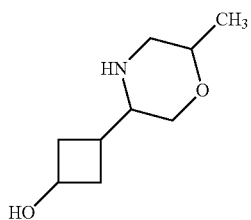

580 mg (1.47 mmol) of benzyl 5-[3-(benzyloxy)cyclobutyl]-2-methylmorpholin-4-carboxylate [Example 51A, diastereomer mixture, 4 isomers] were initially charged in ethanol (100 ml), 58 mg of palladium on carbon (10%) and 58 mg of palladium hydroxide on carbon (20%) were added under argon and the mixture was stirred under an atmosphere of hydrogen at standard pressure overnight. The reaction solution was filtered through kieselguhr and the filter residue was washed with ethanol. The filtrate was concentrated under reduced pressure and the product was dried under high vacuum. Yield: 245 mg (97% of theory).

GC-MS (Method 1B): $R_t$=4.60, 4.67 min; MS (EIpos): m/z=171 [M]$^+$;

$^1$H-NMR (400 MHz, DMSO-$d_6$): δ [ppm]=4.94-4.84 (m, 1H), 4.16-4.05 (d, 0.6H), 3.93-3.82 (m, 0.7H), 3.55-3.40 (m, 3.3H), 3.19-3.14 (m, 0.7H), 3.17 (d, 1H), 2.47-1.76 (m, 6H), 1.58-1.28 (m, 1.5H), 1.08-0.94 (m, 3.5H).

Example 53A

[1-Amino-3-(benzyloxy)cyclobutyl]methanol [diastereomer mixture, 2 isomers, cis/trans about 4:1]

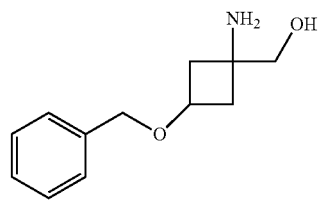 [SMILES: NC1(CO)CC(OCc2ccccc2)C1]

I) 5.00 g (20.3 mmol) of 2-(benzyloxy)-5,7-diazaspiro[3.4]octane-6,8-dione [diastereomer mixture, 2 isomers, cis/trans about 4:1; T. M. Shoup, M. M. Goodman, *J. Labelled. Cpd. Radiopharm.* 1999, 42, 215-225; US2006/292073 A1] were initially charged in water (100 ml), and 32.0 g (102 mmol) of barium hydroxide octahydrate were added. In seven portions, the suspension was stirred in the microwave (Biotage Synthesizer), in each case for 1.5 h at 140° C. The suspensions were combined and adjusted to a pH of about 4 using a 6 N aqueous sulphuric acid solution. The precipitated solid was filtered off under reduced pressure, the filtrate was then concentrated under reduced pressure and the solid obtained was dried under high vacuum. This gave 6.2 g of crude product.

II) 21.3 g (24.9 ml, 196 mmol) of chlorotrimethylsilane were added dropwise to 49.1 ml of a 2 M solution of lithium borohydride in tetrahydrofuran (98.2 mmol). The suspension obtained was cooled to 0° C., and 5.43 g of the crude product from I) were then added a little at a time. The mixture was then warmed to RT and stirred at RT overnight. The reaction was terminated by dropwise addition of methanol (15 ml) and the reaction solution was then concentrated under reduced pressure. The residue was taken up in ethyl acetate and washed with an aqueous 2 N sodium hydroxide solution. The aqueous phase was extracted with ethyl acetate, and the combined organic phases were dried over sodium sulphate, filtered and concentrated under reduced pressure. The crude product was used for the next step without further purification. Yield: 3.76 g (crude product).

LC-MS (Method 4A): $R_t$=2.10 min; MS (ESIpos): m/z=208 [M+H]$^+$;

$^1$H-NMR (400 MHz, DMSO-$d_6$): δ [ppm]=7.39-7.22 (m, 5H), 4.66 (br. s., 1H), 4.32 (s, 2H), 4.15 (quin, 0.2H), 3.70 (quin, 0.8H), 3.22-3.14 (m, 2H), 2.34-2.26 (m, 2H), 1.91-1.74 (m, 2H), 1.72-1.61 (m, 2H).

Example 54A tert-Butyl [3-(benzyloxy)-1-(hydroxymethyl)cyclobutyl]carbamate [enantiomerically pure cis and trans isomer]

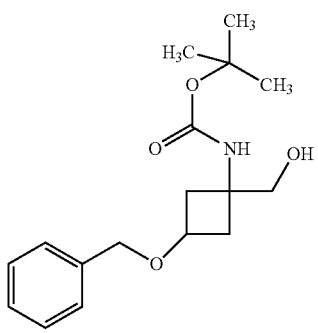 [SMILES: CC(C)(C)OC(=O)NC1(CO)CC(OCc2ccccc2)C1]

3.76 g (18.1 mmol) of [1-amino-3-(benzyloxy)cyclobutyl]methanol [diastereomer mixture, 2 isomers cis/trans about 4:1] were initially charged in dichloromethane (150 ml), 4.36 g (20.0 mmol) of di-tert-butyl dicarbonate and 3.86 g (5.31 ml, 38.1 mmol) of triethylamine were added at RT and the mixture was stirred at RT overnight. The mixture was then washed with 0.5 N aqueous hydrogen chloride solution, saturated aqueous sodium bicarbonate solution and water, and the organic phase was dried over sodium sulphate, filtered and concentrated under reduced pressure. The crude product (6.4 g) was purified by preparative RP-HPLC (Method 1G) and separated into the diastereomers. Here, the more rapidly eluting major diastereomer was the cis isomer, and the slower eluting minor diastereomer was the trans isomer. Yield: 3.45 g (61% of theory, enantiomerically pure cis isomer); 690 mg (12% of theory, enantiomerically pure trans isomer).

Enantiomerically Pure Cis Diastereomer:
LC-MS (Method 1A): $R_t$=2.00 min; MS (ESIpos): m/z=308 [M+H]$^+$;

Enantiomerically Pure Trans Diastereomer:
LC-MS (Method 1A): $R_t$=2.02 min; MS (ESIpos): m/z=308 [M+H]$^+$.

Example 55A

[cis-1-Amino-3-(benzyloxy)cyclobutyl]methanol hydrochloride [enantiomerically pure cis isomer]

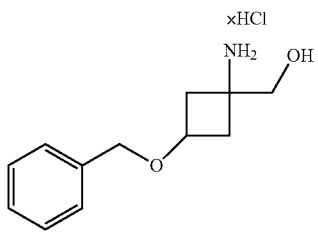 [SMILES: NC1(CO)CC(OCc2ccccc2)C1]

3.45 g (11.2 mmol) of tert-butyl [cis-3-(benzyloxy)-1-(hydroxymethyl)cyclobutyl]carbamate [enantiomerically pure cis isomer from Example 54A] were initially charged in 1,4-dioxane (30 ml), 11.2 ml of a 4 N solution of hydrogen chloride in 1,4-dioxane/water were added at RT and the mixture was stirred at RT for 20 h.

The mixture was then concentrated under reduced pressure and the residue was dried under high vacuum. The crude product was used for the next step without further purification.

Yield: 2.81 g (quant.).
LC-MS (Method 1A): $R_t$=0.40 min; MS (ESIpos): m/z=208 [M+H−HCl]$^+$;
$^1$H-NMR (400 MHz, DMSO-d$_6$): δ [ppm]=8.24 (br. s., 3H), 7.43-7.25 (m, 5H), 5.54 (br. s., 1H), 4.39 (s, 2H), 3.90 (quin, 1H), 3.46 (br. d., 2H), 2.42 (m$_c$, 2H), 2.12 (m$_c$, 2H).

Example 56A

N-[cis-3-(Benzyloxy)-1-(hydroxymethyl)cyclobutyl]-2-chloropropanamide [racemate]

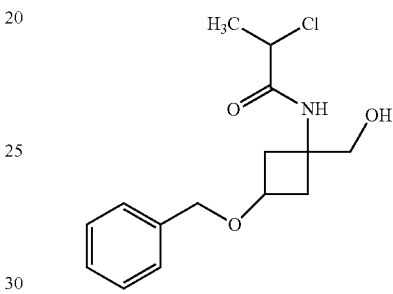

2.81 g (11.5 mmol) of [cis-1-amino-3-(benzyloxy)cyclobutyl]methanol hydrochloride [enantiomerically pure cis isomer] were initially charged in isopropanol (70.0 ml), the mixture was cooled to 0° C. and 4.67 g (6.43 ml, 46.1 mmol) of triethylamine were added. 1.61 g (1.26 ml, 12.7 mmol) of 2-chloropropionyl chloride [racemate] were then added dropwise. The reaction solution was allowed to warm to RT, stirred for 1 h and then concentrated under reduced pressure. The residue was taken up in dichloromethane and washed with an aqueous 1 N hydrogen chloride solution. The organic phases were dried over sodium sulphate, filtered and concentrated under reduced pressure. The crude product was used for the next step without further purification. Yield: 3.38 g (97% of theory).

LC-MS (Method 1A): $R_t$=0.85 min; MS (ESIpos): m/z=298 [M+H]$^+$.

Example 57A cis-2-(Benzyloxy)-7-methyl-8-oxa-5-azaspiro[3.5]nonan-6-one [racemate]

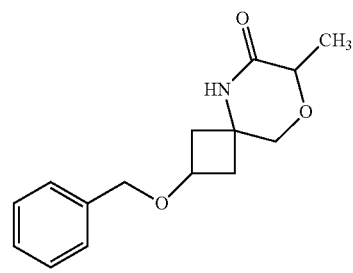 [SMILES: CC1OCC2(CC(OCc3ccccc3)C2)NC1=O]

3.38 g (11.4 mmol) of N-[cis-3-(benzyloxy)-1-(hydroxymethyl)cyclobutyl]-2-chloropropanamide [racemate] were initially charged in isopropanol (250 ml), the mixture was cooled to 0° C. and 3.82 g (34.1 mmol) of potassium tert-butoxide were added in one portion. The mixture was allowed to warm to RT and stirred at 50° C. for 1 h. Most of the isopropanol was then removed under reduced pressure and the residue was taken up in dichloromethane. The organic phase was washed with 1 N aqueous hydrogen chloride solution, dried over sodium sulphate, filtered and concentrated under reduced pressure. The residue was purified by preparative RP-HPLC (acetonitrile/water). Yield: 2.96 g (99% of theory).

LC-MS (Method 1A): $R_t$=0.86 min; MS (ESIpos): m/z=262 [M+H]$^+$.

Example 58A cis-2-(Benzyloxy)-7-methyl-8-oxa-5-azaspiro[3.5]nonane [racemate]

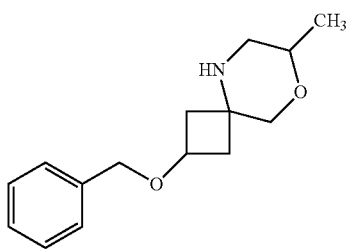 [SMILES: CC1CNC2(CO1)CC(OCc1ccccc1)C2]

2.96 g (11.3 mmol) of cis-2-(benzyloxy)-7-methyl-8-oxa-5-azaspiro[3.5]nonan-6-one [racemate] were initially charged in tetrahydrofuran (200 ml), 22.7 ml (45.3 mmol) of 2 M borane/dimethyl sulphide complex solution in tetrahydrofuran were added under argon and the mixture was stirred under reflux for 2 h. The reaction solution was subsequently cooled to 0° C., methanol (100 ml) was added carefully dropwise and the mixture was stirred under reflux for 12 h. The mixture was then concentrated completely under reduced pressure, and the residue was taken up in acetonitrile and purified directly by preparative RP-HPLC (acetonitrile/water). Yield: 2.80 g (91% of theory).

LC-MS (Method 1A): $R_t$=0.61 min; MS (ESIpos): m/z=248 [M+H]$^+$.

Example 59A tert-Butyl cis-2-(benzyloxy)-7-methyl-8-oxa-5-azaspiro[3.5]nonane-5-carboxylate [racemate]

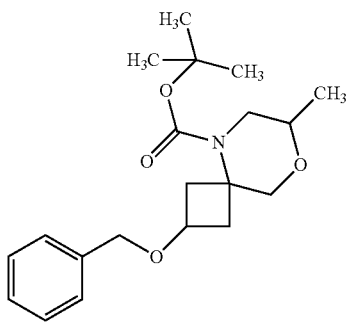 [SMILES: CC1CN(C(=O)OC(C)(C)C)C2(CO1)CC(OCc1ccccc1)C2]

2.80 g (11.3 mmol) of cis-2-(benzyloxy)-7-methyl-8-oxa-5-azaspiro[3.5]nonane [racemate] were initially charged in dichloromethane (150 ml), 3.71 g (17.0 mmol) of di-tert-butyl dicarbonate and 5.73 g (7.89 ml, 56.6 mmol) of triethylamine were added at RT and the mixture was stirred at RT overnight. The reaction solution was washed with an aqueous 0.5 N hydrogen chloride solution, saturated aqueous sodium bicarbonate solution and water. The organic phase was dried over sodium sulphate, filtered and concentrated under reduced pressure. Yield: 3.33 g (84% of theory).

LC-MS (Method 1A): $R_t$=1.28 min; MS (ESIpos): m/z=348 [M+H]$^+$.

Example 60A tert-Butyl cis-2-(benzyloxy)-7-methyl-8-oxa-5-azaspiro[3.5]nonane-5-carboxylate [enantiomerically pure isomer 1]

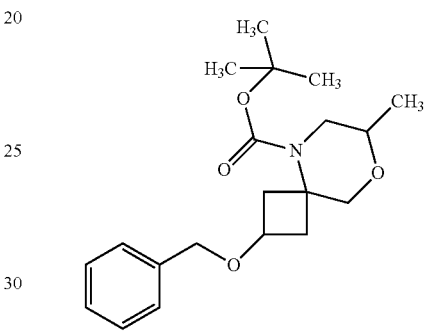

The enantiomer separation of 3.33 g of the compound from Example 59A (Method 5D) gave 1.06 g of the compound from Example 60A (enantiomerically pure isomer 1) and 928 mg of the compound from Example 61A (enantiomerically pure isomer 2).

HPLC (Method 11E): $R_t$=5.06 min, 99.9% ee;

LC-MS (Method 1A): $R_t$=1.30 min; MS (ESIpos): m/z=348 [M+H]$^+$;

$^1$H-NMR (400 MHz, DMSO-d$_6$): δ [ppm]=7.40-7.23 (m, 5H), 4.37 (m$_c$, 2H), 3.79 (quin, 1H), 3.62 (dd, 1H), 3.49-3.33 (m, 3H), 2.69-2.56 (m, 2H), 2.43 (dd, 1H), 2.32-2.23 (m, 1H), 1.78 (m$_c$, 1H), 1.38 (s, 9H), 1.01 (d, 3H).

Example 61A tert-Butyl cis-2-(benzyloxy)-7-methyl-8-oxa-5-azaspiro[3.5]nonane-5-carboxylate [enantiomerically pure isomer 2]

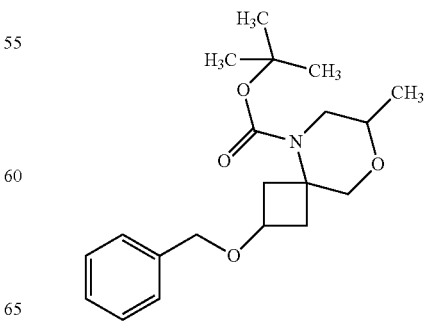

The enantiomer separation of 3.33 g of the compound from Example 59A (Method 5D) gave 1.06 g of the compound from Example 60A (enantiomerically pure isomer 1) and 928 mg of the compound from Example 61A (enantiomerically pure isomer 2).

HPLC (Method 11E): $R_t$=13.5 min, 99.9% ee;
LC-MS (Method 1A): $R_t$=1.30 min; MS (ESIpos): m/z=348 [M+H]$^+$;
$^1$H-NMR (400 MHz, DMSO-d$_6$): δ [ppm]=7.38-7.25 (m, 5H), 4.37 (m$_c$, 1H), 3.79 (quin, 1H), 3.62 (dd, 1H), 3.47-3.34 (m, 2H), 2.68-2.56 (m, 2H), 2.43 (dd, 1H), 2.32-2.22 (m, 1H), 1.78 (m$_c$, 1H), 1.38 (s, 9H), 1.01 (d, 3H).

Example 62A cis-2-(Benzyloxy)-7-methyl-8-oxa-5-azaspiro[3.5] nonane hydrochloride [enantiomerically pure isomer 1]

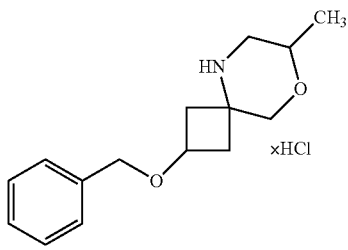 [SMILES: CC1CNC2(CO1)CC(OCc1ccccc1)C2]

1.06 g (3.06 mmol) of tert-butyl cis-2-(benzyloxy)-7-methyl-8-oxa-5-azaspiro[3.5]nonane-5-carboxylate [enantiomerically pure isomer 1 from Example 60A] were initially charged in 1,4-dioxane (30 ml), and 10.0 ml of a 4 N solution of hydrogen chloride in 1,4-dioxane were added at RT. The mixture was stirred at RT overnight and then concentrated under reduced pressure, and the product was dried under high vacuum. Yield: 1.04 g (quant.).

LC-MS (Method 1A): $R_t$=0.48 min; MS (ESIpos): m/z=248 [M+H−HCl]$^+$.

Example 63A cis-2-(Benzyloxy)-7-methyl-8-oxa-5-azaspiro[3.5] nonane hydrochloride [enantiomerically pure isomer 2]

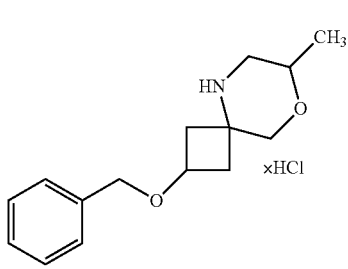 [SMILES: CC1CNC2(CO1)CC(OCc1ccccc1)C2]

928 mg (2.67 mmol) of tert-butyl cis-2-(benzyloxy)-7-methyl-8-oxa-5-azaspiro[3.5]nonane-5-carboxylate [enantiomerically pure isomer 2 from Example 61A] were initially charged in 1,4-dioxane (30 ml), and 10.0 ml of a 4 N solution of hydrogen chloride in 1,4-dioxane were added at RT. The mixture was stirred at RT overnight and then concentrated under reduced pressure, and the product was dried under high vacuum.

Yield: 1.16 g (quant.).
LC-MS (Method 1A): $R_t$=0.51 min; MS (ESIpos): m/z=248 [M+H−HCl]$^+$.

Example 64A cis-7-Methyl-8-oxa-5-azaspiro[3.5]nonan-2-ol hydrochloride [enantiomerically pure isomer 1]

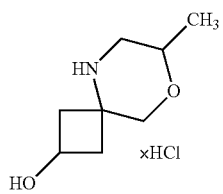

1.03 g (3.66 mmol) of cis-2-(benzyloxy)-7-methyl-8-oxa-5-azaspiro[3.5]nonane hydrochloride [enantiomerically pure isomer 1 from Example 62A] in methanol (36.7 ml) and 3.34 ml of an aqueous 2 N hydrogen chloride solution were initially charged, 119 mg of palladium on carbon (10%) and 59.7 mg of palladium hydroxide on carbon (20%) were added under argon and the mixture was then stirred under an atmosphere of hydrogen at standard pressure overnight. The reaction solution was filtered through kieselguhr and the filter residue was washed with methanol. The filtrate was concentrated under reduced pressure and the product was dried under high vacuum. Yield: 785 mg (99% of theory).

MS (Method 1C): m/z=158 [M+H−HCl]$^+$;
$^1$H-NMR (400 MHz, DMSO-d$_6$): δ [ppm]=9.84 (br. s., 1H), 9.57 (br. s., 1H), 3.78-3.60 (m, 4H), 3.11 (d, 1H), 2.27-2.18 (m, 1H), 2.13-2.00 (m, 2H), 1.09 (d, 3H), three protons obscured.

Example 65A cis-7-Methyl-8-oxa-5-azaspiro[3.5]nonan-2-ol hydrochloride [enantiomerically pure isomer 2]

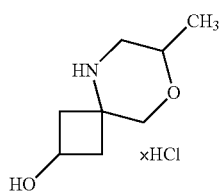

1.16 g (4.11 mmol) of cis-2-(benzyloxy)-7-methyl-8-oxa-5-azaspiro[3.5]nonane hydrochloride [enantiomerically pure isomer 2 from Example 63A] in methanol (41.3 ml) and 3.75 ml of an aqueous 2 N hydrogen chloride solution were initially charged, 134 mg of palladium on carbon (10%) and 67.1 mg of palladium hydroxide on carbon (20%) were added under argon and the mixture was then stirred under an atmosphere of hydrogen at standard pressure overnight. The reaction solution was filtered through kieselguhr and the filter residue was washed with methanol. The filtrate was concentrated under reduced pressure and the product was dried under high vacuum. Yield: 870 mg (98% of theory).

MS (Method 1C): m/z=158 [M+H−HCl]$^+$;

$^1$H-NMR (400 MHz, DMSO-d$_6$): δ [ppm]=9.96 (br. s., 1H), 9.67 (br. s., 1H), 3.84-3.59 (m, 4H), 3.10 (d, 1H), 2.29-2.17 (m, 1H), 2.15-1.99 (m, 2H), 1.09 (d, 3H), three protons obscured.

Example 66A tert-Butyl 2-[(benzylamino)methyl]azetidine-1-carboxylate [racemate]

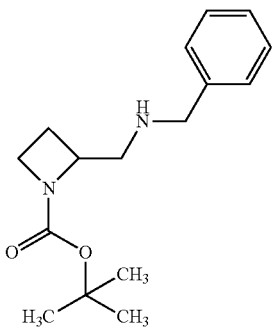 [SMILES: CC(C)(C)OC(=O)N1CCC1CNCc1ccccc1]

10.0 g (53.7 mmol) of tert-butyl 2-(aminomethyl)azetidine-1-carboxylate and 2.03 g (37.8 mmol) of benzaldehyde in 100 ml of methanol were heated under reflux for 2.5 h. The mixture was then cooled to 0° C., and sodium borohydride was added slowly at this temperature over a period of 15 min. The mixture was stirred at RT overnight. The mixture was then concentrated under reduced pressure, dichloromethane and water were added to the residue, the phases were separated and the aqueous phase was extracted twice with dichloromethane. The combined organic phases were washed with saturated aqueous sodium chloride solution, dried over sodium sulphate and filtered, and the filtrate was concentrated under reduced pressure. Dichloromethane was added to the residue obtained, and the product was purified by silica gel chromatography (dichloromethane, then dichloromethane/methanol=100:4). Yield: 7.43 g (50% of theory).

LC-MS (Method 6A): R$_t$=2.41 min; MS (ESIpos): m/z=277 [M+H]$^+$.

Example 67A tert-Butyl 2-{[benzyl(1-methoxy-1-oxopropan-2-yl)amino]methyl}azetidine-1-carboxylate [diastereomer mixture, 4 isomers]

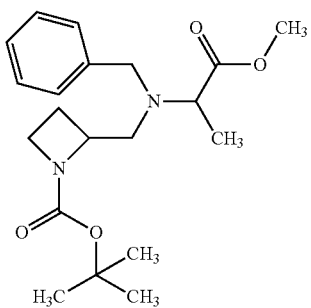 [SMILES: COC(=O)C(C)N(Cc1ccccc1)CC1CCN1C(=O)OC(C)(C)C]

2.50 g (9.05 mmol) of tert-butyl 2-[(benzylamino)methyl]azetidine-1-carboxylate [racemate] were dissolved in dichloromethane (150 ml), 5.55 ml (4.03 g, 39.8 mmol) of triethylamine and 3.04 ml (4.53 g, 27.1 mmol) of methyl 2-bromopropanoate [racemate] were added and the mixture was stirred at RT overnight. 5.55 ml (4.03 g, 39.8 mmol) of triethylamine and 3.04 ml (4.53 g, 27.1 mmol) of methyl 2-bromopropanoate [racemate] were added, and the mixture was stirred at 40° C. overnight. A further 5.55 ml (4.03 g, 39.8 mmol) of triethylamine and 3.04 ml (4.53 g, 27.1 mmol) of methyl 2-bromopropanoate [racemate] were then added, and the mixture was stirred at 40° C. overnight. After cooling to room temperature, the mixture was diluted with water and dichloromethane, and the phases were separated. The aqueous phase was extracted twice with dichloromethane and the combined organic phases were washed with saturated aqueous sodium chloride solution, dried over sodium sulphate, filtered and then freed of the solvent under reduced pressure. The crude product obtained was purified by silica gel chromatography (dichloromethane, then dichloromethane/methanol=100:1). Yield: 3.22 g (94% of theory).

LC-MS (Method 1A): R$_t$=1.00 min (diastereomer 1), R$_t$=1.13 min (diastereomer 2);

MS (ESIpos): m/z=363 [M+H]$^+$;

$^1$H-NMR (400 MHz, DMSO-d$_6$): δ [ppm]=7.35-7.28 (m, 4H), 7.27-7.20 (m, 1H), 4.18-3.98 (m, 1H), 3.85-3.73 (m, 1H), 3.71-3.51 (m, 6H), 3.51-3.38 (m, 1H), 3.04-2.88 (m, 1H), 2.85-2.69 (m, 1H), 2.15-1.96 (m, 1H), 1.93-1.65 (m, 1H), 1.34 (d, 9H), 1.26-1.15 (m, 3H).

Example 68A

Methyl N-(azetidin-2-ylmethyl)-N-benzylalaninate hydrochloride [diastereomer mixture, 4 isomers]

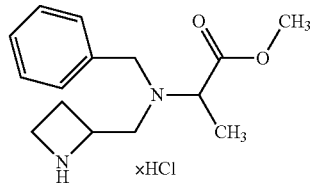 [SMILES: COC(=O)C(C)N(Cc1ccccc1)CC1CCN1]

14.9 ml (59.7 mmol) of a 4 N solution of hydrogen chloride in 1,4-dioxane were added to 3.2 g (8.5 mmol) of tert-butyl 2-{[benzyl(1-methoxy-1-oxopropan-2-yl)amino]methyl}-azetidine-1-carboxylate [diastereomer mixture, 4 isomers] in dioxane (74 ml), and the mixture was stirred at room temperature overnight. A further 14 ml (59.7 mmol) of the 4 N solution of hydrogen chloride in 1,4-dioxane were then added, and the mixture was stirred at RT overnight. The mixture was then concentrated under reduced pressure and the product was dried under high vacuum. Yield: 3.13 g (98% of theory, purity: 80%).

LC-MS (Method 1A): R$_t$=0.68 min (diastereomer 1), R$_t$=0.70 min (diastereomer 2);

MS (ESIpos): m/z=263 [M+H−HCl]$^+$.

Example 69A

4-Benzyl-3-methyl-1,4-diazabicyclo[4.2.0]octan-2-one [enantiomerically pure isomer 3]

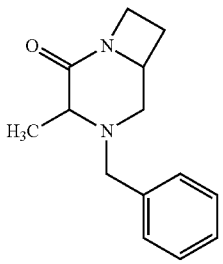 [SMILES: CC1C(=O)N2CCC2CN1Cc1ccccc1]

21.8 g (51.0 mmol, purity: 70%) of methyl N-(azetidin-2-ylmethyl)-N-benzylalaninate [diastereomer mixture, 4 isomers] were initially charged in methanol (562 ml), 28.2 g (204 mmol) of potassium carbonate were added and the mixture was then stirred at RT for 2.5 d. The reaction solution was filtered and most of the solvent was removed at 20° C. under reduced pressure. The residue was taken up in water and extracted repeatedly with dichloromethane and chloroform/isopropanol (7:3). The combined organic phases were dried over sodium sulphate, filtered and concentrated under reduced pressure. Using Method 7D, the crude product (12.1 g) was separated into the corresponding isomers. Here, the target compound eluted as third component. Yield: 2.47 g (21% of theory).

HPLC (Method 6E): $R_t$=7.49 min, 99.0% ee;
LC-MS (Method 1A): $R_t$=0.50 min; MS (ESIpos): m/z=231 [M+H]$^+$.

Example 70A

3-Methyl-1,4-diazabicyclo[4.2.0]octan-2-one [enantiomerically pure isomer 3]

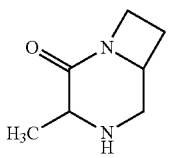

2.40 g (10.4 mmol) of 4-benzyl-3-methyl-1,4-diazabicyclo[4.2.0]octan-2-one [enantiomerically pure isomer 3] were initially charged in ethanol (85 ml), 250 mg of palladium on carbon (10%) and 130 mg of palladium hydroxide on carbon (20%) were added under argon and the mixture was then stirred under an atmosphere of hydrogen at standard pressure overnight. The reaction solution was filtered through kieselguhr and the filter residue was washed with hot ethanol (100 ml). The filtrate was concentrated under reduced pressure and the product was dried under high vacuum. Yield: 1.56 g (quant.).

GC-MS (Method 2B): $R_t$=4.50 min; MS (EIpos): m/z=140 [M]$^+$;
MS (Method 1C): m/z=141 [M+H]$^+$;
$^1$H-NMR (400 MHz, DMSO-d$_6$): δ [ppm]=4.59 (m$_c$, 1H), 4.09-3.89 (m, 2H), 3.27 (q, 1H), 2.95 (dd, 1H), 2.58-2.53 (m, 2H), 2.33-2.04 (m, 2H), 1.12 (d, 3H).

Example 71A

N-Benzyl-2-chloro-N-[(2R)-1,4-dihydroxybutan-2-yl]propanamide [diastereomer mixture, 2 isomers]

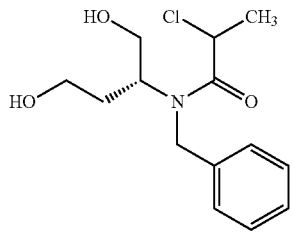 [SMILES: CC(Cl)C(=O)N(Cc1ccccc1)[C@@H](CO)CCO]

45.1 g (55.3 mmol, purity: 72%) of (2R)-2-(benzylamino)butane-1,4-diol [B. L. Feringa, *Tetrahedron* 1989, 45, 6799-6818] were initially charged in isopropanol (239 ml), the mixture was cooled to 0° C. and 11.2 g (15.4 ml, 111 mmol) of triethylamine were added. 10.5 g (8.23 ml, 83.0 mmol) of 2-chloropropionyl chloride [racemate] were then added dropwise. After 10 min of stirring, the reaction solution was concentrated under reduced pressure and the residue was taken up in ethyl acetate and washed with water. The organic phase was dried over sodium sulphate, filtered and concentrated under reduced pressure. The crude product was used for the next step without further purification. Yield: 21.4 g (quant., purity: 82%, diastereomer ratio about 3:2).

LC-MS (Method 1A): $R_t$=0.65 min (enantiomerically pure isomer 1), $R_t$=0.67 min (enantiomerically pure isomer 2);
MS (ESIpos): m/z=286 [M+H]$^+$.

Example 72A

(5R)-4-Benzyl-5-(2-hydroxyethyl)-2-methylmorpholin-3-one [diastereomer mixture, 2 isomers]

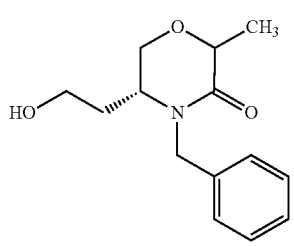 [SMILES: CC1OC[C@@H](CCO)N(Cc2ccccc2)C1=O]

21.4 g (62.1 mmol, purity: 82%) of N-benzyl-2-chloro-N-[(2R)-1,4-dihydroxybutan-2-yl]propanamide [diastereomer mixture, 2 isomers] were initially charged in isopropanol (335 ml), the mixture was cooled to 0° C. and 27.9 g (249 mmol) of potassium tert-butoxide were then added in one portion. The reaction was stirred overnight and allowed to warm to RT during this time. Most of the isopropanol was removed under reduced pressure, and the residue was taken up in water (300 ml) and extracted with ethyl acetate. The organic phases were dried over sodium sulphate, filtered and concentrated under reduced pressure. The crude product was used for the next step without further purification. Yield: 13.3 g (69% of theory, purity: 81%, diastereomer ratio about 3:2).

LC-MS (Method 7A): $R_t$=3.23 min (enantiomerically pure isomer 1), $R_t$=3.34 min (enantiomerically pure isomer 2);
MS (ESIpos): m/z=250 [M+H]$^+$.

Example 73A (5R)-4-Benzyl-5-({[tert-butyl(dimethyl)silyl]oxy}ethyl)-2-methylmorpholin-3-one [diastereomer mixture, 2 isomers]

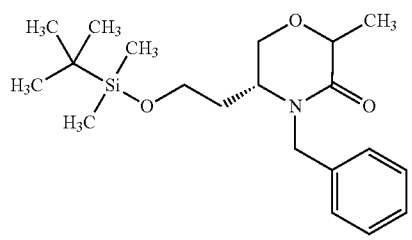 [SMILES: CC1OC[C@@H](CCO[Si](C)(C)C(C)(C)C)N(Cc2ccccc2)C1=O]

13.3 g (43.3 mmol) of (5R)-4-benzyl-5-(2-hydroxyethyl)-2-methylmorpholin-3-one [diastereomer mixture, 2 isomers] were initially charged in N,N-dimethylformamide (60.0 ml), and 8.85 g (130 mmol) of imidazole were added at RT. At 0° C., 9.80 g (65.0 mmol) of tert-butyldimethylsilyl chloride were then added and the reaction solution was stirred overnight and allowed to warm to RT during this time. The mixture was subsequently concentrated under reduced pressure, taken up in ethyl acetate and washed repeatedly with water and once with saturated aqueous sodium chloride solution. The organic phase was dried over magnesium sulphate, filtered and concentrated under reduced pressure. The crude product was then purified chromatography on silica gel (cyclohexane/ethyl acetate 6:1, then cyclohexane/ethyl acetate 5:1). Yield: 8.03 g (49% of theory, diastereomer ratio: about 2.3:1).

LC-MS (Method 1A): $R_t$=1.41 min; MS (ESIpos): m/z=364 [M+H]$^+$;

$^1$H-NMR (400 MHz, DMSO-$d_6$): δ [ppm]=7.40-7.18 (m, 5H), 5.12-5.03 (m, 1H), 4.33-4.21 (m, 1H), 4.14 (d, 0.3H), 4.05 (m, 0.7H), 3.95-3.84 (m, 1H), 3.74-3.56 (m, 3H), 3.39 (dd, 0.3H), 3.28 (d, 0.7H), 1.98-1.70 (m, 2H), 1.39 (d, 0.9H), 1.35 (d, 2.1H), 0.82 (s, 9H), 0.02 (s, 1.8H), 0.00 (s, 4.2H).

Example 74A (5R)-4-Benzyl-5-(2-{[tert-butyl(dimethyl)silyl]oxy}ethyl)-2,2-dimethylmorpholin-3-one [enantiomerically pure isomer]

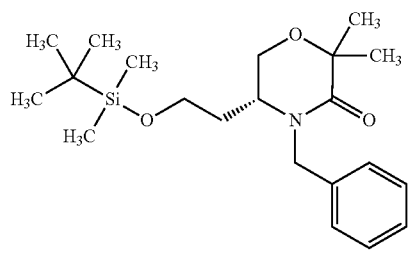 [SMILES: CC1(C)OC[C@@H](CCO[Si](C)(C)C(C)(C)C)N(Cc2ccccc2)C1=O]

7.00 g (18.6 mmol) of (5R)-4-benzyl-5-(2-{[tert-butyl(dimethyl)silyl]oxy}ethyl)-2-methylmorpholin-3-one [diastereomer mixture, 2 isomers] were initially charged in tetrahydrofuran (233 ml), and 13.0 ml (26.1 mmol) of lithium diisopropylamide solution (2.0 M in tetrahydrofuran/n-heptane/ethylbenzene) were added dropwise at −78° C. The mixture was stirred for 15 min, and 3.17 g (1.39 ml, 22.4 mmol) of iodomethane were then added. The reaction solution was allowed to warm to RT and stirred for 2 h. The reaction was terminated by addition of saturated aqueous ammonium chloride solution and the mixture was extracted with ethyl acetate. The organic phase was washed with saturated aqueous sodium chloride solution, dried over magnesium sulphate, filtered and concentrated under reduced pressure. The crude product was used for the next step without further purification. Yield: 8.36 g (70% of theory, purity: 59%).

LC-MS (Method 1A): $R_t$=1.47 min; MS (ESIpos): m/z=378 [M+H]$^+$.

Example 75A (5R)-4-Benzyl-5-(2-{[tert-butyl(dimethyl)silyl]oxy}ethyl)-2,2-dimethylmorpholine [enantiomerically pure isomer]

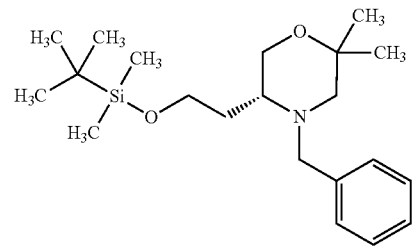 [SMILES: CC1(C)CN(Cc2ccccc2)[C@H](CCO[Si](C)(C)C(C)(C)C)CO1]

8.36 g (13.1 mmol, purity: 59%) of (5R)-4-benzyl-5-(2-{[tert-butyl(dimethyl)silyl]oxy}ethyl)-2,2-dimethylmorpholin-3-one [enantiomerically pure isomer] were initially charged in tetrahydrofuran (133 ml), 26.2 ml (52.3 mmol) of 2 M borane/dimethyl sulphide complex solution in tetrahydrofuran were added under argon and the mixture was stirred under reflux for 4 h. The mixture was subsequently cooled to 0° C., methanol (30 ml) was added carefully and the mixture was stirred under reflux for 30 min and then concentrated under reduced pressure. The crude product was used for the next step without further purification. Yield: 8.39 g (96% of theory, purity: 55%).

LC-MS (Method 1A): $R_t$=1.15 min; MS (ESIpos): m/z=364 [M+H]$^+$.

Example 76A

2-[(3R)-4-Benzyl-6,6-dimethylmorpholin-3-yl]ethanol [enantiomer mixture, 2 isomers]

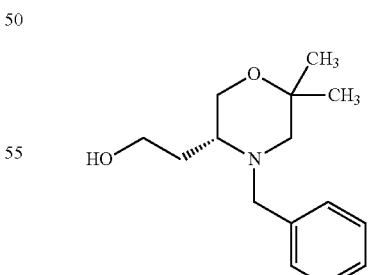

7.39 g (11.2 mmol, purity: 55%) of (5R)-4-benzyl-5-(2-{[ten-butyl(dimethyl)silyl]oxy}ethyl)-2,2-dimethylmorpholine [enantiomerically pure isomer] were initially charged in tetrahydrofuran (148 ml), and 30.5 ml (30.5 mmol) of tetra-n-butylammonium fluoride solution (1.0 M in tetrahydrofuran) were added at RT. The mixture was stirred at RT for 1 h and then concentrated under reduced pressure. The residue was purified by preparative RP-HPLC (acetonitrile/water, isocratic). Yield: 1.97 g (38% of theory, enantiomer ratio: about 85:15); at this stage, a proportional isomerization of the stereocentre to one of the earlier precursors was noticed.

HPLC (Method 7E): $R_t$=4.41 min, 85:15 R:S enantiomer ratio;

LC-MS (Method 1A): $R_t$=0.35 min; MS (ESIpos): m/z=250 [M+H]$^+$;

$^1$H-NMR (400 MHz, DMSO-d$_6$): δ [ppm]=7.31 (d, 4H), 7.22 (m$_c$, 1H), 4.45 (t, 1H), 3.93 (d, 1H), 3.60 (dd, 1H), 3.54-3.40 (m, 3H), 3.10 (d, 1H), 2.40-2.29 (m, 2H), 1.85 (d, 1H), 1.79-1.69 (m, 1H), 1.59 (m$_c$, 1H), 1.14 (s, 3H), 1.04 (s, 3H).

Example 77A

2-[(3R)-6,6-Dimethylmorpholin-3-yl]ethanol [enantiomer mixture, 2 isomers]

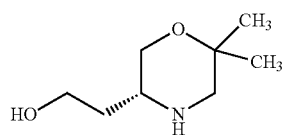

1.00 g (4.01 mmol) of 2-[(3R)-4-benzyl-6,6-dimethylmorpholin-3-yl]ethanol [enantiomer mixture, enantiomer ratio: about 85:15] were initially charged in ethanol (40.0 ml), 150 mg of palladium on carbon (10%) and 150 mg of palladium hydroxide on carbon (20%) were added under argon and the mixture was stirred under an atmosphere of hydrogen at standard pressure for 4 h. The reaction solution was filtered through kieselguhr and concentrated under reduced pressure. Yield: 680 mg (quant.).

GC-MS (Method 2B): $R_t$=3.71 min; MS (EIpos): m/z=159 [M]$^+$;

$^1$H-NMR (500 MHz, DMSO-d$_6$): δ [ppm]=4.32 (br. s., 1H), 3.46 (t, 2H), 3.38 (dd, 1H), 3.21 (t, 1H), 2.64-2.54 (m, 2H), 2.47-2.42 (m, 1H), 1.36 (m$_c$, 2H), 1.18 (s, 3H), 1.02 (s, 3H), one proton obscured.

Example 78A

1-Benzyl 2-ethyl (4R)-4-ethoxypyrrolidine-1,2-dicarboxylate [diastereomer mixture, 2 isomers]

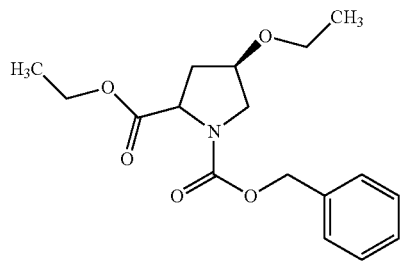 [SMILES: CCOC(=O)C1C[C@@H](OCC)CN1C(=O)OCc1ccccc1]

Under argon, 10.0 g (37.7 mmol) of (4R)-1-[(benzyloxy)carbonyl]-4-hydroxy-L-proline were initially charged in N,N-dimethylformamide (110 ml), and 1.96 g (49.0 mmol, 60% suspension in paraffin oil) of sodium hydride were added at 0° C. The reaction mixture was stirred for 30 min, and 7.54 ml (14.7 g, 94.2 mmol) of iodoethane were then added. The mixture was allowed to warm to RT, then cooled again to 0° C., 1.96 g (49.0 mmol, 60% suspension in paraffin oil) of sodium hydride were added and the mixture was stirred for 30 min. A further 7.54 ml (14.7 g, 94.2 mmol) of iodoethane were added, and the mixture was once more warmed to RT and stirred overnight. Water was added carefully, and the reaction mixture was extracted with ethyl acetate. The organic phase was dried over sodium sulphate, filtered and concentrated under reduced pressure. The crude product was used for the next step without further purification. Yield: 14.8 g (94% of theory, purity: 77%).

LC-MS (Method 1A): $R_t$=1.06 min; MS (ESIpos): m/z=322 [M+H]$^+$.

Example 79A

Benzyl (4R)-4-ethoxy-2-(hydroxymethyl)pyrrolidine-1-carboxylate [diastereomer mixture, 2 isomers]

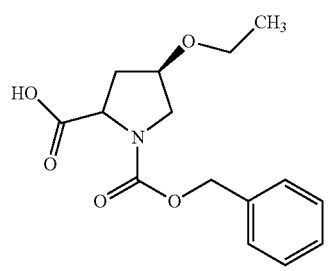 [SMILES: CCO[C@@H]1CC(C(=O)O)N(C(=O)OCc2ccccc2)C1]

13.5 g (32.6 mmol, purity: 77%) of 1-benzyl 2-ethyl (4R)-4-ethoxypyrrolidine-1,2-dicarboxylate [diastereomer mixture, 2 isomers] were initially charged in tetrahydrofuran (150 ml) under argon, and 817 mg (37.5 mmol) of lithium borohydride were added at 0° C. The reaction mixture was allowed to warm to RT and then stirred at RT overnight. Water (100 ml) was added carefully, the pH was adjusted to pH=1 using an aqueous 2 N hydrogen chloride solution and the mixture was then extracted with ethyl acetate. The organic phases were washed with saturated sodium chloride solution, dried over sodium sulphate, filtered and concentrated under reduced pressure. The crude product was purified by preparative RP-HPLC (acetonitrile/water). Yield: 4.78 g (52% of theory, diastereomer ratio: about 2:1).

LC-MS (Method 1A): $R_t$=0.81 min (diastereomer 1), $R_t$=0.83 min (diastereomer 2);

MS (ESIpos): m/z=280 [M+H]$^+$.

Example 80A

[(4R)-4-Ethoxypyrrolidin-2-yl]methanol [diastereomer mixture, 2 isomers]

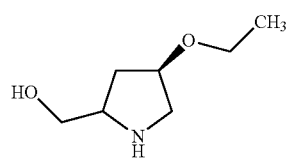

2.00 g (7.16 mmol) of benzyl (4R)-4-ethoxy-2-(hydroxymethyl)pyrrolidine-1-carboxylate [diastereomer mixture, 2 isomers] were initially charged in methanol (46.3 ml), 221 mg of palladium on carbon (10%) and 111 mg of platinum(IV) oxide were added under argon and the mixture was stirred under a hydrogen atmosphere at standard pressure until the hydrogen uptake had ended. The reaction solution was filtered through kieselguhr, the filter cake was washed with methanol and the filtrate was concentrated under reduced pressure.

Yield: 1.17 g (quant.).

MS (Method 2C): m/z=146 [M+H]$^+$;

$^1$H-NMR (400 MHz, DMSO-d$_6$): δ [ppm]=4.04-2.67 (m, 10H), 2.10-1.30 (m, 2H), 1.22-0.97 (m, 3H).

Example 81A

Benzyl (4R)-4-ethoxy-2-formylpyrrolidine-1-carboxylate [diastereomer mixture, 2 isomers]

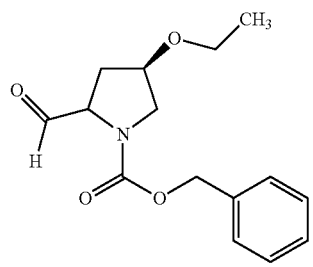 [SMILES: CCO[C@@H]1CC(C=O)N(C(=O)OCc2ccccc2)C1]

2.60 g (9.31 mmol) of benzyl (4R)-4-ethoxy-2-(hydroxymethyl)pyrrolidine-1-carboxylate [diastereomer mixture, 2 isomers] were initially charged in dichloromethane (46.6 ml), and 4.36 g (3.96 ml, 55.9 mmol) of dimethyl sulphoxide, 9.62 g (13.0 mL, 129 mmol) of N,N-diisopropylethylamine and 5.93 g (37.2 mmol) of sulphur trioxide/pyridine complex were added at 0° C. The reaction solution was allowed to warm to RT and was stirred at RT for 3 h. The reaction solution was diluted with dichloromethane and washed with water and saturated sodium chloride solution, dried over sodium sulphate, filtered and concentrated under reduced pressure. The crude product was used for the next step without further purification. Yield: 4.10 g (quant., purity: 65%).

LC-MS (Method 1A): R$_t$=0.96 min (enantiomerically pure isomer 1), R$_t$=0.97 min (enantiomerically pure isomer 2);

MS (ESIpos): m/z=278 [M+H]$^+$.

Example 82A

Benzyl (4R)-4-ethoxy-2-vinylpyrrolidine-1-carboxylate [diastereomer mixture, 2 isomers]

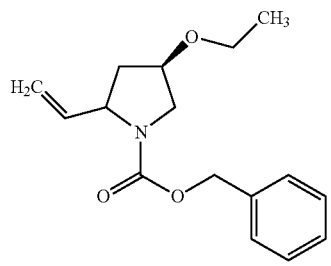 [SMILES: C=CC1C[C@@H](OCC)CN1C(=O)OCc1ccccc1]

At 0° C. and under argon, 4.23 ml (10.6 mmol, 2.5 M solution in n-hexane) of n-butyllithium were added dropwise to 4.81 g (13.5 mmol) of methyltriphenylphosphonium bromide in tetrahydrofuran (30.8 ml). The reaction solution was allowed to warm to RT. The mixture was stirred at RT for 30 min, then once more cooled to 0° C., and 4.10 g (9.61 mmol, purity: 65%) of benzyl (4R)-4-ethoxy-2-formylpyrrolidine-1-carboxylate [diastereomer mixture, 2 isomers] in THF were then added dropwise over 10 min. The reaction solution was stirred for 30 min and then poured into ice-water. The mixture was extracted with diethyl ether, and the organic phases were dried over sodium sulphate, filtered and concentrated under reduced pressure. The crude product was purified by preparative RP-HPLC (acetonitrile/water). Yield: 954 mg (36% of theory, diastereomer ratio: about 2:1).

LC-MS (Method 1A): R$_t$=1.11 min (diastereomer 1), R$_t$=1.13 min (diastereomer 2);

MS (ESIpos): m/z=276 [M+H]$^+$.

Example 83A

Benzyl (4R)-4-ethoxy-2-(2-hydroxyethyl)pyrrolidine-1-carboxylate [diastereomer mixture, 2 isomers]

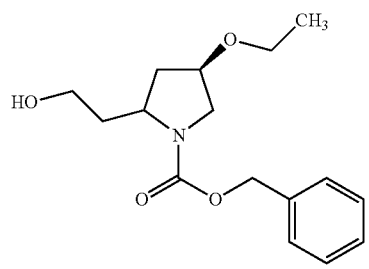 [SMILES: CCO[C@@H]1CC(CCO)N(C(=O)OCc2ccccc2)C1]

At 0° C., 34.7 ml (17.3 mmol, 0.5 M solution in tetrahydrofuran) of 9-borabicyclo[3.3.1]nonane were added dropwise to 954 mg (3.47 mmol) of benzyl (4R)-4-ethoxy-2-vinylpyrrolidine-1-carboxylate [diastereomer mixture, 2 isomers] in tetrahydrofuran (53 ml). The reaction solution was allowed to slowly warm to RT. Subsequently, at 0° C., 1 N aqueous sodium carbonate solution (40 ml) and then 30% strength aqueous hydrogen peroxide solution (40 ml) were added. The reaction solution was then warmed to RT and stirred for 30 min. Ethyl acetate was then added to the reaction solution, and the organic phase was washed with water and saturated sodium chloride solution. The organic phases were dried over sodium sulphate, filtered and concentrated under reduced pressure. The crude product was purified by preparative RP-HPLC (acetonitrile/water). Yield: 781 mg (75% of theory, diastereomer ratio: about 2.5:1).

LC-MS (Method 1A): R$_t$=0.87 min (diastereomer 1), R$_t$=0.90 min (diastereomer 2);

MS (ESIpos): m/z=294 [M+H]$^+$.

Example 84A

2-[(4R)-4-Ethoxypyrrolidin-2-yl]ethanol [diastereomer mixture, 2 isomers]

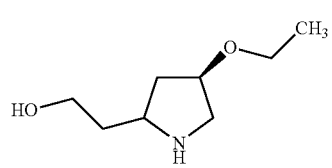

780 mg (2.66 mmol) of benzyl (4R)-4-ethoxy-2-(2-hydroxyethyl)pyrrolidine-1-carboxylate [diastereomer mixture, 2 isomers] were initially charged in methanol (17.2 ml), 82.2 mg of palladium on carbon (10%) and 41.1 mg of platinum(IV) oxide were added under argon and the mixture was then stirred under a hydrogen atmosphere at standard pressure until the hydrogen uptake had ended. The reaction solution was filtered through kieselguhr, the filter cake was washed with methanol and the filtrate was concentrated under reduced pressure.

Yield: 465 mg (quant.).

MS (Methode 1C): m/z=160 [M+H−HCl]$^+$.

Example 85A tert-Butyl 4-benzyl-5-oxo-4,7-diazaspiro[2.5]octane-7-carboxylate

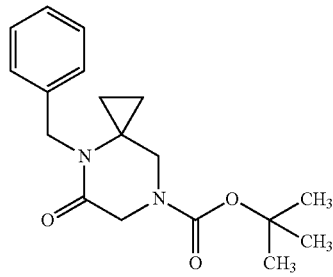

Under argon and at 0° C., 2.47 g (61.9 mmol) of sodium hydride were added a little at a time to 2.50 g (8.84 mmol) of tert-butyl 5-oxo-4,7-diazaspiro[2.5]octane-7-carboxylate in 80 ml of THF, and the mixture was stirred at 0° C. for 30 min. 1.26 ml (1.81 g, 10.6 mmol) of benzyl bromide were then added dropwise, and the mixture was stirred at room temperature overnight. The mixture was then cooled to 0° C., 1.24 g (30.9 mmol) of sodium hydride were added and the mixture was stirred at 0° C. for 30 min 0.63 ml (0.91 g, 5.3 mmol) of benzyl bromide was added dropwise, and the mixture was stirred at room temperature overnight. At 0° C., first ethanol and then water and ethyl acetate were added. After phase separation, the aqueous phase was extracted twice with ethyl acetate and the combined organic phases were dried over sodium sulphate After filtration, the filtrate was concentrated under reduced pressure and the residue was dried under high vacuum and purified by silica gel chromatography (cyclohexane/ethyl acetate 10:1) and then by preparative HPLC (RP18 column, mobile phase: acetonitrile/water gradient). This gave 1.98 g (71% of theory) of the desired product.

LC-MS (Method 1A): $R_t$=1.09 min; MS (ESIpos): m/z=317 [M+H]$^+$ $^1$H-NMR (400 MHz, DMSO-d$_6$): δ [ppm]=7.38-7.14 (m, 5H), 4.41 (s, 2H), 4.16 (br. s., 2H), 1.40 (br. s., 9H), 0.98-0.89 (m, 2H), 0.79-0.72 (m, 2H).

Example 86A tert-Butyl 4-benzyl-6-methyl-5-oxo-4,7-diazaspiro [2.5]octane-7-carboxylate [racemate]

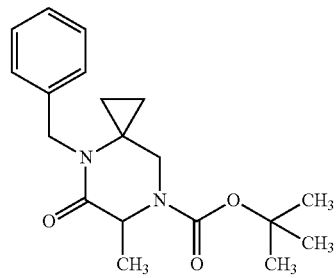 [SMILES: CC1C(=O)N(Cc2ccccc2)C2(CC2)CN1C(=O)OC(C)(C)C]

At −78° C. and under argon, 11.38 ml (11.38 mmol) of a 1 M solution of lithium hexamethyldisilazide in THF were added dropwise to 1.20 g (3.79 mmol) of tert-butyl 4-benzyl-5-oxo-4,7-diazaspiro[2.5]octane-7-carboxylate in 48 ml of THF, and the mixture was stirred at −78° C. for 30 min 0.47 ml (7.59 mmol) of methyl iodide was then added dropwise, and the mixture was stirred for 1.5 h. At 0° C., first saturated aqueous ammonium chloride solution and then ethyl acetate were added. After phase separation, the aqueous phase was extracted twice with ethyl acetate, and the combined organic phases were washed with saturated aqueous sodium chloride solution and then dried over sodium sulphate After filtration, the filtrate was concentrated under reduced pressure and the residue was dried under high vacuum, dissolved in acetonitrile and water and purified by preparative HPLC (RP18 column, mobile phase: acetonitrile/water gradient). This gave 0.54 g (41% of theory) of the desired product.

Example 87A tert-Butyl 6-methyl-5-oxo-4,7-diazaspiro[2.5]octane-7-carboxylate [racemate]

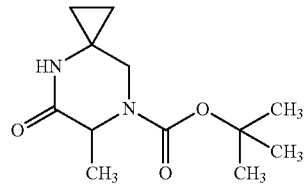

At −78° C., 107 mg (15.5 mmol) of lithium were added to 10 ml (7.70 g, 452 mmol) of ammonia, and the mixture was stirred for a few minutes. 540 mg (1.55 mmol) of tert-butyl 4-benzyl-6-methyl-5-oxo-4,7-diazaspiro[2.5]octane-7-carboxylate [racemate] in 5 ml of THF were then added dropwise, and the mixture was slowly warmed to room temperature and then stirred at room temperature overnight. At 0° C., first saturated aqueous ammonium chloride solution and then ethyl acetate were added. After phase separation, the aqueous phase was extracted twice with ethyl acetate, and the combined organic phases were washed with saturated aqueous sodium chloride solution and dried over sodium sulphate After filtration, the filtrate was concentrated under reduced pressure and the residue was dried under high vacuum. This gave 353 mg of the crude product which was used without further purification.

MS (Method 1C): m/z=241 [M+H]+.

Example 88A

6-Methyl-4,7-diazaspiro[2.5]octan-5-one trifluoroacetate [racemate]

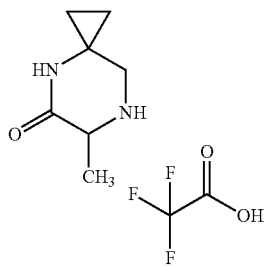

1.06 ml (1.57 g, 13.8 mmol) of trifluoroacetic acid were added to 331 mg (1.38 mmol) of tert-butyl 6-methyl-5-oxo-4,7-diazaspiro[2.5]octane-7-carboxylate [racemate] in 10 ml of dichloromethane, and the mixture was stirred at room temperature for 2 h. The mixture was then concentrated under reduced pressure and the residue was dissolved in dichloromethane. The solution was concentrated under reduced pressure and the residue obtained was re-dissolved in dichloromethane, freed of the solvent under reduced pressure and dried under high vacuum. The crude product obtained (605 mg) was used further without purification.

MS (Method 1C): m/z=141 [M+H]+.

WORKING EXAMPLES

Example 1

(2-{[1-(3-Chlorophenyl)-2-fluoroethyl]amino}-7-methoxy-1,3-benzoxazol-5-yl)(4-hydroxy-3-methyl-piperidin-1-yl)methanone [1:1 trans diastereomer mixture, 2 isomers]

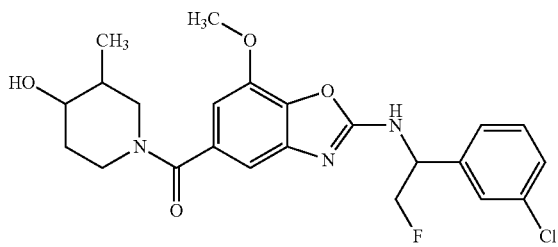 [SMILES: COc1cc(C(=O)N2CCC(O)C(C)C2)cc2nc(NC(CF)c3cccc(Cl)c3)oc12]

200 mg (0.250 mmol, purity: 46%) of 2-{[1-(3-chlorophenyl)-2-fluoroethyl]amino}-7-methoxy-1,3-benzoxazole-5-carboxylic acid [enantiomerically pure isomer] and 34.9 mg (0.300 mmol) of 3-methylpiperidin-4-ol [racemic trans isomer, 2 isomers] were initially charged in N,N-dimethylformamide (2.00 ml), and 131 mg (176 μl, 1.01 mmol) of N,N-diisopropylethylamine were added. 115 mg (0.300 mmol) of HATU were then added at RT, and the mixture was stirred for 1 h. 17.5 mg (0.150 mmol) of 3-methylpiperidin-4-ol [racemic trans isomer], 66.5 mg (88 μl, 0.505 mmol) of N,N-diisopropylethylamine and 57.5 mg (0.150 mmol) of HATU were added, and the mixture was subsequently stirred overnight. Without further work-up, the reaction solution was purified by preparative RP-HPLC (acetonitrile/water). Yield: 76.6 mg (65% of theory).

LC-MS (Method 1A): R$_t$=0.88 min; MS (ESIpos): m/z=462 [M+H]+;

$^1$H-NMR (400 MHz, DMSO-d$_6$): δ [ppm]=8.99 (d, 1H), 7.58 (s, 1H), 7.50-7.28 (m, 3H), 6.82 (s, 1H), 6.69 (s, 1H), 5.24 (m$_c$, 1H), 4.84-4.49 (m, 3H), 4.25 (br. s., 1H), 3.91 (s, 3H), 3.50 (br. s., 1H), 3.22-3.08 (m, 1H), 3.07-2.78 (br. m., 1H), 1.91-1.64 (br. m., 1H), 1.49-1.20 (m, 2H), 0.85 (br. d., 3H).

Example 2

(2-{[1-(3-Chlorophenyl)-2-fluoroethyl]amino}-7-methoxy-1,3-benzoxazol-5-yl)(4-hydroxy-3-methyl-piperidin-1-yl)methanone [enantiomerically pure trans isomer 1]

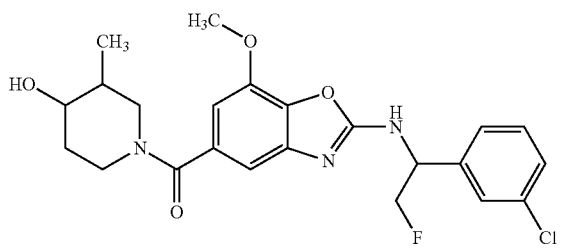 [SMILES: COc1cc(C(=O)N2CCC(O)C(C)C2)cc2nc(NC(CF)c3cccc(Cl)c3)oc12]

Diastereomer separation on a chiral phase of 70.0 mg of the compound from Example 1 according to Method 3D gave 32.0 mg of Example 2 (enantiomerically pure trans isomer 1) and 32.0 mg of Example 3 (enantiomerically pure trans isomer 2).

HPLC (Method 3E): R$_t$=9.37 min, 99.0% de;

LC-MS (Method 1A): R$_t$=0.91 min; MS (ESIpos): m/z=462 [M+H]+;

$^1$H-NMR (400 MHz, DMSO-d$_6$): δ [ppm]=8.99 (d, 1H), 7.58 (s, 1H), 7.50-7.28 (m, 3H), 6.82 (s, 1H), 6.69 (s, 1H), 5.24 (m$_c$, 1H), 4.84-4.49 (m, 3H), 4.25 (br. s., 1H), 3.91 (s, 3H), 3.50 (br. s., 1H), 3.22-3.08 (m, 1H), 3.07-2.78 (br. m., 1H), 1.91-1.64 (br. m., 1H), 1.49-1.20 (m, 2H), 0.85 (br. d., 3H).

Example 3

(2-{[1-(3-Chlorophenyl)-2-fluoroethyl]amino}-7-methoxy-1,3-benzoxazol-5-yl)(4-hydroxy-3-methyl-piperidin-1-yl)methanone [enantiomerically pure trans diastereomer 2]

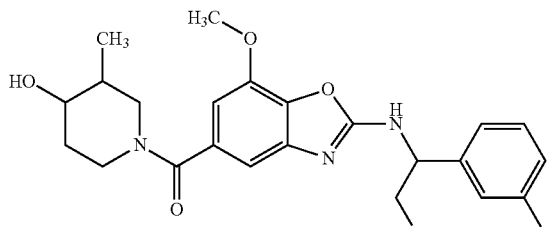

Diastereomer separation on a chiral phase of 70.0 mg of the compound from Example 1 according to Method 3D gave 32.0 mg of Example 2 (enantiomerically pure isomer 1) and 32.0 mg of Example 3 (enantiomerically pure isomer 2).

HPLC (Method 3E): $R_t$=15.1 min, 99.0% de;
LC-MS (Method 1A): $R_t$=0.91 min; MS (ESIpos): m/z=462 [M+H]$^+$;
$^1$H-NMR (400 MHz, DMSO-$d_6$): δ [ppm]=8.99 (d, 1H), 7.58 (s, 1H), 7.50-7.28 (m, 3H), 6.82 (s, 1H), 6.69 (s, 1H), 5.24 ($m_c$, 1H), 4.84-4.49 (m, 3H), 4.25 (br. s., 1H), 3.91 (s, 3H), 3.50 (br. s., 1H), 3.22-3.08 (m, 1H), 3.07-2.78 (br. m., 1H), 1.91-1.64 (br. m., 1H), 1.49-1.20 (m, 2H), 0.85 (br. d., 3H).

Example 4

(2-{[1-(3-Chlorophenyl)-2-fluoroethyl]amino}-7-methoxy-1,3-benzoxazol-5-yl)[5-(hydroxymethyl)-2,2-dimethylmorpholin-4-yl]methanone [1:1 diastereomer mixture, 2 isomers]

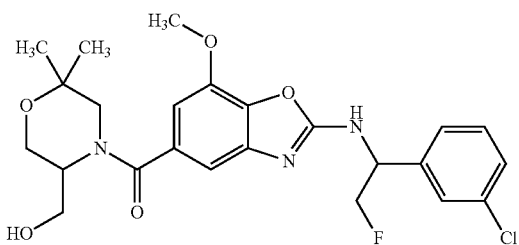 [SMILES: COc1cc(C(=O)N2CC(C)(C)OCC2CO)cc2nc(NC(CF)c3cccc(Cl)c3)oc12]

80.0 mg (0.101 mmol, purity: 46%) of 2-{[1-(3-chlorophenyl)-2-fluoroethyl]amino}-7-methoxy-1,3-benzoxazole-5-carboxylic acid [enantiomerically pure isomer] and 38.2 mg (0.263 mmol) of (6,6-dimethylmorpholin-3-yl)methanol [racemate] were initially charged in N,N-dimethylformamide (1.01 ml), and 99.2 mg (134 µl, 0.786 mmol) of N,N-diisopropylethylamine were added. Subsequently, 100 mg (0.263 mmol) of HATU were added at RT and the mixture was stirred overnight. Without further work-up, the reaction solution was then purified by preparative RP-HPLC (acetonitrile/water). Yield: 55.1 mg (99% of theory, purity: 90%).

LC-MS (Method 3A): $R_t$=2.02 min; MS (ESIpos): m/z=492 [M+H]$^+$;
$^1$H-NMR (400 MHz, DMSO-$d_6$): δ [ppm]=8.98 ($m_c$, 1H), 7.58 (s, 1H), 7.50-7.37 (m, 3H), 6.90 (br. s., 1H), 6.74 (br. s., 1H), 5.24 ($m_c$, 1H), 4.88 (br. s., 1H), 4.80-4.51 (m, 2H), 4.01-3.38 (m, 9H), 3.20-2.74 (m, 1H), 1.14 (br. s., 6H).

Example 5

(2-{[1-(3-Chlorophenyl)-2-fluoroethyl]amino}-7-methoxy-1,3-benzoxazol-5-yl)[5-(hydroxymethyl)-2,2-dimethylmorpholin-4-yl]methanone [enantiomerically pure isomer 1]

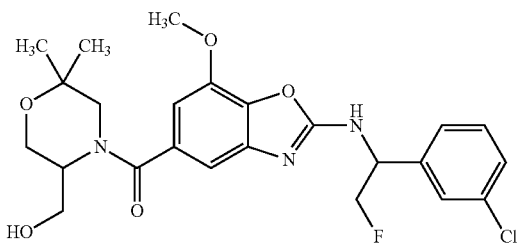 [SMILES: COc1cc(C(=O)N2CC(C)(C)OCC2CO)cc2nc(NC(CF)c3cccc(Cl)c3)oc12]

Diastereomer separation on a chiral phase of 50.0 mg of the compound from Example 4 according to Method 4D gave, after re-purification by preparative RP-HPLC (acetonitrile/water), 16.2 mg of Example 5 (enantiomerically pure isomer 1) and 22.1 mg of Example 6 (enantiomerically pure isomer 2).

HPLC (Method 4E): $R_t$=5.05 min, >99.0% de;
LC-MS (Method 1A): $R_t$=0.94 min; MS (ESIpos): m/z=492 [M+H]$^+$.

Example 6

(2-{[1-(3-Chlorophenyl)-2-fluoroethyl]amino}-7-methoxy-1,3-benzoxazol-5-yl)[5-(hydroxymethyl)-2,2-dimethylmorpholin-4-yl]methanone [enantiomerically pure isomer 2]

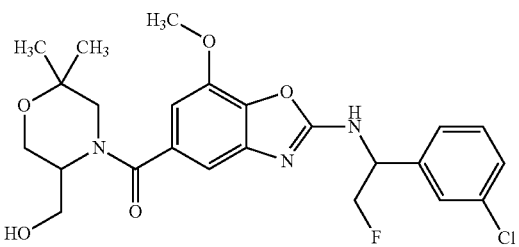 [SMILES: COc1cc(C(=O)N2CC(C)(C)OCC2CO)cc2nc(NC(CF)c3cccc(Cl)c3)oc12]

Diastereomer separation on a chiral phase of 50.0 mg of the compound from Example 4 according to Method 4D gave, after re-purification by preparative RP-HPLC (acetonitrile/water), 16.2 mg of Example 5 (enantiomerically pure isomer 1) and 22.1 mg of Example 6 (enantiomerically pure isomer 2).

HPLC (Method 4E): $R_t$=6.50 min, >96.6% de;
LC-MS (Method 1A): $R_t$=0.95 min; MS (ESIpos): m/z=492 [M+H]$^+$.

Example 7

(2-{[1-(3-Chlorophenyl)-2-fluoroethyl]amino}-7-methoxy-1,3-benzoxazol-5-yl)[(5R)-2,5-dimethylmorpholin-4-yl]methanone [enantiomerically pure isomer 2]

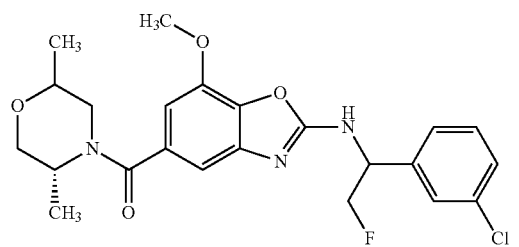 [SMILES: COc1cc(C(=O)N2CC(C)OC[C@H]2C)cc2nc(NC(CF)c3cccc(Cl)c3)oc12]

100 mg (0.130 mmol, purity: 46%) of 2-{[1-(3-chlorophenyl)-2-fluoroethyl]amino}-7-methoxy-1,3-benzoxazole-5-carboxylic acid [enantiomerically pure isomer] and 23.0 mg (0.150 mmol) of (5R)-2,5-dimethylmorpholine hydrochloride [enantiomerically pure isomer 2] were initially charged in N,N-dimethylformamide (1.00 ml), and 65.3 mg (88.1 µl, 0.510 mmol) of N,N-diisopropylethylamine were added. Subsequently, 57.7 mg (0.150 mmol) of HATU were added at RT and the mixture was stirred overnight. Without further work-up, the reaction solution was then purified by preparative RP-HPLC (acetonitrile/water). Yield: 25.1 mg (40% of theory).

LC-MS (Method 1A): $R_t$=1.01 min; MS (ESIpos): m/z=462 [M+H]$^+$;

¹H-NMR (400 MHz, DMSO-d₆): δ [ppm]=9.00 (d, 1H), 7.58 (s, 1H), 7.49-7.35 (m, 3H), 6.84 (br. s., 1H), 6.71 (br. s., 1H), 5.24 (m_c, 1H), 4.79-4.08 (m, 3H), 3.92 (s, 3H), 3.72-3.21 (m, 5H), 1.32-0.90 (m, 6H).

Example 8

(2-{[(1-(3-Chlorophenyl)-2-fluoroethyl]amino}-7-methoxy-1,3-benzoxazol-5-yl)[(5R)-2,5-dimethyl-morpholin-4-yl]methanone [enantiomerically pure isomer 1]

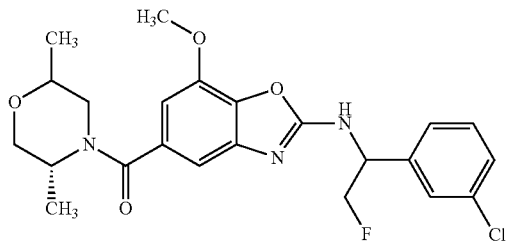 [SMILES: COc1cc(C(=O)N2CC(C)OC[C@H]2C)cc2nc(NC(CF)c3cccc(Cl)c3)oc12]

100 mg (0.130 mmol, purity: 46%) of 2-{[1-(3-chlorophenyl)-2-fluoroethyl]amino}-7-methoxy-1,3-benzoxazole-5-carboxylic acid [enantiomerically pure isomer] and 23.0 mg (0.150 mmol) of (5R)-2,5-dimethylmorpholine hydrochloride [enantiomerically pure isomer 1] were initially charged in N,N-dimethylformamide (1.00 ml), and 65.3 mg (88.1 µl, 0.510 mmol) of N,N-diisopropylethylamine were added. Subsequently, 57.7 mg (0.150 mmol) of HATU were added at RT and the mixture was stirred overnight. Without further work-up, the reaction solution was purified by preparative RP-HPLC (acetonitrile/water).

Yield: 27.4 mg (44% of theory).

LC-MS (Method 1A): R_t=0.99 min; MS (ESIpos): m/z=462 [M+H]⁺;

¹H-NMR (400 MHz, DMSO-d₆): δ [ppm]=9.00 (d, 1H), 7.58 (s, 1H), 7.50-7.34 (m, 3H), 6.83 (s, 1H), 6.69 (s, 1H), 5.24 (m_c, 1H), 4.81-4.52 (m, 2H), 4.04 (br. s., 1H), 3.97-3.88 (s, 4H), 3.84 (dd, 1H), 3.50 (d, 1H), 3.37 (dd, 1H), 3.27 (d, 1H), 1.23 (d, 3H), 1.15 (d, 3H).

Example 9

(2-{[1-(3-Chlorophenyl)-2-fluoroethyl]amino}-7-methoxy-1,3-benzoxazol-5-yl)[(5R)-2-(2-hydroxy-ethyl)-2,5-dimethylmorpholin-4-yl]methanone [1:1 diastereomer mixture, 2 isomers]

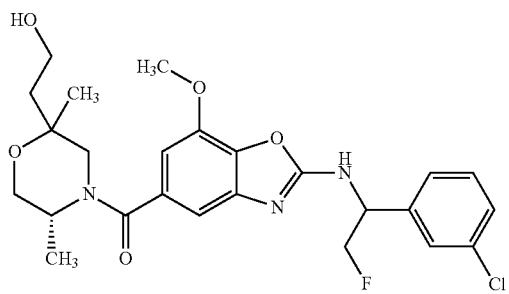 [SMILES: COc1cc(C(=O)N2CC(C)(CCO)OC[C@H]2C)cc2nc(NC(CF)c3cccc(Cl)c3)oc12]

120 mg (0.250 mmol, purity: 77%) of 2-{[1-(3-chlorophenyl)-2-fluoroethyl]amino}-7-methoxy-1,3-benzoxazole-5-carboxylic acid [racemate] and 48.4 mg (0.300 mmol) of 2-[(5R)-2,5-dimethylmorpholin-2-yl]ethanol [Example 31A, enantiomerically pure isomer] were initially charged in N,N-dimethylformamide (1.17 ml), and 115 mg (154 µl, 0.890 mmol) of N,N-diisopropylethylamine were added. 116 mg (0.300 mmol) of HATU were then added at RT, and the mixture was stirred for 2 h. Without further work-up, the reaction solution was purified by preparative RP-HPLC (acetonitrile/water). Yield: 112 mg (84% of theory).

LC-MS (Method 1A): R_t=0.93 min; MS (ESIpos): m/z=506 [M+H]⁺;

¹H-NMR (400 MHz, DMSO-d₆): δ [ppm]=9.00 (dd, 1H), 7.58 (br. s., 1H), 7.50-7.32 (m, 3H), 6.82 (br. s., 1H), 6.67 (s, 1H), 5.24 (m_c, 1H), 4.80-4.52 (m, 2H), 4.31 (t, 1H), 3.92 (s, 3H), 3.73 (d, 1H), 2.96 (br. s., 0.5H), 2.02 (m_c, 1H), 1.43 (br. s., 0.5H), 1.29-1.02 (m, 6H), six protons obscured.

Example 10

(2-{[1-(3-Chlorophenyl)-2-fluoroethyl]amino}-7-methoxy-1,3-benzoxazol-5-yl)[(5R)-2-(2-hydroxy-ethyl)-2,5-dimethylmorpholin-4-yl]methanone [enantiomerically pure isomer 1]

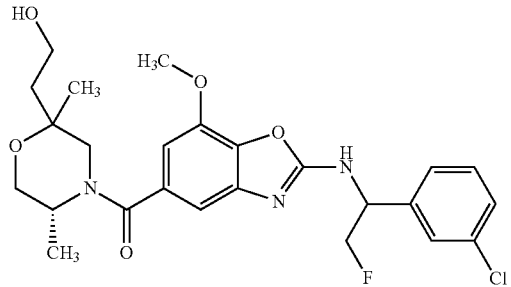 [SMILES: COc1cc(C(=O)N2CC(C)(CCO)OC[C@H]2C)cc2nc(NC(CF)c3cccc(Cl)c3)oc12]

Diastereomer separation on a chiral phase of 102 mg of the compound from Example 9 according to Method 2D gave, after re-purification by preparative RP-HPLC (acetonitrile/water), 24.7 mg of the target compound of Example 10 (enantiomerically pure isomer 1) and 24.0 mg of the target compound of Example 11 (enantiomerically pure isomer 2).

HPLC (Method 2E): R_t=13.6 min, >99.0% de;

LC-MS (Method 1A): R_t=0.93 min; MS (ESIpos): m/z=506 [M+H]⁺;

¹H-NMR (400 MHz, DMSO-d₆): δ [ppm]=9.00 (d, 1H), 7.59 (s, 1H), 7.51-7.36 (m, 3H), 6.83 (s, 1H), 6.67 (s, 1H), 5.24 (m_c, 1H), 4.80-4.52 (m, 2H), 4.32 (t, 1H), 3.92 (s, 3H), 3.73 (dd, 1H), 2.96 (br. s., 0.5H), 2.00 (m_c, 1H), 1.43 (br. s., 0.5H), 1.26-1.02 (m, 6H), six protons obscured.

Example 11

(2-{[1-(3-Chlorophenyl)-2-fluoroethyl]amino}-7-methoxy-1,3-benzoxazol-5-yl)[(5R)-2-(2-hydroxyethyl)-2,5-dimethylmorpholin-4-yl]methanone [enantiomerically pure isomer 2]

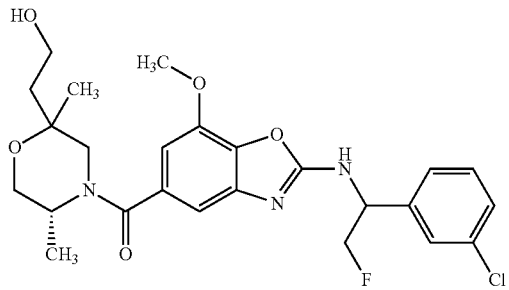 [SMILES: COc1cc(C(=O)N2CC(C)(CCO)OC[C@H]2C)cc2nc(NC(CF)c3cccc(Cl)c3)oc12]

Diastereomer separation on a chiral phase of 102 mg of the compound from Example 9 according to Method 2D gave, after re-purification by preparative RP-HPLC (acetonitrile/water), 24.7 mg of the target compound of Example 10 (enantiomerically pure isomer 1) and 24.0 mg of the target compound of Example 11 (enantiomerically pure isomer 2).

HPLC (Method 2E): $R_t$=15.6 min, 98.5% de;

LC-MS (Method 1A): $R_t$=0.93 min; MS (ESIpos): m/z=506 [M+H]$^+$;

$^1$H-NMR (400 MHz, DMSO-$d_6$): δ [ppm]=9.01 (br. s., 1H), 7.58 (s, 1H), 7.51-7.29 (m, 3H), 6.81 (s, 1H), 6.67 (s, 1H), 5.24 (br. d., 1H), 4.86-4.48 (m, 2H), 4.32 (t, 1H), 3.92 (s, 3H), 3.73 (dd, 1H), 2.96 (br. s., 0.5H), 2.00 ($m_c$, 1H), 1.43 (br. s., 0.5H), 1.21 (d, 3H), 1.07 (br. s., 3H), six protons obscured.

Example 12

(2-{[1-(3-Chlorophenyl)-2-fluoroethyl]amino}-7-methoxy-1,3-benzoxazol-5-yl)[(5R)-2-(2-hydroxypropyl)-2,5-dimethylmorpholin-4-yl]methanone [1:1 diastereomer mixture, 2 isomers]

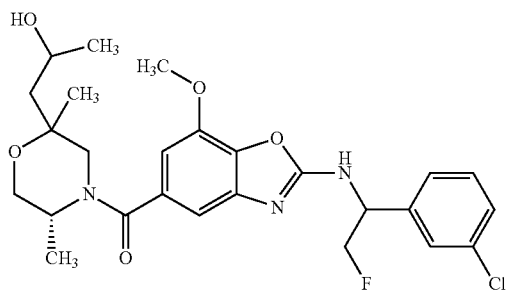 [SMILES: COc1cc(C(=O)N2CC(C)(CC(C)O)OC[C@H]2C)cc2nc(NC(CF)c3cccc(Cl)c3)oc12]

270 mg (0.170 mmol, purity: 23%) of 2-{[1-(3-chlorophenyl)-2-fluoroethyl]amino}-7-methoxy-1,3-benzoxazole-5-carboxylic acid [racemate] and 35.8 mg (0.210 mmol) of 1-[(5R)-2,5-dimethylmorpholin-2-yl]propan-2-ol [Example 34A, enantiomerically pure isomer] were initially charged in N,N-dimethylformamide (793 μl), and 78.0 mg (105 μl, 0.600 mmol) of N,N-diisopropylethylamine were added. Subsequently, 78.6 mg (0.210 mmol) of HATU were added at RT and the mixture was stirred overnight. Without further work-up, the reaction solution was purified by preparative RP-HPLC (acetonitrile/water). The crude product obtained (20.0 mg) was re-purified by Method 1E. This gave 9.0 mg of the target compound (10% of theory).

LC-MS (Method 1A): $R_t$=0.98 min; MS (ESIpos): m/z=520 [M+H]$^+$;

$^1$H-NMR (400 MHz, DMSO-$d_6$): δ [ppm]=8.97 (dd, 1H), 7.58 (br. s., 1H), 7.50-7.33 (m, 3H), 6.81 (d, 1H), 6.67 (s, 1H), 5.24 ($m_c$, 1H), 4.81-4.52 (m, 2H), 4.22 (d, 1H), 3.92 (s, 3H), 3.70 (d, 2H), 2.97 (br. s., 1H), 1.96-1.85 (m, 1H), 1.35-1.01 (m, 10H), three protons obscured.

Example 13

(2-{[1-(3-Chlorophenyl)-2-fluoroethyl]amino}-7-methoxy-1,3-benzoxazol-5-yl)[5-(2-hydroxyethyl)-2-methylmorpholin-4-yl]methanone [1:1 diastereomer mixture, 2 isomers]

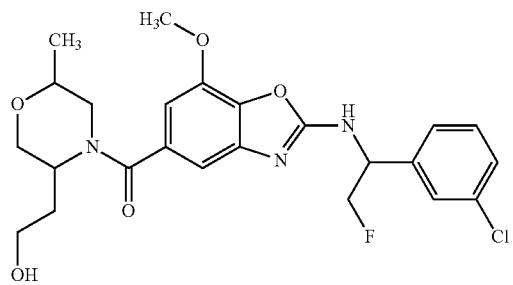 [SMILES: COc1cc(C(=O)N2CC(C)OCC2CCO)cc2nc(NC(CF)c3cccc(Cl)c3)oc12]

200 mg (0.25 mmol, purity: 46%) of 2-{[1-(3-chlorophenyl)-2-fluoroethyl]amino}-7-methoxy-1,3-benzoxazole-5-carboxylic acid [enantiomerically pure isomer] and 44.0 mg (0.30 mmol) of 2-(6-methylmorpholin-3-yl)ethanol [racemate] were initially charged in N,N-dimethylformamide (2.00 ml), and 131 mg (176 μl, 1.01 mmol) of N,N-diisopropylethylamine were added. 115 mg (0.30 mmol) of HATU were then added at RT, and the mixture was stirred for 1 h. A further 22.0 mg (0.15 mmol) of 2-(6-methylmorpholin-3-yl)ethanol [racemate], 65.5 mg (88 μl, 0.51 mmol) of N,N-diisopropylethylamine and 57.5 mg (0.15 mmol) of HATU were added, and the mixture was subsequently stirred at RT overnight. Without further work-up, the reaction solution was purified by preparative RP-HPLC (acetonitrile/water). Yield: 131 mg (97% of theory).

LC-MS (Method 1A): $R_t$=0.90 min; MS (ESIpos): m/z=492 [M+H]$^+$;

$^1$H-NMR (400 MHz, DMSO-$d_6$): δ [ppm]=8.99 (br. d., 1H), 7.58 (s, 1H), 7.49-7.35 (m, 3H), 6.84 (br. s., 1H), 6.71 (br. s., 1H), 5.24 ($m_c$, 1H), 4.82-4.13 (m, 4H), 3.92 (s, 3H), 3.83-3.22 (m, 6H), 3.06-2.60 (m, 1H), 1.98-1.73 (m, 2H), 1.22-0.87 (m, 3H).

Example 14

(2-{[1-(3-Chlorophenyl)-2-fluoroethyl]amino}-7-methoxy-1,3-benzoxazol-5-yl)[(5R)-5-(2-hydroxyethyl)-2-methylmorpholin-4-yl]methanone [enantiomerically pure isomer 1]

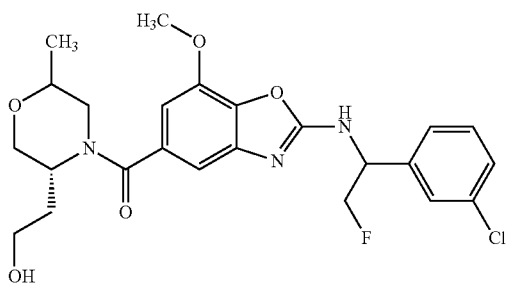 [SMILES: COc1cc(C(=O)N2CC(C)OC[C@H]2CCO)cc2nc(NC(CF)c3cccc(Cl)c3)oc12]

Diastereomer separation on a chiral phase of 120 mg of the compound from Example 13 according to Method 3D gave 55.9 mg of Example 14 (enantiomerically pure isomer 1) and 56.2 mg of Example 15 (enantiomerically pure isomer 2).

HPLC (Method 3E): $R_t$=8.39 min, 99.9% de;
LC-MS (Method 1A): $R_t$=0.94 min; MS (ESIpos): m/z=492 [M+H]$^+$;
$^1$H-NMR (400 MHz, DMSO-d$_6$): δ [ppm]=8.99 (br. d., 1H), 7.58 (s, 1H), 7.50-7.30 (m, 3H), 6.84 (br. s., 1H), 6.71 (br. s., 1H), 5.23 (m$_c$, 1H), 4.80-4.14 (m, 4H), 3.92 (s, 3H), 3.83-3.22 (m, 6H), 3.03-2.60 (m, 1H), 2.01-1.75 (m, 2H), 1.19-0.91 (m, 3H).

Example 15

(2-{[1-(3-Chlorophenyl)-2-fluoroethyl]amino}-7-methoxy-1,3-benzoxazol-5-yl)[(5S)-5-(2-hydroxyethyl)-2-methylmorpholin-4-yl]methanone [enantiomerically pure isomer 2]

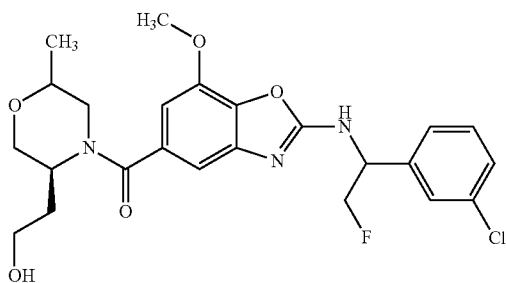 [SMILES: COc1cc(C(=O)N2CC(C)OC[C@@H]2CCO)cc2nc(NC(CF)c3cccc(Cl)c3)oc12]

Method 1:
Diastereomer separation on a chiral phase of 120 mg of the compound from Example 13 according to Method 3D gave 55.9 mg of Example 14 (enantiomerically pure isomer 1) and 56.2 mg of Example 15 (enantiomerically pure isomer 2).

HPLC (Method 3E): $R_t$=16.2 min, 99.9% de;
LC-MS (Method 1A): $R_t$=0.93 min; MS (ESIpos): m/z=492 [M+H]$^+$;
$^1$H-NMR (400 MHz, DMSO-d$_6$): δ [ppm]=9.06-8.92 (m, 1H), 7.58 (s, 1H), 7.50-7.35 (m, 3H), 6.89-6.83 (m, 1H), 6.70 (br. s., 1H), 5.24 (m$_c$, 1H), 4.82-4.14 (m, 4H), 3.92 (s, 3H), 3.83-3.21 (m, 6H), 3.05-2.59 (m, 1H), 2.01-1.70 (m, 2H), 1.21-0.90 (m, 3H).

Method 2:
500 mg (1.23 mmol, purity: 89%) of 2-{[1-(3-chlorophenyl)-2-fluoroethyl]amino}-7-methoxy-1,3-benzoxazole-5-carboxylic acid [Example 13A, enantiomerically pure isomer] and 232 mg (1.60 mmol) of 2-[(3S)-6-methylmorpholin-3-yl]ethanol [Example 42A, enantiomerically pure isomer] were initially charged in N,N-dimethylformamide (20.0 ml), and 477 mg (643 μl, 3.69 mmol) of N,N-diisopropylethylamine were added. 654 mg (1.72 mmol) of HATU were added at RT, and the mixture was stirred for 14 h and then purified without any further work-up by preparative RP-HPLC (acetonitrile/water). Traces of the minor isomer were removed by HPLC on a chiral phase according to Method 3D from the product obtained. Yield: 423 mg (70% of theory).

Optical rotation: $[\alpha]_D^{20}$=63.79° (c=0.625, chloroform);
HPLC (Method 3E): $R_t$=14.0 min, 99.9% de;
LC-MS (Method 1A): $R_t$=0.93 min; MS (ESIpos): m/z=492 [M+H]$^+$;
$^1$H-NMR (400 MHz, DMSO-d$_6$): δ [ppm]=9.04-8.94 (m, 1H), 7.58 (s, 1H), 7.50-7.35 (m, 3H), 6.90-6.81 (m, 1H), 6.70 (br. s., 1H), 5.24 (m$_c$, 1H), 4.84-4.12 (m, 4H), 3.92 (s, 3H), 3.84-3.19 (m, 6H), 3.07-2.59 (m, 1H), 2.03-1.71 (m, 2H), 1.21-0.90 (m, 3H).

According to structure determination by complex formation of human α-thrombin with Example 15 in the crystal, this compound is (2-{[(1S)-1-(3-chlorophenyl)-2-fluoroethyl]amino}-7-methoxy-1,3-benzoxazol-5-yl)[(2S,5S)-5-(2-hydroxyethyl)-2-methylmorpholin-4-yl]methanone having the formula below

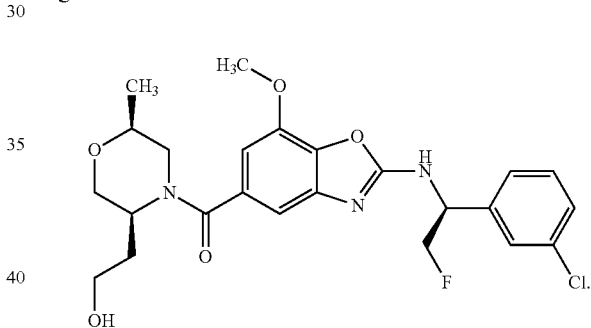

Example 16

(2-{[1-(3-Chlorophenyl)-2-fluoroethyl]amino}-7-methoxy-1,3-benzoxazol-5-yl)[5-(3-hydroxycyclobutyl)-2-methylmorpholin-4-yl]methanone [diastereomer mixture, 4 isomers]

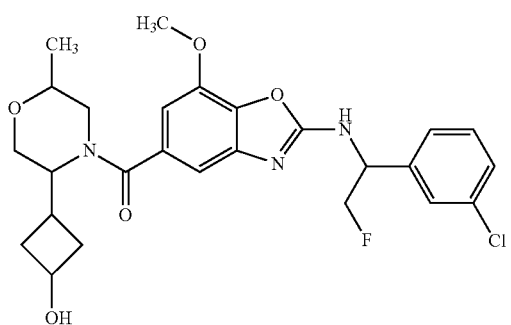 [SMILES: COc1cc(C(=O)N2CC(C)OCC2C2CC(O)C2)cc2nc(NC(CF)c3cccc(Cl)c3)oc12]

200 mg (0.33 mmol, purity: 60%) of 2-{[1-(3-chlorophenyl)-2-fluoroethyl]amino}-7-methoxy-1,3-benzoxazole-5-carboxylic acid [enantiomerically pure isomer] and 67.6 mg (0.40 mmol) of 3-(6-methylmorpholin-3-yl)cyclobutanol [diastereomer mixture, 4 isomers] were initially charged in N,N-dimethylformamide (2.50 ml), and 170 mg (229 µl, 1.32 mmol) of N,N-diisopropylethylamine were added. 150 mg (0.40 mmol) of HATU were then added at RT, and the mixture was stirred for 2 h. Without further work-up, the reaction solution was then purified by preparative RP-HPLC (acetonitrile/water). Yield: 83.9 mg (48% of theory).

LC-MS (Method 1A): $R_t$=0.94, 0.95 min; MS (ESIpos): m/z=518 [M+H]$^+$.

Example 17

(2-{[1-(3-Chlorophenyl)-2-fluoroethyl]amino}-7-methoxy-1,3-benzoxazol-5-yl)[5-(3-hydroxycyclobutyl)-2-methylmorpholin-4-yl]methanone [enantiomerically pure isomer 1]

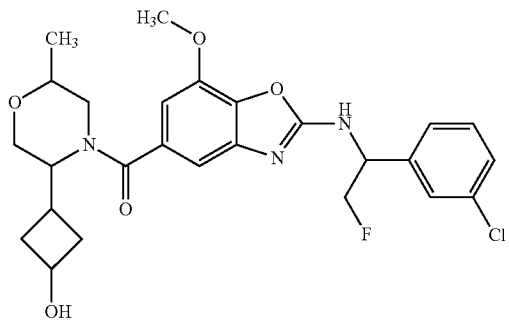 [SMILES: COc1cc(C(=O)N2CC(C)OCC2C2CC(O)C2)cc2nc(NC(CF)c3cccc(Cl)c3)oc12]

Diastereomer separation on a chiral phase of 75.0 mg of the compound from Example 16 according to Method 1D gave 17.4 mg of Example 17 (enantiomerically pure isomer 1), 8.6 mg of Example 18 (enantiomerically pure isomer 2), 17.7 mg of Example 19 (enantiomerically pure isomer 3) and 9.5 mg of Example 20 (enantiomerically pure isomer 4).

HPLC (Method 1E): $R_t$=11.1 min, >99% de;

LC-MS (Method 1A): $R_t$=0.95 min; MS (ESIpos): m/z=518 [M+H]$^+$.

Example 18

(2-{[1-(3-Chlorophenyl)-2-fluoroethyl]amino}-7-methoxy-1,3-benzoxazol-5-yl)[5-(3-hydroxycyclobutyl)-2-methylmorpholin-4-yl]methanone [enantiomerically pure isomer 2]

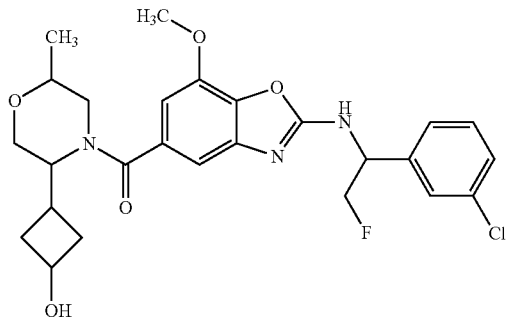 [SMILES: COc1cc(C(=O)N2CC(C)OCC2C2CC(O)C2)cc2nc(NC(CF)c3cccc(Cl)c3)oc12]

Diastereomer separation on a chiral phase of 75.0 mg of the compound from Example 16 according to Method 1D gave 17.4 mg of Example 17 (enantiomerically pure isomer 1), 8.6 mg of Example 18 (enantiomerically pure isomer 2), 17.7 mg of Example 19 (enantiomerically pure isomer 3) and 9.5 mg of Example 20 (enantiomerically pure isomer 4).

HPLC (Method 1E): $R_t$=12.6 min, 94.3:5.7 dr;

LC-MS (Method 1A): $R_t$=0.95 min; MS (ESIpos): m/z=518 [M+H]$^+$.

Example 19

(2-{[1-(3-Chlorophenyl)-2-fluoroethyl]amino}-7-methoxy-1,3-benzoxazol-5-yl)[5-(3-hydroxycyclobutyl)-2-methylmorpholin-4-yl]methanone [enantiomerically pure isomer 3]

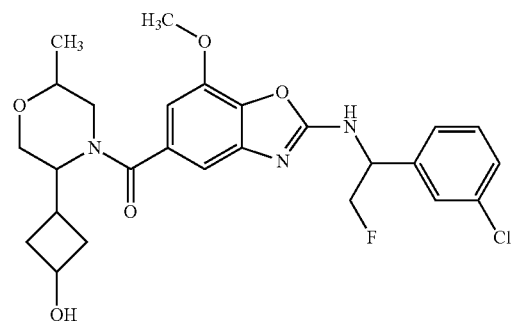 [SMILES: COc1cc(C(=O)N2CC(C)OCC2C2CC(O)C2)cc2nc(NC(CF)c3cccc(Cl)c3)oc12]

Diastereomer separation on a chiral phase of 75.0 mg of the compound from Example 16 according to Method 1D gave 17.4 mg of Example 17 (enantiomerically pure isomer 1), 8.6 mg of Example 18 (enantiomerically pure isomer 2), 17.7 mg of Example 19 (enantiomerically pure isomer 3) and 9.5 mg of Example 20 (enantiomerically pure isomer 4).

HPLC (Method 1E): $R_t$=14.5 min, >99% de;

LC-MS (Method 1A): $R_t$=0.95 min; MS (ESIpos): m/z=518 [M+H]$^+$.

Example 20

(2-{[1-(3-Chlorophenyl)-2-fluoroethyl]amino}-7-methoxy-1,3-benzoxazol-5-yl)[5-(3-hydroxycyclobutyl)-2-methylmorpholin-4-yl]methanone [enantiomerically pure isomer 4]

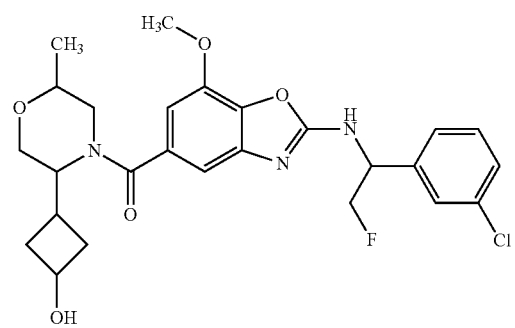 [SMILES: COc1cc(C(=O)N2CC(C)OCC2C2CC(O)C2)cc2nc(NC(CF)c3cccc(Cl)c3)oc12]

Diastereomer separation on a chiral phase of 75.0 mg of the compound from Example 16 according to Method 1D gave 17.4 mg of Example 17 (enantiomerically pure isomer 1), 8.6 mg of Example 18 (enantiomerically pure isomer 2), 17.7 mg of Example 19 (enantiomerically pure isomer 3) and 9.5 mg of Example 20 (enantiomerically pure isomer 4).

HPLC (Method 1E): $R_t$=17.2 min, 96.1:3.9 dr;

LC-MS (Method 1A): $R_t$=0.94 min; MS (ESIpos): m/z=518 [M+H]$^+$.

Example 21

(2-{[1-(3-Chlorophenyl)-2-fluoroethyl]amino}-7-methoxy-1,3-benzoxazol-5-yl)(cis-2-hydroxy-7-methyl-8-oxa-5-azaspiro[3.5]non-5-yl)methanone [enantiomerically pure isomer 1]

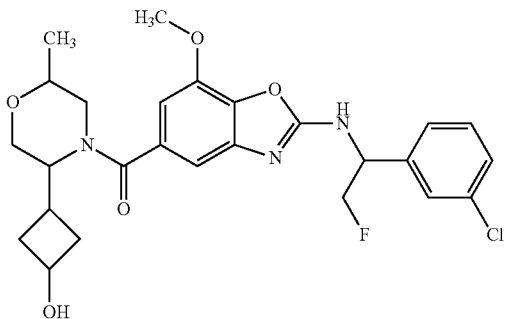 [SMILES: COc1cc(C(=O)N2CC(C)OCC2C2CC(O)C2)cc2nc(NC(CF)c3cccc(Cl)c3)oc12]

120 mg (0.152 mmol, purity: 46%) of 2-{[1-(3-chlorophenyl)-2-fluoroethyl]amino}-7-methoxy-1,3-benzoxazole-5-carboxylic acid [enantiomerically pure isomer] and 35.2 mg (0.182 mmol) of cis-7-methyl-8-oxa-5-azaspiro[3.5]nonan-2-ol hydrochloride [Example 64A, enantiomerically pure isomer 1] were initially charged in N,N-dimethylformamide (1.20 ml), and 78.4 mg (106 μl, 0.607 mmol) of N,N-diisopropylethylamine were added. 69.2 mg (0.182 mmol) of HATU were then added, and the mixture was stirred at RT for 1 h. 35.2 mg (0.182 mmol) of cis-7-methyl-8-oxa-5-azaspiro[3.5]nonan-2-ol hydrochloride [Example 64A, enantiomerically pure isomer 1], 78.4 mg (106 μL, 0.607 mmol) of N,N-diisopropylethylamine and 69.2 mg (0.182 mmol) of HATU were then added, and the mixture was stirred at RT for a further 2 h. Without further work-up, the reaction solution was purified by preparative RP-HPLC (acetonitrile/water). Yield: 67.3 mg (80% of theory).

LC-MS (Method 1A): $R_t$=0.91 min; MS (ESIpos): m/z=504 [M+H]$^+$;

$^1$H-NMR (400 MHz, DMSO-d$_6$): δ [ppm]=9.00 (d, 1H), 7.58 (s, 1H), 7.51-7.34 (m, 3H), 6.93 (s, 1H), 6.78 (s, 1H), 5.24 (m$_c$, 1H), 5.08 (d, 1H), 4.80-4.51 (m, 2H), 3.93 (s, 3H), 3.89-3.80 (m, 1H), 3.62 (d, 1H), 3.52-3.43 (m, 2H), 2.90 (dd, 1H), 2.73-2.63 (m, 1H), 2.33 (br. s., 1H), 2.21-2.10 (m, 1H), 1.85 (br. t., 1H), 0.90 (d, 3H).

Example 22

(2-{[1-(3-Chlorophenyl)-2-fluoroethyl]amino}-7-methoxy-1,3-benzoxazol-5-yl)(cis-2-hydroxy-7-methyl-8-oxa-5-azaspiro[3.5]non-5-yl)methanone [enantiomerically pure isomer 2]

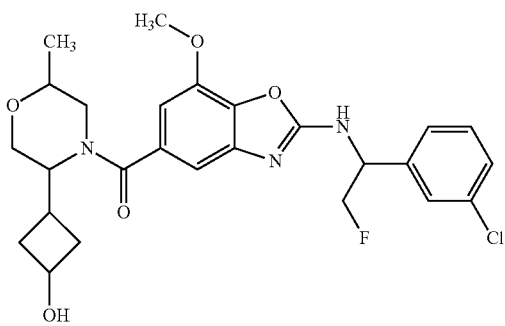 [SMILES: COc1cc(C(=O)N2CC(C)OCC2C2CC(O)C2)cc2nc(NC(CF)c3cccc(Cl)c3)oc12]

120 mg (0.152 mmol, purity: 46%) of 2-{[1-(3-chlorophenyl)-2-fluoroethyl]amino}-7-methoxy-1,3-benzoxazole-5-carboxylic acid [enantiomerically pure isomer] and 35.2 mg (0.182 mmol) of cis-7-methyl-8-oxa-5-azaspiro[3.5]nonan-2-ol hydrochloride [Example 65A, enantiomerically pure isomer 2] were initially charged in N,N-dimethylformamide (1.20 ml), and 78.4 mg (106 μl, 0.607 mmol) of N,N-diisopropylethylamine were added. 69.2 mg (0.182 mmol) of HATU were then added, and the mixture was stirred at RT for 1 h. 35.2 mg (0.182 mmol) of cis-7-methyl-8-oxa-5-azaspiro[3.5]nonan-2-ol hydrochloride [Example 65A, enantiomerically pure isomer 2], 78.4 mg (106 μL, 0.607 mmol) of N,N-diisopropylethylamine and 69.2 mg (0.182 mmol) of HATU were then added, and the mixture was stirred at RT for a further 2 h. Without further work-up, the reaction solution was purified by preparative RP-HPLC (acetonitrile/water). Yield: 44.2 mg (51% of theory).

LC-MS (Method 1A): $R_t$=0.94 min; MS (ESIpos): m/z=504 [M+H]$^+$;

$^1$H-NMR (400 MHz, DMSO-d$_6$): δ [ppm]=9.01 (d, 1H), 7.58 (s, 1H), 7.49-7.36 (m, 3H), 6.92 (s, 1H), 6.80 (s, 1H), 5.24 (m$_c$, 1H), 5.09 (d, 1H), 4.80-4.52 (m, 2H), 3.93 (s, 3H), 3.90-3.80 (m, 1H), 3.62 (d, 1H), 3.51-3.42 (m, 2H), 2.90 (dd, 1H), 2.69 (dd, 1H), 2.38-2.29 (d, 1H), 2.22-2.13 (m, 1H), 1.84 (br. t., 1H), 0.89 (d, 3H).

Example 23

4-[(2-{[1-(3-Chlorophenyl)-2-fluoroethyl]amino}-7-methoxy-1,3-benzoxazol-5-yl)carbonyl]-3-methyl-1,4-diazabicyclo[4.2.0]octan-2-one [enantiomerically pure isomer]

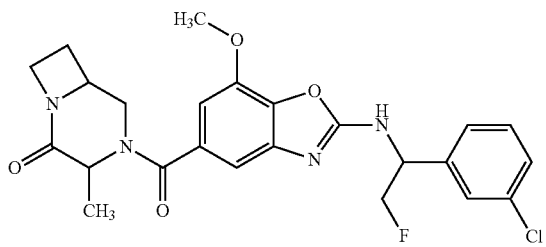 [SMILES: COc1cc(C(=O)N2CC3CCN3C(=O)C2C)cc2nc(NC(CF)c3cccc(Cl)c3)oc12]

266 mg (0.337 mmol, purity: 46%) of 2-{[1-(3-chlorophenyl)-2-fluoroethyl]amino}-7-methoxy-1,3-benzoxazole-5-carboxylic acid [enantiomerically pure isomer] and 154 mg (1.10 mmol) of 3-methyl-1,4-diazabicyclo[4.2.0]octan-2-one [Example 70A, enantiomerically pure isomer 3] were initially charged in N,N-dimethylformamide (3.32 ml), and 378 mg (0.51 ml, 2.92 mmol) of N,N-diisopropylethylamine were added. Subsequently, 333 mg (0.877 mmol) of HATU were added at RT and the mixture was stirred overnight. Without further work-up, the reaction solution was purified by preparative RP-HPLC (acetonitrile/water). Yield: 174 mg (quant.).

LC-MS (Method 1A): $R_t$=0.94 min; MS (ESIpos): m/z=487 [M+H]$^+$;

$^1$H-NMR (400 MHz, DMSO-d$_6$): δ [ppm]=9.00 (d, 1H), 7.58 (s, 1H), 7.50-7.36 (m, 3H), 6.91 (s, 1H), 6.77 (s, 1H), 5.24 (m$_c$, 1H), 4.80-4.52 (m, 3H), 4.22 (m$_c$, 1H), 4.05 (m$_c$, 1H), 3.98-3.87 (m, 4H), 3.72 (m, 1H), 2.45-2.31 (m, 1H), 2.10-2.00 (m, 1H), 1.38 (d, 3H), one proton obscured.

Example 24

{(3S)-4-[(2-{[1-(3-Chlorophenyl)-2-fluoroethyl]amino}-7-methoxy-1,3-benzoxazol-5-yl)carbonyl]-6-methylmorpholin-3-yl}acetic acid [enantiomerically pure isomer]

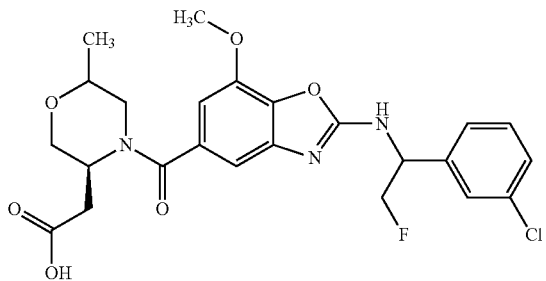 [SMILES: COc1cc(C(=O)N2CC(C)OC[C@@H]2CC(=O)O)cc2nc(NC(CF)c3cccc(Cl)c3)oc12]

600 mg (1.22 mmol) of (2-{[1-(3-chlorophenyl)-2-fluoroethyl]amino}-7-methoxy-1,3-benzoxazol-5-yl)[(5S)-5-(2-hydroxyethyl)-2-methylmorpholin-4-yl]methanone [Example 15, enantiomeric ally pure isomer 2] were initially charged in acetonitrile (120 ml), 611 mg (2.68 mmol) of periodic acid were added at RT and the mixture was stirred for 15 min. The mixture was then cooled to 0° C., and 15.7 mg (0.07 mmol) of pyridinium chlorochromate in acetonitrile (2 ml) were added. The mixture was stirred at 0° C. for 4 h (monitored by TLC: dichloromethane/isopropanol 10:1) and then concentrated under reduced pressure to about 20 ml. Saturated aqueous sodium bisulphite solution (150 ml) was added and the mixture was extracted with ethyl acetate (3×100 ml). The organic phase was washed with 1 N aqueous hydrogen chloride solution (100 ml) and water (100 ml), dried over sodium sulphate, filtered and concentrated under reduced pressure. The residue was purified by preparative RP-HPLC (acetonitrile/water). Yield: 312 mg (48% of theory).

Optical rotation: $[\alpha]_D^{20}$=133.9° (c=0.55, chloroform);
LC-MS (Method 7A): $R_t$=2.65 min; MS (ESIpos): m/z=505 [M+H]$^+$;
$^1$H-NMR (400 MHz, DMSO-d$_6$): δ [ppm]=12.33 (br. s., 1H), 8.99 (d, 1H), 7.58 (s, 1H), 7.50-7.33 (m, 3H), 6.95-6.80 (m, 1H), 6.72 (br. s., 1H), 5.24 (m$_c$, 1H), 4.85-4.15 (m, 3H), 3.91 (s, 3H), 3.83-3.23 (m, 4H), 3.05-2.56 (m, 3H), 1.22-0.91 (m, 3H).

Example 25

(2-{[1-(3-Chlorophenyl)-2-fluoroethyl]amino}-7-methoxy-0,2-benzoxazol-5-yl)[(5R)-5-(2-hydroxyethyl)-2,2-dimethylmorpholin-4-yl]methanone [diastereomer mixture, 2 isomers]

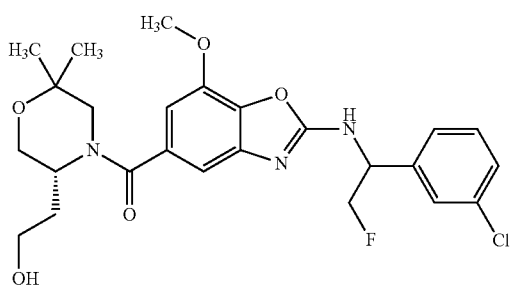 [SMILES: COc1cc(C(=O)N2CC(C)(C)OC[C@H]2CCO)cc2nc(NC(CF)c3cccc(Cl)c3)oc12]

50.0 mg (0.08 mmol, purity: 60%) of 2-{[1-(3-chlorophenyl)-2-fluoroethyl]amino}-7-methoxy-1,3-benzoxazole-5-carboxylic acid [enantiomerically pure isomer] and 15.7 mg (0.10 mmol) of 2-[(3R)-6,6-dimethylmorpholin-3-yl]ethanol [Example 77A, enantiomer mixture, 2 isomers] were initially charged in N,N-dimethylformamide (1.00 ml), and 42.5 mg (57.3 µl, 0.33 mmol) of N,N-diisopropylethylamine were added. 37.5 mg (0.10 mmol) of HATU were then added at RT, and the mixture was stirred for 2 h. Without further work-up, the reaction solution was purified by preparative RP-HPLC (acetonitrile/water).

Yield: 30.7 mg (71% of theory, diastereomer ratio: about 85:15).

HPLC (Method 3E): $R_t$=6.07 min (target compound), 8.46 min (minor isomer): about 85:15 diastereomer ratio;
LC-MS (Method 1A): $R_t$=0.95 min; MS (ESIpos): m/z=506 [M+H]$^+$;
$^1$H-NMR (400 MHz, DMSO-d$_6$): δ [ppm]=9.00 (d, 1H), 7.58 (s, 1H), 7.50-7.35 (m, 3H), 6.82 (br. s., 1H), 6.68 (s, 1H), 5.23 (m$_c$, 1H), 4.85-4.25 (m, 4H), 4.03-3.70 (m, 5H), 3.44 (br. s., 3H), 1.97-1.75 (m, 2H), 1.11 (br. s., 6H), one proton obscured.

Example 26

(2-{[1-(3-Chlorophenyl)-2-fluoroethyl]amino}-7-methoxy-1,3-benzoxazol-5-yl][(4R)-4-ethoxy-2-(hydroxymethyl)pyrrolidin-1-yl]methanone [diastereomer mixture, 2 isomers]

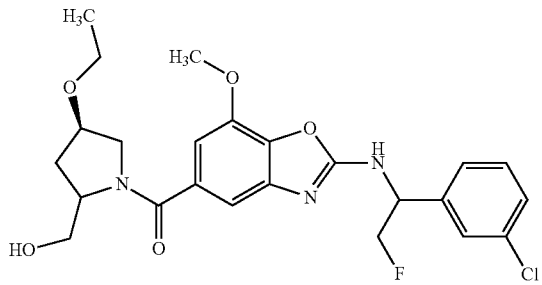 [SMILES: CCO[C@@H]1CC(CO)N(C(=O)c2cc(OC)c3oc(NC(CF)c4cccc(Cl)c4)nc3c2)C1]

200 mg (0.49 mmol, purity: 89%) of 2-{[1-(3-chlorophenyl)-2-fluoroethyl]amino}-7-methoxy-1,3-benzoxazole-5-carboxylic acid [Example 13A, enantiomerically pure isomer] and 106 mg (0.73 mmol) of [(4R)-4-ethoxypyrrolidin-2-yl]methanol [diastereomer mixture, 2 isomers] were initially charged in N,N-dimethylformamide (3.25 ml), and 441 mg (595 µl, 3.42 mmol) of N,N-diisopropylethylamine were added. Subsequently, 223 mg (0.59 mmol) of HATU were added at RT and the mixture was stirred overnight. Without further work-up, the reaction solution was purified by preparative RP-HPLC (acetonitrile/water).

Yield: 192 mg (79% of theory).

LC-MS (Method 1A): $R_t$=0.96 min; MS (ESIpos): m/z=492 [M+H]$^+$;
$^1$H-NMR (400 MHz, DMSO-d$_6$): δ [ppm]=9.03-8.96 (m, 1H), 7.59 (s, 1H), 7.50-7.36 (m, 3H), 7.02-6.94 (m, 1H), 6.87-6.80 (m, 1H), 5.25 (m$_c$, 1H), 4.86-4.51 (m, 3H), 4.24-4.10 (m, 1H), 3.92 (s, 4H), 3.72-3.37 (m, 3H), 3.32-3.11 (m, 2H), 2.23-1.89 (m, 2H), 1.17-0.95 (m, 3H), one proton obscured.

Example 27

(2-{[1-(3-Chlorophenyl)-2-fluoroethyl]amino}-7-methoxy-1,3-benzoxazol-5-yl)[(4R)-4-ethoxy-2-(hydroxymethyl)pyrrolidin-1-yl]methanone [enantiomerically pure isomer 1]

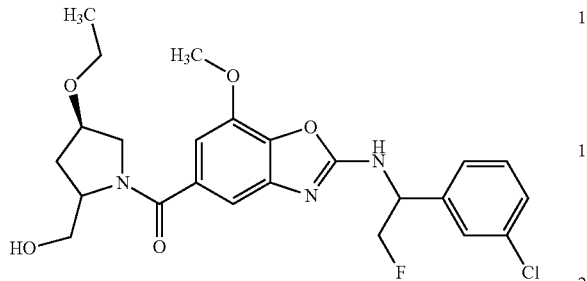

Diastereomer separation on a chiral phase of 192 mg of the compound from Example 26 according to Method 8D gave, after re-purification by preparative RP-HPLC (acetonitrile/water), 27.7 mg of Example 27 (enantiomerically pure isomer 1) and 6.7 mg of Example 28 (enantiomerically pure isomer 2).

HPLC (Method 8E): $R_t$=8.59 min, >99.0% de (enantiomerically pure isomer 1),

LC-MS (Method 1A): $R_t$=0.93 min; MS (ESIpos): m/z=492 [M+H]$^+$;

$^1$H-NMR (400 MHz, DMSO-d$_6$): δ [ppm]=8.99 (br. s., 1H), 7.58 (s, 1H), 7.51-7.35 (m, 3H), 6.97 (s, 1H), 6.83 (s, 1H), 5.24 (m$_c$, 1H), 4.83-4.51 (m, 3H), 4.19 (br. s., 1H), 3.92 (s, 4H), 3.71-3.46 (m, 3H), 3.28-2.97 (m, 2H), 2.09-1.93 (m, 2H), 1.16-0.94 (m, 3H), one proton obscured.

Example 28

(2-{[1-(3-Chlorophenyl)-2-fluoroethyl]amino}-7-methoxy-1,3-benzoxazol-5-yl)[(4R)-4-ethoxy-2-(hydroxymethyl)pyrrolidin-1-yl]methanone [enantiomerically pure isomer 2]

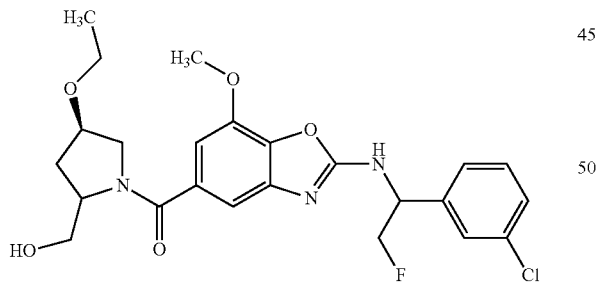

Diastereomer separation on a chiral phase of 192 mg of the compound from Example 26 according to Method 8D gave, after re-purification by preparative RP-HPLC (acetonitrile/water), 27.7 mg of Example 27 (enantiomerically pure isomer 1) and 6.7 mg of Example 28 (enantiomerically pure isomer 2).

HPLC (Method 8E): $R_t$=15.9 min, >99.0% de (enantiomerically pure isomer 2),

LC-MS (Method 1A): $R_t$=0.96 min; MS (ESIpos): m/z=492 [M+H]$^+$;

$^1$H-NMR (400 MHz, DMSO-d$_6$): δ [ppm]=8.99 (br. s., 1H), 7.58 (s, 1H), 7.50-7.35 (m, 3H), 6.96 (s, 1H), 6.81 (s, 1H), 5.24 (m$_c$, 1H), 4.90-4.50 (m, 3H), 4.24-4.07 (m, 1H), 3.92 (s, 5H), 3.65-3.47 (br. s., 3H), 3.24-3.05 (m, 1H), 2.24-1.87 (m, 2H), 1.13-1.01 (m, 3H), one proton obscured.

Example 29

(2-{[1-(3-Chlorophenyl)-2-fluoroethyl]amino}-7-methoxy-1,3-benzoxazol-5-yl)[(4R)-4-ethoxy-2-(2-hydroxyethyl)pyrrolidin-1-yl]methanone [diastereomer mixture, 2 isomers]

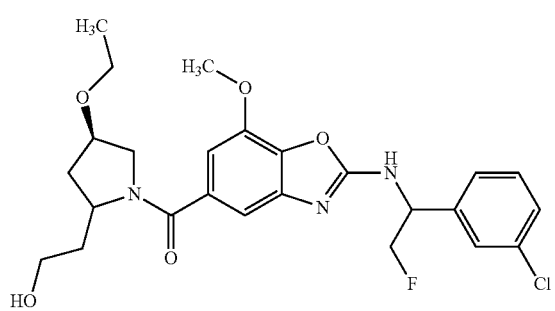 [SMILES: CCO[C@@H]1CC(CCO)N(C(=O)c2cc(OC)c3oc(NC(CF)c4cccc(Cl)c4)nc3c2)C1]

171 mg (0.42 mmol, purity: 89%) of 2-{[1-(3-chlorophenyl)-2-fluoroethyl]amino}-7-methoxy-1,3-benzoxazole-5-carboxylic acid [Example 13A, enantiomerically pure isomer] and 100 mg (0.63 mmol) of 2-[(4R)-4-ethoxypyrrolidin-2-yl]ethanol [diastereomer mixture, 2 isomers] were initially charged in N,N-dimethylformamide (2.79 ml), and 379 mg (511 nl, 2.93 mmol) of N,N-diisopropylethylamine were added. 191 mg (0.50 mmol) of HATU were added at RT, and the mixture was then stirred for 2 h. Without further work-up, the reaction solution was purified by preparative RP-HPLC (acetonitrile/water). Yield: 145 mg (65% of theory).

LC-MS (Method 1A): $R_t$=0.97 min; MS (ESIpos): m/z=506 [M+H]$^+$;

$^1$H-NMR (400 MHz, DMSO-d$_6$): δ [ppm]=9.08-8.94 (m, 1H), 7.59 (s, 1H), 7.52-7.32 (m, 3H), 6.95 (br. s., 1H), 6.80 (d, 1H), 5.24 (m$_c$, 1H), 4.81-4.52 (m, 2H), 4.46 (br. s., 1H), 4.20 (br. s., 1H), 3.97-3.85 (m, 4H), 3.68-3.37 (m, 3H), 3.30-3.10 (m, 2H), 2.23-1.97 (m, 2H), 1.85-1.48 (m, 2H), 1.15-0.90 (m, 3H), one proton obscured.

Example 30

(2-{[1-(3-Chlorophenyl)-2-fluoroethyl]amino}-7-methoxy-1,3-benzoxazol-5-yl)[(4R)-4-ethoxy-2-(2-hydroxyethyl)pyrrolidin-1-yl]methanone [enantiomerically pure isomer 1]

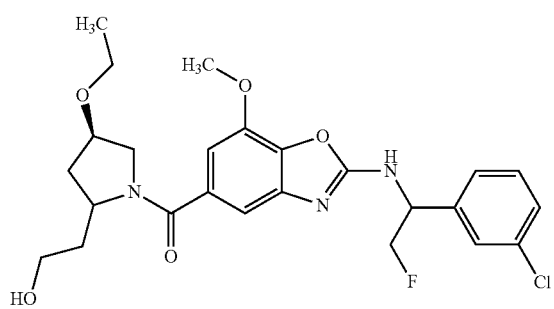 [SMILES: CCO[C@@H]1CC(CCO)N(C(=O)c2cc(OC)c3oc(NC(CF)c4cccc(Cl)c4)nc3c2)C1]

Diastereomer separation on a chiral phase of 140 mg of the compound from Example 29 according to Method 9D gave 31.0 mg of Example 30 (enantiomerically pure isomer 1) and 73 mg of Example 31 (enantiomerically pure isomer 2).

HPLC (Method 9E): R$_t$=8.08 min, >99.0% de (enantiomerically pure isomer 1),

LC-MS (Method 1A): R$_t$=0.98 min; MS (ESIpos): m/z=506 [M+H]$^+$;

$^1$H-NMR (400 MHz, DMSO-d$_6$): δ [ppm]=8.98 (d, 1H), 7.58 (s, 1H), 7.50-7.35 (m, 3H), 6.95 (s, 1H), 6.79 (s, 1H), 5.24 (m$_c$, 1H), 4.81-4.52 (m, 2H), 4.44 (br. s., 1H), 4.20 (br. s., 1H), 3.92 (s, 4H), 3.64-3.35 (m, 5H), 2.27-2.02 (m, 2H), 1.70 (br. s., 2H), 1.06 (t, 3H), one proton obscured.

Example 31

(2-{[1-(3-Chlorophenyl)-2-fluoroethyl]amino}-7-methoxy-1,3-benzoxazol-5-yl)[(4R)-4-ethoxy-2-(2-hydroxyethyl)pyrrolidin-1-yl]methanone [enantiomerically pure isomer 2]

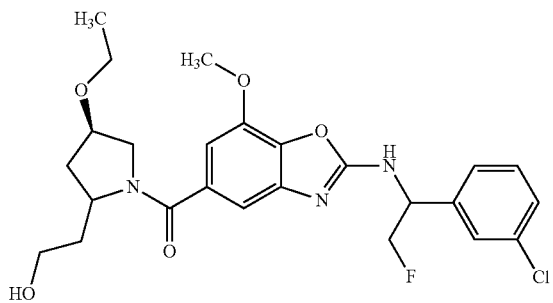 [SMILES: CCO[C@@H]1CC(CCO)N(C(=O)c2cc(OC)c3oc(NC(CF)c4cccc(Cl)c4)nc3c2)C1]

Diastereomer separation on a chiral phase of 140 mg of the compound from Example 29 according to Method 9D gave 31.0 mg of Example 30 (enantiomerically pure isomer 1) and 73 mg of Example 31 (enantiomerically pure isomer 2).

HPLC (Method 9E): R$_t$=10.2 min, >99.0% de (enantiomerically pure isomer 2),

LC-MS (Method 1A): R$_t$=0.96 min; MS (ESIpos): m/z=506 [M+H]$^+$;

$^1$H-NMR (400 MHz, DMSO-d$_6$): δ [ppm]=8.99 (d, 1H), 7.59 (s, 1H), 7.50-7.29 (m, 3H), 6.95 (s, 1H), 6.81 (s, 1H), 5.24 (m$_c$, 1H), 4.85-4.51 (m, 2H), 4.46 (br. s., 1H), 4.20 (br. s., 1H), 3.98-3.84 (m, 4H), 3.59 (d, 3H), 3.29-3.08 (m, 2H), 2.21-1.97 (m, 2H), 1.82-1.72 (br. s., 1H), 1.66-1.47 (m, 1H), 0.99 (t, 3H), one proton obscured.

Example 32

7-[(2-{[1-(3-Chlorophenyl)-2-fluoroethyl]amino}-7-methoxy-1,3-benzoxazol-5-yl)carbonyl]-6-methyl-4,7-diazaspiro[2.5]octan-5-one [diastereomer mixture, 2 isomers]

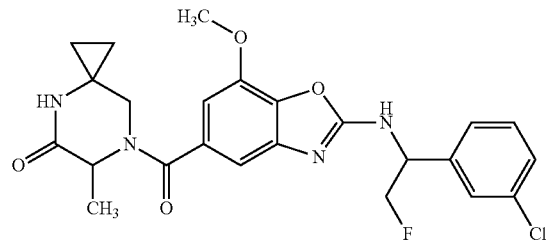 [SMILES: COc1cc(C(=O)N2CC3(CC3)NC(=O)C2C)cc2nc(NC(CF)c3cccc(Cl)c3)oc12]

100 mg (0.24 mmol, purity: 89%) of 2-{[1-(3-chlorophenyl)-2-fluoroethyl]amino}-7-methoxy-1,3-benzoxazole-5-carboxylic acid [Example 13A, enantiomerically pure isomer] and 100 mg (0.37 mmol) of 6-methyl-4,7-diazaspiro[2.5]octan-5-one trifluoroacetate [racemate] were initially charged in N,N-dimethylformamide (1.62 ml), and 221 mg (297 nl, 1.71 mmol) of N,N-diisopropylethylamine were added. 111 mg (0.29 mmol) of HATU were added at RT, and the mixture was then stirred for 2 h. Without further work-up, the reaction solution was purified by preparative RP-HPLC (acetonitrile/water). Yield: 82.6 mg (68% of theory).

LC-MS (Method 1A): R$_t$=0.89 min; MS (ESIpos): m/z=487 [M+H]$^+$;

$^1$H-NMR (400 MHz, DMSO-d$_6$): δ [ppm]=9.02 (dd, 1H), 8.15 (s, 1H), 7.58 (d, 1H), 7.51-7.29 (m, 3H), 6.84 (d, 1H), 6.71 (s, 1H), 5.25 (m$_c$, 1H), 4.96-4.46 (m, 3H), 3.92 (s, 3H), 3.69 (br.s., 1H), 3.21-2.99 (m, 1H), 1.42 (d, 3H), 0.90-0.30 (m, 4H).

Example 33

7-[(2-{[1-(3-Chlorophenyl)-2-fluoroethyl]amino}-7-methoxy-1,3-benzoxazol-5-yl)carbonyl]-6-methyl-4,7-diazaspiro[2.5]octan-5-one [enantiomerically pure isomer 1]

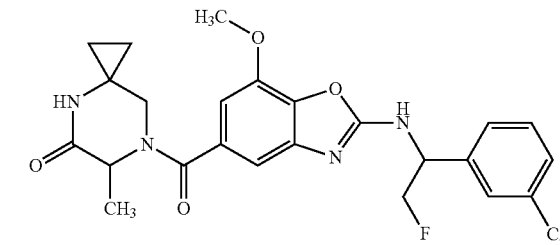

Diastereomer separation on a chiral phase of 75.0 mg of the compound from Example 32 according to Method 10D gave, after re-purification by preparative RP-HPLC (acetonitrile/water), 15.9 mg of Example 33 (enantiomerically pure isomer 1) and 23.5 mg of Example 34 (enantiomerically pure isomer 2).

HPLC (Method 10E): R$_t$=4.68 min, >99.0% de (enantiomerically pure isomer 1),

LC-MS (Method 1A): R$_t$=0.91 min; MS (ESIpos): m/z=487 [M+H]$^+$;

$^1$H-NMR (400 MHz, DMSO-d$_6$): δ [ppm]=9.02 (d, 1H), 8.14 (s, 1H), 7.58 (s, 1H), 7.49-7.33 (m, 3H), 6.84 (s, 1H), 6.71 (s, 1H), 5.25 (m$_c$, 1H), 4.91-4.47 (m, 3H), 3.92 (s, 3H), 3.67 (br. s., 1H), 3.07 (br. s., 1H), 1.42 (d, 3H), 0.87-0.29 (m, 4H).

Example 34

7-[(2-{[1-(3-Chlorophenyl)-2-fluoroethyl]amino}-7-methoxy-1,3-benzoxazol-5-yl)carbonyl]-6-methyl-4,7-diazaspiro[2.5]octan-5-one [enantiomerically pure isomer 2]

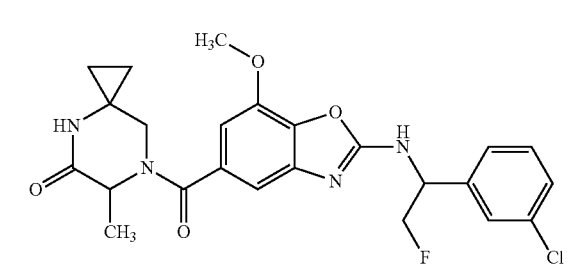 [SMILES: COc1cc(C(=O)N2CC3(CC3)NC(=O)C2C)cc2nc(NC(CF)c3cccc(Cl)c3)oc12]

Diastereomer separation on a chiral phase of 75.0 mg of the compound from Example 32 according to Method 10D gave, after re-purification by preparative RP-HPLC (acetonitrile/water), 15.9 mg of Example 33 (enantiomerically pure isomer 1) and 23.5 mg of Example 34 (enantiomerically pure isomer 2).

HPLC (Method 10E): $R_t$=6.24 min, >99.0% de (enantiomerically pure isomer 2),

LC-MS (Method 1A): $R_t$=0.91 min; MS (ESIpos): m/z=487 [M+H]$^+$;

$^1$H-NMR (400 MHz, DMSO-$d_6$): δ [ppm]=9.01 (d, 1H), 8.15 (s, 1H), 7.59 (s, 1H), 7.50-7.31 (m, 3H), 6.85 (s, 1H), 6.71 (s, 1H), 5.25 ($m_c$, 1H), 4.94-4.48 (m, 3H), 3.92 (s, 3H), 3.10 (br. s., 1H), 1.42 (d, 3H), 0.90-0.27 (m, 4H), one proton obscured.

B) ASSESSMENT OF PHYSIOLOGICAL EFFICACY

The suitability of the compounds according to the invention for treating thromboembolic disorders can be demonstrated in the following assay systems:

a) Test Descriptions (In Vitro)

a.1) Measurement of the Thrombin Inhibition in Buffer

To determine the thrombin inhibition of the substances listed above, a biochemical test system is constructed in which the conversion of a thrombin substrate is used for determining the enzymatic activity of human thrombin. Here, thrombin cleaves aminomethylcoumarin, which is measured fluorescently, from the peptic substrate. The determinations are carried out in microtitre plates.

Substances to be tested are dissolved in various concentrations in dimethyl sulphoxide and incubated for 15 min with human thrombin (0.06 nmol/l dissolved in 50 mmol/l of Tris buffer [C,C,C-tris(hydroxymethyl)aminomethane], 100 mmol/l of sodium chloride, 0.1% BSA [bovine serum albumin], pH 7.4) at 22° C. The substrate (5 µmol/l Boc-Asp(OBzl)-Pro-Arg-AMC from Bachem) is then added. After 30 min of incubation, the sample is excited at a wavelength of 360 nm and the emission is measured at 460 nm. The measured emissions of the test batches with test substance are compared to the control batches without test substance (only dimethyl sulphoxide instead of test substance in dimethyl sulphoxide) and the $IC_{50}$ values are calculated from the concentration/activity relationships. Representative activity data from this test are given in Table 1 below (in some cases as means of individual determinations):

TABLE 1

| Example No. | $IC_{50}$ [nM] | Example No. | $IC_{50}$ [nM] |
|---|---|---|---|
| 1 | 3.20 | 2 | 31.00 |
| 3 | 2.40 | 4 | 1.70 |
| 5 | 1.10 | 6 | 9.70 |
| 7 | 5.30 | 8 | 11.00 |
| 9 | 0.20 | 10 | 130.00 |
| 11 | 0.01 | 12 | 0.10 |
| 13 | 1.20 | 14 | 2.00 |
| 15 | 0.72 | 16 | 0.47 |
| 17 | 0.37 | 18 | 0.30 |
| 19 | 0.98 | 20 | 1.40 |
| 21 | 1.40 | 22 | 1.60 |
| 23 | 1.70 | 24 | 4.40 |
| 25 | 4.30 | 26 | 0.19 |
| 27 | 0.16 | 28 | 2.30 |
| 29 | 1.10 | 30 | 5.30 |
| 31 | 0.54 | 32 | 0.70 |
| 33 | 0.38 | 34 | 20.00 | a.2) Determination of the Selectivity

To demonstrate the selectivity of the substances with respect to thrombin inhibition, the test substances are examined for their inhibition of other human serin proteases, such as factor Xa, factor XIIa, Factor XIa, trypsin and plasmin To determine the enzymatic activity of factor Xa (1.3 nmol/l from Kordia), factor XIIa (10 nmol/l from Kordia), factor XIa (0.4 nmol/l from Kordia), trypsin (83 mU/ml from Sigma) and plasmin (0.1 µg/ml from Kordia), these enzymes are dissolved (50 mmol/l of Tris buffer [C,C,C-tris(hydroxymethyl)aminomethane], 100 mmol/l of sodium chloride, 0.1% BSA [bovine serum albumin], 5 mmol/l of calcium chloride, pH 7.4) and incubated for 15 min with test substance in various concentrations in dimethyl sulphoxide and also with dimethyl sulphoxide without test substance. The enzymatic reaction is then started by addition of the appropriate substrates (5 µmol/l Boc-Ile-Glu-Gly-Arg-AMC from Bachem for FXa, 5 µmol/l H-Pro-Phe-Arg-AMC from Bachem for factor XIIa, 5 µmol/l Boc-Ile-Glu-Gly-Arg-AMC from Bachem for trypsin, 5 µmol/l Boc-Glu(OBzl)-Ala-Arg-AMC from Bachem for factor XIa, 50 µmol/l MeOSuc-Ala-Phe-Lys-AMC from Bachem for plasmin). After an incubation time of 30 min at 22° C., fluorescence is measured (excitation: 360 nm, emission: 460 nm). The measured emissions of the test batches with test substance are compared to the control batches without test substance (only dimethyl sulphoxide instead of test substance in dimethyl sulphoxide), and the $IC_{50}$ values are calculated from the concentration/activity relationships.

a.3) Determination of the Thrombin-Inhibitory Activity of the Potential Inhibitors in Plasma Samples To determine the inhibition of thrombin in plasma samples, plasma prothrombinase is activated by ecarin. Thrombin activity and/or its inhibition by potential inhibitors is/are then measured fluorenscently by addition of a substrate.

The substances to be tested are dissolved in various concentrations in dimethyl sulphoxide and diluted with water. In white 96-well flat-bottomed plates, 20 µl of substance dilution are mixed with 20 µl of ecarin solution (ecarin reagent, from Sigma E-0504, final concentration 20 mU per reaction) in Ca buffer (200 mM Hepes+560 mM sodium chloride+10 mM calcium chloride+0.4% PEG) or with 20 µl of Ca buffer (as unstimulated control). Furthermore, 20 µl of fluorogenic thrombin substrate (from Bachem I-1120, final concentration 50 µmol/l) and 20 µl of citrate plasma (from Octapharma) are added, and the mixture is homogenized well. The plate is measured in a SpectraFluorplus Reader using a 360 nm excitation filter and a 465 nm emission filter every minute over 20 minutes. The $IC_{50}$ value is determined when about 70% of the maximum signal is reached (about 12 min). Representative activity data from this test are given in Table 2 below (in some cases as means of individual determinations):

TABLE 2

| Example No. | $IC_{50}$ [nM] | Example No. | $IC_{50}$ [nM] |
|---|---|---|---|
| 1 | 21.0 | 2 | 31.0 |
| 3 | 11.6 | 4 | 9.8 |
| 5 | 4.8 | 6 | 16.5 |
| 7 | 11.4 | 8 | 25.3 |
| 9 | 14.3 | 10 | 1400 |
| 11 | 5.7 | 12 | 14.7 |
| 13 | 7.8 | 14 | 4.8 |
| 15 | 8.0 | 16 | 5.6 |
| 17 | 13.2 | 18 | 10.9 |

TABLE 2-continued

| Example No. | IC$_{50}$ [nM] | Example No. | IC$_{50}$ [nM] |
|---|---|---|---|
| 19 | 14.1 | 20 | 8.4 |
| 21 | 6.2 | 22 | 3.8 |
| 23 | 4.7 | 24 | 4.5 |
| 25 | 4.7 | 26 | 2 |
| 27 | 4.6 | 28 | 56 |
| 29 | 15 | 30 | 46 |
| 31 | 5 | 32 | 7.3 |
| 33 | 8.4 | 34 | 170 | a.4) Thrombin Generation Assay (Thrombogram)

The effect of the test substances on the thrombogram (thrombin generation assay according to Hemker) is determined in vitro in human plasma (Octaplas® from Octapharma). In the thrombin generation assay according to Hemker, the activity of thrombin in coagulating plasma is determined by measuring the fluorescent cleavage products of the substrate I-1140 (Z-Gly-Gly-Arg-AMC, Bachem). To initiate the coagulation reaction, reagents from Thrombinoscope are used (PPP reagent: 30 pM recombinant tissue factor, 24 µM phospholipids in HEPES). The reaction is carried out in the presence of varying concentrations of test substance or the corresponding solvent. Moreover, a thrombin calibrator from Thrombinoscope is used whose amidolytic activity is required for calculating the thrombin activity in a plasma sample.

The test is carried out according to the specifications of the manufacturer (Thrombinoscope BV): 4 µl of test substance or of the solvent, 76 µl of plasma and 20 µl of PPP reagent or thrombin calibrator are incubated at 37° C. for 5 min. After addition of 20 µl of 2.5 mM thrombin substrate in 20 mM HEPES, 60 mg/ml of BSA, 102 mM of calcium chloride, the thrombin generation is measured every 20 s over a period of 120 min. Measurement is carried out using a fluorometer (Fluoroskan Ascent) from Thermo Electron fitted with a 390/460 NM filter pair and a dispenser. Using the Thrombinoscope software, the thrombogram is calculated and represented graphically. The following parameters are calculated: lag time, time to peak, peak, ETP (endogenous thrombin potential) and start tail.

a.5) Determination of the Anticoagulatory Activity

The anticoagulatory activity of the test substances is determined in vitro in human plasma, rabbit plasma and rat plasma. To this end, blood is drawn off in a mixing ratio of sodium citrate/blood of 1:9 using a 0.11 molar sodium citrate solution as receiver. Immediately after the blood has been drawn off, it is mixed thoroughly and centrifuged at about 4000 g for 15 minutes. The supernatant is pipetted off.

The prothrombin time (PT, synonyms: thromboplastin time, quick test) is determined in the presence of varying concentrations of test substance or the corresponding solvent using a commercial test kit (Neoplastin® from Boehringer Mannheim or Hemoliance® RecombiPlastin from Instrumentation Laboratory). The test compounds are incubated with the plasma at 37° C. for 3 minutes. Coagulation is then started by addition of thromboplastin, and the time when coagulation occurs is determined. The concentration of test substance which effects a doubling of the prothrombin time is determined Representative activity data from this test are given in Table 3 below (in some cases as means of individual determinations):

TABLE 3

| Example No. | IC$_{50}$ [µM] | Example No. | IC$_{50}$ [µM] |
|---|---|---|---|
| 3 | 1.8 | 7 | 1.9 |
| 11 | 1 | 12 | 1.5 |
| 13 | 1.4 | 15 | 1.1 |
| 21 | 1.3 | 25 | 1.1 |
| 27 | 1 | 33 | 0.8 |

The thrombin time (TT) is determined in the presence of varying concentrations of test substance or the corresponding solvent using a commercial test kit (thrombin reagent from Roche). The test compounds are incubated with the plasma at 37° C. for 3 minutes. Coagulation is then started by addition of the thrombin reagent, and the time when coagulation occurs is determined. The concentration of test substance which effects a doubling of the thrombin time is determined The activated partial thromboplastin time (APTT) is determined in the presence of varying concentrations of test substance or the corresponding solvent using a commercial test kit (PTT reagent from Roche). The test compounds are incubated with the plasma and the PTT reagent (cephalin, kaolin) at 37° C. for 3 minutes. Coagulation is then started by addition of 25 mM calcium chloride, and the time when coagulation occurs is determined. The concentration of test substance which effects a doubling of the APTT is determined.

a.6) Thromboelastography (Thromboelastogram)

The thromboelastography is carried out with the aid of the thromboelastograph ROTEM from Pentapharm and its accessories, cup and pin. The measurement is carried out in whole blood drawn off beforehand into sodium citrate monovettes from Sarstedt. The blood in the monovettes is kept in motion using a shaker and preincubated at 37° C. for 30 min A 2-molar stock solution of calcium chloride in water is prepared. This is diluted 1:10 with an aqueous 0.9% sodium chloride solution. For the measurement, 20 µl of this 200 mM calcium chloride solution are initially charged into the cups (final concentration 12.5 mM calcium chloride). 3.2 µl of substance or solvent are added. The measurement is started by addition of 300 µl of whole blood. After the addition, using the tip of the pipette, the mixture is briefly drawn into the pipette and released again without generating air bubbles. The measurement is carried out over a period of 2.5 hours or stopped when fibrinolysis sets in. For evaluation, the following parameters are determined: CT(clotting time/[sec.]), CFT (clotting time/[sec.]), MCF (maximum clot firmness/[mm]) and the alpha angle [°]. The measurement points are determined every 3 seconds and represented graphically, with the y axis for MCF [mm] and the x axis for time [sec.].

a.7) Inhibition of the Coagulation Factor Thrombin Bound to the Thrombus

Blood clots formed either prior to the start of a therapy with anticoagulants, during therapy-free periods or in spite of therapy contain large amounts of coagulation factors which may favour progressive thrombus formation. These coagulation factors are tightly bound to the thrombus and can not be washed out. In certain clinical situations, this may result in a risk for the patient. Using the tests listed below, it is possible to demonstrate, in human thrombi, both thrombin and FXa having biological (procoagulatory) activity.

Thrombi Formed In Vitro

Thrombi are formed in vitro from human plasma and examined for activity of the bound coagulation factors thrombin and FXa. To this end, 300 µl of plasma, 30 µl of lipid vesicles and 30 µl of an aqueous calcium chloride solution are mixed in a 48 MTP plate and incubated for 30 min. This step and the following steps are carried out at 37° C. and with constant agitation (300 rpm). The thrombi formed are transferred to a new 48 MTP plate and twice washed for 10 min in 0.9% sodium chloride solution, the thrombus being dabbed on filter paper between the washing steps. The thrombus is transferred into buffer B (Owren's Veronal buffer, 1% BSA) and incubated for 15 min, dabbed on filter paper and incubated for 30 min in test substance in various concentrations in buffer B. The clots are then washed twice as described above. The thrombi are dabbed and transferred into buffer D: (240 µl Owren's Veronal buffer, 1% BSA and 15.6 mM calcium chloride) and incubated with or without 0.6 µM prothrombin for 45 min. The reaction is stopped with 75 µl of 1% EDTA solution. Thrombin activity is measured separately in the thrombus in buffer A (7.5 mM $Na_2EDTA \times 2H_2O$, 175 mM sodium chloride, 1% BSA, pH 8.4) or in the supernatant from the last step. To this end, the thrombin substrate used in a.1) is employed in a final concentration of 50 µM, and the resulting fluorescence is measured in a fluorescence plate reader (360/465 nm).

a.8) Effect of the Thrombin Inhibitors on Thrombolysis in Platelet-Poor Plasma

The effect of the test substances on in vitro thrombolysis in platelet-poor plasma is tested in the presence of tissue plasminogen activator (tPA). To this end, with monitoring by turbidity measurement (UV absorption at 405 nm), initially a clot is formed in a microtitre plate in human plasma with addition of tissue factor, and the dissolution of the clot is adjusted to a certain time window by simultaneous addition of tissue plasminogen activator (tPA). Simultaneous addition of different amounts of the test substance may result in a shortening of the thrombolysis time (the time it takes from maximum turbidity to getting back to the baseline).

In a 384-well microtitre plate, 0.7 µl of an ethanol/water mixture (1:1) comprising various concentrations of the test substances, 1.7 µl of a solution of human thrombomodulin (final concentration 10 nM) and 1.7 µl of a solution of human tissue plasminogen activator (Actilyse®, final concentration 3 nM) are added to 63 µl of human plasma (German Red Cross, corresponds to 90% plasma in the test). Coagulation is initiated by addition of 3.5 µl of a tissue factor-containing solution (Recombiplastin 2G in a 1:100 dilution in 0.2 M calcium chloride solution) at 37° C. Measurement of turbidity (UV absorptions measurement at 405 nm) at one minute intervals is then started immediately. The thrombolysis time is calculated as the time it takes from maximum absorption to getting back to the baseline.

b) Determination of Antithrombotic Activity (In Vivo)

b.1) Arteriovenous Shunt and Haemorrhage Model (Combi-Model Rat)

Fasting male rats (strain: HSD CPB:WU) having a weight of 300-350 g are anaesthetized using Inactin (150-180 mg/kg). Thrombus formation is initiated in an arteriovenous shunt in accordance with the method described by Christopher N. Berry et al., Br. J. Pharmacol. (1994), 113, 1209 1214. To this end, the left jugular vein and the right carotid artery are exposed. The two vessels are connected by an extracorporeal shunt using a polyethylene tube (PE 60) having a length of 10 cm. In the middle, this polyethylene tube is attached to a further polyethylene tube (PE 160) having a length of 3 cm which contains a roughened nylon thread arranged to form a loop, to form a thrombogenic surface. The extracorporeal circulation is maintained for 15 minutes. The shunt is then removed and the nylon thread with the thrombus is weighed immediately. The weight of the nylon thread on its own is determined before the experiment is started.

To determine the bleeding time, immediately after opening of the shunt circulation, the tip of the tail of the rats is docked by 3 mm using a razor blade. The tail is then placed into physiological saline kept at a temperature of 37° C., and the bleeding from the cut is observed over a period of 15 minutes. What is determined is the time until bleeding ceases for at least 30 seconds (initial bleeding time), total bleeding time over a period of 15 minutes (cumulative bleeding time) and the quantitative blood loss via photometric determination of the collected haemoglobin.

Before the extracorporeal circulation is set up and the tip of the tail is docked, the test substances are administered to the animals while awake either intravenously via the contralateral jugular vein as a single bole or as a bole with subsequent continuous infusion or orally using a pharyngeal tube.

b.2) Iron(II) Chloride Damage and Bleeding Model (Combi Model II, Rat)

Male rats (strain: HsdRCCHan:Wist) having a weight of 300 g-325 g are anaesthetized intraperitoneally with Inactin (180 mg/kg). Thrombus formation is triggered using iron(II) chloride in the carotid artery. To this end, the right carotid artery is exposed. A flow probe head is then attached, and the blood flow is recorded for 10 minutes. Artery and surroundings are then drained. Parafilm (10×8 mm) and filter paper (10×6 mm folded) are placed under the carotid artery and wetted with 20 µl iron(II) chloride solution (iron(II) chloride tetrahydrate reagent plus 99%, Sigma, 5% solution in water is prepared). A small piece of filter paper is placed on top of the carotid artery and also wetted with iron(II) chloride solution. The carotid artery prepared in this manner is covered with a moist swab and left for 5 minutes. Parafilm and filter paper are then removed and the artery is rinsed with physiological sodium chloride solution. The flow probe head is reattached and the blood flow is recorded for 30 minutes. The measurement is then stopped and the exposed section of the carotid artery is pinched off with tissue clamps and excised. The thrombus located in the vessel is removed from the vessel with the aid of a pair of tweezers and weighed immediately.

To determine the bleeding time, after injury and re-attachment of the flow probe head the tip of the tail of the rat is docked by 3 mm using a razor blade. The tail is then placed into water kept at a temperature of 37° C., and the bleeding from the cut is observed over a period of 15 minutes. What is determined is the time until bleeding ceases for at least 30 seconds (initial bleeding time), total bleeding time over a period of 15 minutes (cumulative bleeding time) and the quantitative blood loss via photometric determination of the collected haemoglobin.

The test substances are administered either intravenously via the jugular vein as single bole directly before the start of the experiment or as a bole (prior to the start) with subsequent continuous infusion.

b.3) Rabbit Venous Reperfusion and Bleeding Model (Combi Model Rabbit)

Male New Zealand rabbits having a weight of 2.8-3.4 kg are anaesthetized using an intramuscular ketamine/Rompun bole injection. The animal is then shaved at the places needed for the surgery. A continuous infusion of anaesthetic (ketamine/Rompun) is administered via the left auricular vein using an indwelling catheter. Left and right femoral vein and right femoral artery are catheterized with a polyethylene tube (PESO). The jugular vein is then carefully exposed such that the vessel is stressed and damaged as little as possible and no more fat is present at the vessel. Using a suitable apparatus for measuring flow (Powerlab, Transonic TS420 incl. flow probe head), the flow in the jugular vein is recorded (Lab Chart Software). Prior to the start of the experiment, twice 1.4 ml of citrated blood are removed from the rabbit via the femoral artery, and the basal bleeding time at the rim of the ear is determined. Once there has been a constant flow from the jugular vein for 10 min (complete regeneration of the vessel after preparation), a 2 cm section of the vein is pinched off using small vessel clamps. In a Petri dish, the citrated blood removed earlier (300 µl) is mixed with calcium chloride (0.25 M, 90 µl) and thrombin (25 U/ml, 60 µl). 180 µl of the blood/calcium chloride/thrombin mixture are quickly drawn into a 1 ml syringe and, via a 27G cannula, injected into the pinched-off segment of the vessel. The injection site is pinched off with a pair of tweezers for one minute so that no blood can escape. Two minutes after injection of the thrombus, the test substance is administered as bole and infusion via the left femoral vein catheter. 14 minutes after the thrombus injection, tissue plasminogen activator is administered as bole and infusion (Actilyse®, 20 µg/kg bole & 150 µg/kg/h infusion) at the right femoral vein. 15 minutes after thrombus injection, the stasis is opened and the flow probe head is attached. Blood flow in the vessel is recorded for 120 minutes, and the vessel is kept moist with warm 0.9% aqueous sodium chloride solution during this time. After 105 minutes of reperfusion, the ear bleeding time is determined again. At the end of the experiment, after 120 minutes of reperfusion, 1.4 ml of citrated blood are removed, the animal is sacrificed painlessly by a bole injection of 1.5 ml of T61 and the weight of the thrombus in the jugular vein is determined. The blood removed before and after the experiment is used to obtain plasma and to determine the ex vivo coagulation time.

The area under the blood flow/time curve (AUC) is calculated and correlated to the maximum achievable area, which is calculated from the blood flow before the experiment and the time (120 min). The area obtainable with tissue plasminogen activator alone is subtracted from the area achieved using the respective substance or dosage. The resulting area is a measure of the improvement of reperfusion by the test substance (Table 4).

TABLE 4

Synergistic antithrombotic action of
the combination of Example 15 with rivaroxaban
Increase in reperfusion (blood flow/time
area) after treatment with

| compound from Example 15 [bole 0.33 mg/kg; continuous infusion 0.43 mg/kg/h] | rivaroxaban [bole 0.08 mg/kg; continuous infusion 0.09 mg/kg/h] | combination of the compound from Example 15 [bole 0.33 mg/kg; continuous infusion 0.43 mg/kg/h] with rivaroxaban [bole 0.08 mg/kg; continuous infusion 0.09 mg/kg/h] |
|---|---|---|
| 12.2% insignificant effect ($p > 0.05$) | 13.0% insignificant effect ($p > 0.05$) | 49.5% significant effect ($p < 0.05$) | c) Determination of Pharmacokinetics c.1) Pharmacokinetics Following Intravenous Administration of the Test Substance Male Wistar rats are anaesthetized, and a catheter is placed in the jugular vein. The next day, a defined dose of the test substance is administered as a solution by injection into the tail vein. Blood samples are collected via the catheter over a period of 7 hours (9 points in time).

A defined dose of the test substance is administered to female Beagles as a solution via the cephalic vein as a 15 min infusion. Blood samples are collected via a catheter over a period of 7 hours (12 points in time).

The blood is centrifuged in heparin tubes. To precipitate the protein, acetonitrile is added and the plasma sample is centrifuged. The test substance is quantified in the supernatant by LC/MS-MS. The test substance plasma concentrations determined are used to calculate of pharmacokinetic parameters such as AUC (area under the plasma concentration/time curve), $V_{ss}$ (distribution volume), $C_{max}$ (highest concentration the test substance in the plasma after administration), $t_{1/2}$ (half-life) and CL (total clearance of the test substance from the plasma). To calculate the blood clearance, the blood/plasma distribution is determined by incubating the test substance in blood. After removal of the plasma by centrifugation, the concentration of the test substance in the plasma is determined by LC/MS-MS.

c.2) Pharmacokinetics Following Oral Administration of the Test Substance

Male Wistar rats are anaesthetized, and a catheter is placed in the jugular vein. The next day, a defined dose of the test substance is administered orally. Blood samples are collected via the catheter over a period of 24 hours (9 points in time).

A defined dose of the test substance is administered orally to female Beagles. Blood samples are collected via a catheter in the cephalic vein over a period of 24 hours (9 points in time).

The blood is centrifuged in heparin tubes. To precipitate the protein, acetonitrile is added and the plasma sample is centrifuged. The test substance is quantified in the supernatant by LC/MS-MS. The test substance plasma concentrations determined are used to calculate pharmacokinetic parameters such as AUC (area under the plasma concentration/time curve), $C_{max}$ (highest concentration of the test substance in the plasma after administration), $t_{1/2}$ (half-life) and F (bioavailability).

c.3) Caco-2 Permeability Assay

The in vitro permeability of the test substance through a Caco-2 cell monolayer is determined using an established in vitro system for predicting the permeability through the gastrointestinal tract [1]. CaCo-2 cells (ACC No. 169, DSMZ, Deutsche Sammlung von Mikroorganismen and Zellkulturen, Brunswick, Germany) are sown in 24-well plates and cultivated for 14 to 16 days. The test substance is dissolved in DMSO and diluted to a concentration of 2 µM in transport buffer (HBSS, Hanks Buffered Salt Solution, Gibco/Invitrogen, supplemented with glucose (final concentration 19.9 mM) and HEPES (final concentration 9.8 mM)). To determine the permeability from apical to basolateral ($P_{app}$ A-B), the test substance is added on the apical side and transport buffer is added at the basolateral side of the cell monolayer. To determine the permeability from basolateral to apical ($P_{app}$ B-A), the test substance is added on the basolateral side and transport buffer is added at the apical side of the cell monolayer. At the start of the experiment, samples are taken from the donor compartment to determine the mass balance. After an incubation time of 2 hours at 37° C., samples were taken from the two compartments. The samples were quantified by LC-MS/MS, and the permeability coefficients were calculated. For each cell monolayer, the permeability of Lucifer Yellow was determined to ensure cell layer integrity. In each test run, the permeability of atenolol (marker for low permeability) and sulfasalazine (marker for active excretion) is also determined to check the quality of the cells.

Literature: Artursson, P. and Karlsson, J. (1991). Correlation between oral drug absorption in humans and apparent drug permeability coefficients in human intestinal epithelial (Caco-2) cells. Biochem. Biophys. 175 (3), 880-885.

c.4) In Vitro Clearance Determinations with Hepatocytes

Incubations with fresh primary hepatocytes are carried out at 37° C. in a total volume of 1.5 ml with a modified Janus® robot (Perkin Elmer) while shaking. The incubations typically contain 1 million living liver cells/ml, ~1 µM substrate and 0.05 M potassium phosphate buffer (pH=7.4). The final ACN concentration in the incubation is ≤1%.

Aliquots of 125 µl are withdrawn from the incubations after 2, 10, 20, 30, 50, 70 and 90 mM and transferred into 96-well filter plates (0.45 µm low-binding hydrophilic PTFE; Millipore: MultiScreen Solvinert). Each of these contain 250 µl of ACN to stop the reaction. After the centrifugation, the filtrates are analysed by MS/MS (typically API 3000).

The in vitro clearances are calculated from the half-lives of the substance degradation, using the following equations:

$CL'_{inrinsic}[ml/(min \cdot kg)]=(0.693/in\ vitro\ t\frac{1}{2}[min]) \cdot$
(liver weight[g liver/kg body weight])·(cell number[$1.1 \cdot 10^{\wedge}8$]/liver weight[g])/(cell number [$1 \cdot 10^{\wedge}6$]/incubation volume[ml])

$CL_{blood}$ is calculated without taking into account the free fraction ("nonrestricted well stirred model") by the following equation:

$CL_{blood}$ well-stirred[$1/(h \cdot kg)$]=$(Q_H[1/(h \cdot kg)] \cdot CL'_{intrinsic}[1/(h \cdot kg)])/(Q_H[1/(h \cdot kg)]+ CL'_{intrinsic}[1/(h \cdot kg)])$ The species-specific extrapolation factors used for the calculation are summarized in Table 5 below:

TABLE 5

| | male/female | | | | | |
|---|---|---|---|---|---|---|
| | Mouse m | Mouse f | Rat m/f | Dog m/f | Cyno f | Man m/f |
| Cell number/g Liver [millions of cells] | 110 | 110 | 110 | 110 | 110 | 110 |
| Liver [g]/kg Body Weight | 50 | 43 | 32 | 39 | 30 | 21 |
| Liver Blood Flow [l/(h · kg)] | 5.4 | 5.4 | 4.2 | 2.1 | 2.5 | 1.3 |

$F_{max}$ values which state the maximum possible bioavailability—based on the hepatic extraction—are calculated as follows:

$F_{max}$ well-stirred[%]=$(1-(CL_{blood}$ well-stirred[$1/(h \cdot kg)$]$/Q_H[1/(h \cdot kg)])) \cdot 100$ c.5) CYP Inhibition Test Inhibitory properties of an active compound on the cytochromes P450 (CYP) of the human body may entail extensive clinical effects (drug interactions) because most prescribed medicaments are degraded (metabolized) by these enzymes. Involved in this in particular are the CYP isoenzymes of the 1A and 2C families, CYP2D6 and, with a proportion of almost 50%, CYP3A4. In order to preclude or minimize these possible drug interactions (Drug-Drug Interactions, DDI), the ability of substances to be able to inhibit CYP1A2, CYP2C8, CYP2C9, CYP2D6 and CYP3A4 in humans is investigated using human liver microsomes (pool from various individuals). This takes place by measuring CYP isoform-specific metabolites formed from standard substrates such as, for example, phenacetin, amodiaquin, diclofenac, dextromethorphan, midazolam and testosterone. The inhibitory effects are investigated at six different concentrations of the test compounds (1.5, 3.1, 6.3, 12.5, 25 and 50 µM as maximum concentration or 0.6, 1.3, 2.5, 5, 10 and 20 µM as maximum concentration), compared with the extent of the CYP isoform-specific metabolite formation of the standard substrates in the absence of the test compounds, and the corresponding IC50 values are calculated. CYP isoform-specific standard inhibitors such as, for example, furafylline, montelukast, sulfaphenazole, fluoxetine and ketoconazole serve as control of the results obtained. In order to obtain indications of the possible mechanism-based inhibitors (MBI) on CYP3A4, the human liver microsomes are incubated in the presence of the inhibitor to be investigated for 30 minutes before the addition of midazolam or testosterone as standard substrates of CYP3A4. A reduction in the IC50 obtained by comparison with the mixture without preincubation serves as an indicator of a mechanism-based inhibition. Mibefradil serves as positive control.

Procedure:

The incubations of the standard substrates with human liver microsomes (14-100 µg/ml) in the presence of the test compound (as potential inhibitor) are carried out at 37° C. in 96-well plates on a workstation (Tecan, Genesis; Hamilton, MICROLAB STARLET). The incubation times are 10-15 minutes. The test compounds are preferably dissolved in acetonitrile (1.0, 2.0 or 2.5, 5.0 mM stock solution). The 96-well plates are prepared by sequential addition of a stock solution of NADP+, EDTA, glucose 6-phosphate and glucose 6-phosphate dehydrogenase in phosphate buffer (pH 7.4), the test compound and a solution of standard substrate and human liver microsomes in phosphate buffer (pH 7.4). The total volume is 200 µl. Also located on the 96-well plate are the corresponding control incubations with and without standard inhibitor. After the respective incubation time, the incubations are stopped by addition of 100 µl of acetonitrile comprising a suitable internal standard. Precipitated proteins are removed by centrifugation (3000 rpm, 10 minutes, 10° C.). The resulting supernatants of the respective plates are combined on a plate and analyzed by LC-MS/MS. From the measurement data obtained, the $IC_{50}$ values are generated and used to assess the inhibitory potential of the test compound.

c.6) Cellular In Vitro Test for Determining the Induction of Drug-Degrading Cytochromal Enzymes (CYPs) in Primary Human Hepatocytes Enzyme induction is an unwanted property of a drug which puts broad and safe use of the active compound into question. A consequence of enzyme induction is an accelerated degradation (metabolization) of drugs in the liver. Combined intake of an enzyme inducer and other medicaments such as, for example, immunosuppressives, coagulants or else contraceptives may lead to complete ineffectiveness of the drugs.

The object of the investigation is to provide substances which do not have this unwanted drug interaction. Enzyme inductors are identified with the aid of primary human hepatocytes in long-term culture. To cultivate the cells, hepatocytes are plated on a collagen I layer (density 100000 cells/cm$^2$), and the grown-on cells are then covered with a second collagen layer (sandwich method). (Kern A, Bader A, Pichlmayr R, and Sewing K F, Biochem Pharmacol., 54, 761-772 (1997). To obtain the effect of the test substances on the regulation of the liver enzymes, the hepatocytes are incubated with the active compounds for several days in long-term culture.

Assay Procedure:

After a two-day regeneration phase, the cells are treated in Williams Medium E, 10% FCS, prednisolone, insulin, glucagon and L-glutamine, penicillin and streptomycin with the test substances. To this end, stock solutions of the active compounds having a concentration of 1 mg/ml in acetonitrile or methanol are prepared and, in 8 dilution steps (1:3) in cell culture medium, pipetted to the cell cultures, which are then incubated in a cell incubator (96% atmospheric humidity, 5% v/v carbon dioxide, 37° C.) for about 5 days. The cell culture medium is changed daily. After this incubation time, the cell cultures are incubated with cytochrome P450(CYP)-specific substrates to determine the activity of the liver enzymes CYP1A2, CYP3A4, CYP2B6 and CYP2C19. The samples thus stopped are either analysed directly or stored at −20° C. until analysis.

To this end, the media of the cell cultures are chromatographed using suitable C18-reversed-phase columns and variable mixtures of acetonitrile and 10 mM ammonium formate (HPLC-MS/MS).

The mass spectrometric data serve to quantify the substrate turnover and, derived therefrom, to calculate the liver enzyme activities. Active compounds having unfavourable properties with respect to liver enzyme regulation are not persued any further.

d) Purification, Crystallization and Single Crystal Structure Determination of Human α-Thrombin (=FIIa) in a Complex with Example 15 d.1) Crystallization of Human α-Thrombin

The protein α-thrombin was purchased from Haemochrom (Uniprot P00734, amino acids 328 to 622). A vial with 5000 U (~1.7 mg) of the proteins is adjusted to a concentration of about 10 mg/ml using a 20 mM phosphate buffer of pH 7.5, 350 mM sodium chloride crystallization buffer and 2 mM benzamidine. The concentration of the α-thrombin is checked using a NanoDrop® ND-1000 spectrophotometer. A hirudin fragment (purchased from Bachem) is added to the α-thrombin solution in a molar ratio of 1:4. The mixture is incubated at 4° C. for at least 2 hours. Measurable single crystals can be obtained at 10° C. using the hanging-drop method. To this end, identical volumes of the protein solution and the reservoir solution (0.02 M phosphate buffer of pH 7.5, 27% PEG 8000, 100 mM sodium chloride solution) are combined using a pipette, and α-thrombin seed crystals are added. In most cases, α-thrombin crystals are formed overnight.

d.2) Complex Formation of Human α-Thrombin with Example 15 in the Crystal

A 50 mM DMSO solution of Example 15 was diluted with reservoir buffer to a final concentration of 5 mM. α-Thrombin crystals were transferred into 2 μl of this solution and left in this solution overnight (=soaking).

d.3) Data Collection and Processing

The soaked crystal was placed very briefly into a solution with 0.02 M phosphate buffer at pH 7.5, 27% PEG 8000, 100 mM sodium chloride solution and 15% glycerol and then shock-frozen in liquid nitrogen. The crystal was measured on a Bruker Proteum System at 100K and a wavelength of 1.5418 Å. A CCD counter was used for detection. The data were integrated using the SAINT program and scaled using the SADABS program (both part of the Bruker Proterum program package). The crystal scattered up to a resolution of 1.6 Å and crystallized in the monocline space group C2 with cell edges a=69.166 Å, b=70.343 Å and c=71.372 Å with a molecule in the asymetric unit.

d.4) Structure Determination and Refinement

The structure of α-thrombin was resolved using the molecular replacement method with a further internal structure as search model and the PHASER program (CCP4 program package). Example 15 was generated as 3D model with the aid of the Discovery Studio program, and a parameter file was generated using the PRODRG program. Example 15 was placed manually into the electron density and minimized in the electron density in the COOT program. Further refinement was carried out iteratively using the REFMAC5.5 and COOT programs (both CCP4 program package) to give a final R1 value of 20.52% and an Rfree value of 24.73%. Data and refinement statistics are summarized in Table 6.

TABLE 6

Data collection and refinement statistics for human α-thrombin in a complex with Example 15.

| | |
|---|---|
| Wavelength | 1.5418 Å |
| Resolution (outermost shell) | 71.27-1.59 (1.69-1.59) Å |
| Reflexes (observed/averaged) | 130734/40347 |
| Completeness$^a$ | 89.2% (90.2%) |
| I/s$^a$ | 12.95 (2.85) |
| R$_{merge}$$^{a,b}$ | 0.064 (0.27) |
| Space group | C2 |
| Cell parameters | |
| a | 69.166 Å |
| b | 70.343 Å |
| c | 71.372 Å |
| b | 100.28° |
| R$_{cryst}$$^c$ | 0.2052 |
| R$_{free}$$^d$ | 0.2473 |
| Wilson temperature factor | 14.3 Å$^2$ |
| RMSD binding lengths $^e$ | 0.023 Å |
| RMSD binding angle | 2.212° |

$^a$The values in parentheses are for the outermost resolution shell
$^b$R$_{merge}$ = Σhkl |I$_{hkl}$ − (I$_{hkl}$)|/Σhkl (I$_{hkl}$); I$_{hkl}$ is the intensity of the reflex hkl and (I$_{hkl}$) is the mean of intensities measured multiple times
$^c$R$_{cryst}$ = Σ |F$_{obs}$ − F$_{calc}$|/Σ F$_{obs}$; F$_{obs}$ and F$_{calc}$ are the observed and ideal calculated structural factors
$^d$5% test set
$^e$ RMSD, root mean square deviation from the parameter set of the binding geometry d.5) Determination of the Absolute Structure of Example 15 in Human α-Thrombin The complex of α-thrombin with Example 15 crystallizes with a molecule in the asymmetric unit. The stereochemistry of Example 15 is determined unambiguously by knowledge of the stereochemistry of the protein α-thrombin. In Example 15, all stereocentres (C13, C28 and C31) unambiguously have the S configuration.

Structure of Example 15

(2-{[(1S)-1-(3-chlorophenyl)-2-fluoroethyl]amino}-7-methoxy-1,3-benzoxazol-5-yl][(2S,5S)-5-(2-hydroxyethyl)-2-methylmorpholin-4-yl]methanone of the formula below

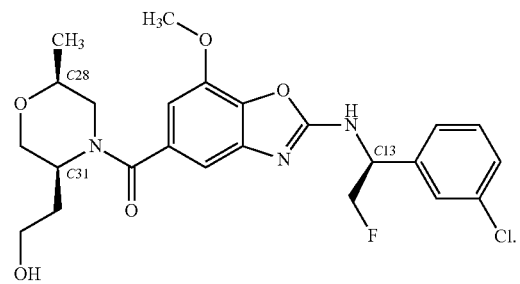 [SMILES: COc1cc(C(=O)N2C[C@H](C)OC[C@@H]2CCO)cc2nc(N[C@H](CF)c3cccc(Cl)c3)oc12]

C) WORKING EXAMPLES OF PHARMACEUTICAL COMPOSITIONS

The substances according to the invention can be converted to pharmaceutical preparations as follows:

Tablet:

Composition:

100 mg of the compound of Example 1, 50 mg of lactose (monohydrate), 50 mg of maize starch, 10 mg of polyvinylpyrrolidone (PVP 25) (from BASF, Germany) and 2 mg of magnesium stearate.

Tablet weight 212 mg, diameter 8 mm, radius of curvature 12 mm

Production:

The mixture of the compound of Example 1, lactose and starch is granulated with a 5% strength solution (m/m) of the PVP in water. After drying, the granules are mixed with the magnesium stearate for 5 min. This mixture is pressed with a conventional tableting press (for tablet dimensions see above).

Oral Suspension:

Composition:

1000 mg of the compound of Example 1, 1000 mg of ethanol (96%), 400 mg of Rhodigel (xanthan gum) (from FMC, USA) and 99 g of water.

A single dose of 100 mg of the compound according to the invention corresponds to 10 ml of oral suspension.

Production:

The Rhodigel is suspended in ethanol, and the compound of Example 1 is added to the suspension. The water is added while stirring. The mixture is stirred for about 6 h until swelling of the Rhodigel is complete.

Intravenously Administrable Solution:

Composition:

1 mg of the compound of Example 1, 15 g of polyethylene glycol 400 and 250 g of water for injection purposes.

Production:

The compound of Example 1 is dissolved together with polyethylene glycol 400 by stirring in the water. The solution is sterilized by filtration (pore diameter 0.22 μm) and dispensed under aseptic conditions into heat-sterilized infusion bottles. The latter are closed with infusion stoppers and crimped caps.

The invention claimed is:

1. A compound of the formula

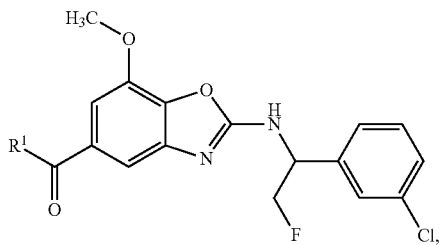

(I)

in which
$R^1$ represents a group of the formula

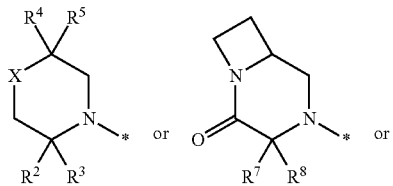

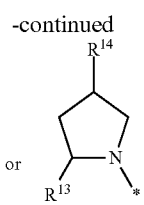

where * is the point of attachment to the carbonyl group,

X represents an oxygen atom, a sulphur atom or CH—$R^6$, where
   $R^6$ represents hydroxyl,
$R^2$ represents hydrogen, $C_1$-$C_6$-alkyl, $C_3$-$C_6$-cycloalkyl or phenyl,
   where alkyl and cycloalkyl may be substituted by a substituent selected from the group consisting of hydroxy, methoxy, cyano, hydroxycarbonyl, aminocarbonyl, methylsulphonyl, difluoromethoxy and trifluoromethoxy,
   or
   where alkyl and cycloalkyl may be substituted by 1 to 3 fluorine substituents,
$R^3$ represents hydrogen or $C_1$-$C_4$-alkyl,
or
$R^2$ and $R^3$ together with the carbon atom to which they are attached form a cyclopropyl ring, cyclobutyl ring or cyclopentyl ring,
   where the cyclobutyl ring and the cyclopentyl ring may be substituted by a
   hydroxyl substituent,
$R^4$ represents hydrogen or $C_1$-$C_6$-alkyl,
   where alkyl may be substituted by a hydroxyl substituent,
$R^5$ represents $C_1$-$C_4$-alkyl,
or
$R^4$ and $R^5$ together with the carbon atom to which they are attached form a cyclopropyl ring, cyclobutyl ring or cyclopentyl ring,
   where the cyclobutyl ring and the cyclopentyl ring may be substituted by a
   hydroxyl substituent,
$R^7$ represents hydrogen or $C_1$-$C_6$-alkyl,
   where alkyl may be substituted by a hydroxyl or cyano substituent, or
   where alkyl may be substituted by 1 to 3 fluorine substituents,
$R^8$ represents hydrogen,
$R^9$ represents hydrogen or $C_1$-$C_6$-alkyl,
   where alkyl may be substituted by a hydroxyl or cyano substituent,
   or
   where alkyl may be substituted by 1 to 3 fluorine substituents,
$R^{10}$ represents hydrogen,
$R^{11}$ represents $C_1$-$C_4$-alkyl,
   where alkyl may be substituted by a hydroxyl substituent,
$R^{12}$ represents hydrogen or $C_1$-$C_4$-alkyl,
or
$R^{11}$ and $R^{12}$ together with the carbon atom to which they are attached form a cyclopropyl ring, cyclobutyl ring or cyclopentyl ring,
   where the cyclobutyl ring and the cyclopentyl ring may be substituted by a hydroxyl substituent,
$R^{13}$ represents hydroxymethyl or hydroxyethyl,
$R^{14}$ represents methoxy or ethoxy,
or one of the salts thereof, solvates thereof or solvates of the salts thereof.

2. The compound of claim 1, characterized in that R¹ represents a group of the formula

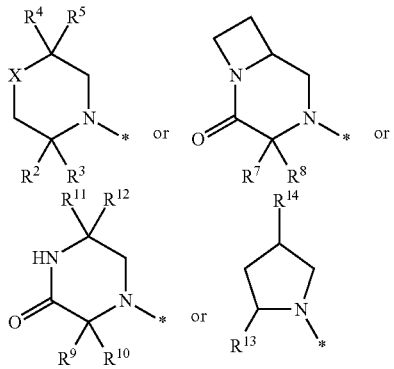

where * is the point of attachment to the carbonyl group,
X represents an oxygen atom or CH—R⁶,
where
R⁶ represents hydroxyl,
R² represents hydrogen, $C_1$-$C_4$-alkyl or $C_3$-$C_6$-cycloalkyl,
where alkyl may be substituted by a hydroxyl or hydroxycarbonyl substituent,
and
where cycloalkyl may be substituted by a hydroxyl substituent,
R³ represents hydrogen or $C_1$-$C_4$-alkyl,
or
R² and R³ together with the carbon atom to which they are attached form a cyclobutyl ring,
where the cyclobutyl ring may be substituted by a hydroxyl substituent,
R⁴ represents hydrogen or $C_1$-$C_4$-alkyl,
where alkyl may be substituted by a hydroxyl substituent,
R⁵ represents $C_1$-$C_4$-alkyl,
R⁷ represents hydrogen or $C_1$-$C_4$-alkyl,
R⁸ represents hydrogen,
R⁹ represents hydrogen or $C_1$-$C_4$-alkyl,
where alkyl may be substituted by a hydroxyl substituent,
R¹⁰ represents hydrogen,
R¹¹ and R¹² together with the carbon atom to which they are attached form a cyclobutyl ring,
R¹³ represents hydroxymethyl or hydroxyethyl,
R¹⁴ represents methoxy or ethoxy,
or one of the salts thereof, solvates thereof or solvates of the salts thereof.

3. The compound of claim 1, characterized in that R¹ represents a group of the formula

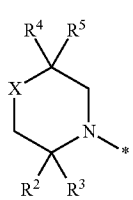

where * is the point of attachment to the carbonyl group,
X represents an oxygen atom,
R² represents methyl, ethyl or cyclobutyl, where methyl and ethyl are substituted by a hydroxyl substituent,
and
where cyclobutyl is substituted by a hydroxyl substituent,
R³ represents hydrogen,
R⁴ represents hydrogen or methyl,
and
R⁵ represents methyl,
or
R² represents methyl,
R³ represents hydrogen or methyl,
R⁴ represents methyl, ethyl or propyl,
where methyl, ethyl and propyl are substituted by a hydroxyl substituent,
and
R⁵ represents methyl,
or
R² and R³ together with the carbon atom to which they are attached form a cyclobutyl ring,
where the cyclobutyl ring is substituted by a hydroxyl substituent,
R⁴ represents hydrogen or methyl,
and
R⁵ represents methyl,
or one of the salts thereof, solvates thereof or solvates of the salts thereof.

4. The compound of claim 1, characterized in that R¹ represents a group of the formula

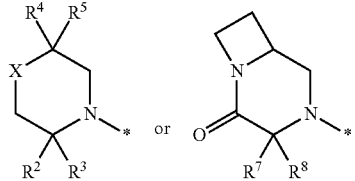

where * is the point of attachment to the carbonyl group,
X represents an oxygen atom,
R² represents methyl or ethyl,
where methyl and ethyl are substituted by a hydroxyl substituent,
R³ represents hydrogen,
or
R² and R³ together with the carbon atom to which they are attached form a cyclobutyl ring,
where the cyclobutyl ring is substituted by a hydroxyl substituent,
R⁴ represents hydrogen or methyl,
R⁵ represents methyl,
R⁷ represents hydrogen or methyl,
R⁸ represents hydrogen,
or one of the salts thereof, solvates thereof or solvates of the salts thereof.

5. The compound of claim 1, characterized in that R¹ represents a group of the formula

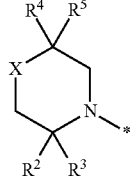

where * is the point of attachment to the carbonyl group,
X represents an oxygen atom,
$R^2$ represents methyl or ethyl,
where methyl and ethyl are substituted by a hydroxyl substituent,
$R^3$ represents hydrogen,
or
$R^2$ and $R^3$ together with the carbon atom to which they are attached form a cyclobutyl ring,
where the cyclobutyl ring is substituted by a hydroxyl substituent,
$R^4$ represents hydrogen or methyl,
$R^5$ represents methyl,
or one of the salts thereof, solvates thereof or solvates of the salts thereof.

6. (2-{[(1S)-1-(3-Chlorophenyl)-2-fluoroethyl]amino}-7-methoxy-1,3-benzoxazol-5-yl)[(2S,5S)-5-(2-hydroxyethyl)-2-methylmorpholin-4-yl]methanone according to claim 1 of the formula below

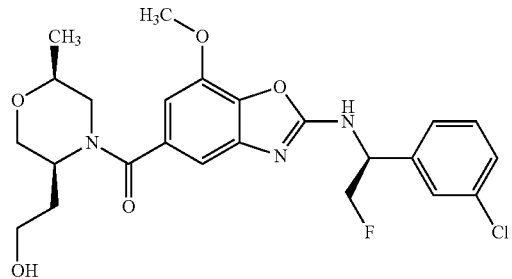 [SMILES: COc1cc(C(=O)N2C[C@H](C)OC[C@@H]2CCO)cc2nc(N[C@H](CF)c3cccc(Cl)c3)oc12]

or one of the salts thereof, solvates thereof or solvates of the salts thereof.

7. (2-{[(1S)-1-(3-Chlorophenyl)-2-fluoroethyl]amino}-7-methoxy-1,3-benzoxazol-5-yl)[(2S,5S)-5-(2-hydroxyethyl)-2-methylmorpholin-4-yl]methanone according to claim 1 of the formula below

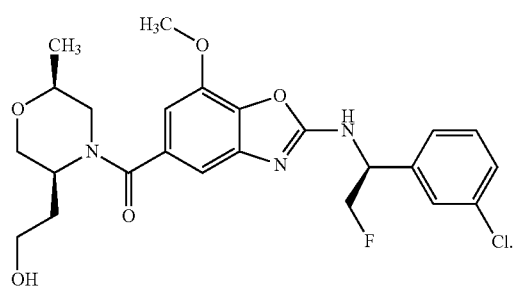 [SMILES: COc1cc(C(=O)N2C[C@H](C)OC[C@@H]2CCO)cc2nc(N[C@H](CF)c3cccc(Cl)c3)oc12]

8. A method of making a compound of the formula (I) or one of the salts thereof, solvates thereof or solvates of the salts thereof according to claim 1, characterized in that a compound of the formula

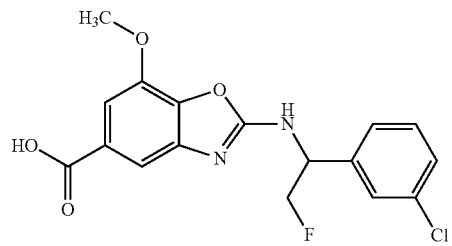

(II)

is reacted with a compound of the formula $$R^1-H \quad (III)$$

in which
$R^1$ has the meaning given in claim 1
with dehydrating agents.

9. A method for the treatment and/or prophylaxis of cardiovascular diseases comprising administering an effective amount of the compound of claim 1.

10. A method of making a medicament for the treatment and/or prophylaxis of diseases comprising combining the compound of claim 1 with an inert, nontoxic, pharmaceutically suitable excipient.

11. A method of making a medicament for the treatment and/or prophylaxis of thromboembolic disorders comprising combining the compound of claim 1 with an inert, nontoxic, pharmaceutically suitable excipient.

12. A medicament for the treatment and/or prophylaxis of acute coronary syndrome (ACS), venous thromboembolisms, venous thromboses, pulmonary embolisms, stroke and/or thrombosis prophylaxis in the context of surgical interventions comprising the compound of claim 1 in combination with an inert, nontoxic, pharmaceutically suitable excipient.

13. A medicament comprising the compound of claim 1, in combination with an inert, nontoxic, pharmaceutically suitable excipient.

14. The medicament of claim 13 for the treatment and/or prophylaxis of thromboembolic disorders.

15. A compound comprising
(A) (2-{[1S)-1-(3-chlorophenyl)-2-fluoroethyl]amino}-7-methoxy-1,3-benzoxazol-5-yl)[(2S,5S)-5-(2-hydroxyethyl)-2-methylmorpholin-4-yl]methanone of the formula below

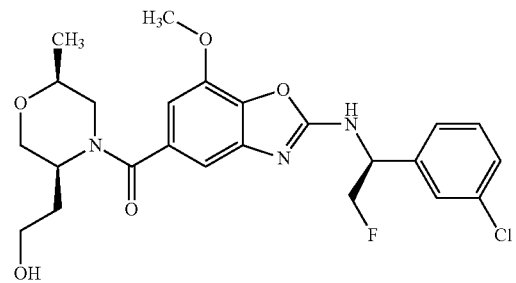 [SMILES: COc1cc(C(=O)N2C[C@H](C)OC[C@@H]2CCO)cc2nc(N[C@H](CF)c3cccc(Cl)c3)oc12]

or one of the salts thereof, solvates thereof or solvates of the salts thereof and
(B) 5-chloro-N-({(5S)-2-oxo-3 [4-(3-oxo-4-morpholinyl)phenyl]-1,3-oxazolidin-5-yl}methyl)-2-thiophenecarboxamide (rivaroxaban) having the structural formula

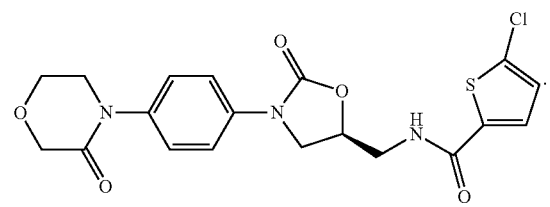 [SMILES: O=C(NC[C@H]1CN(c2ccc(N3CCOCC3=O)cc2)C(=O)O1)c1ccc(Cl)s1]

16. A medicament for the treatment and/or prophylaxis of deep leg venous thromboses and kidney venous thromboses comprising the compound of claim 1 in combination with an inert, nontoxic, pharmaceutically suitable excipient.

17. A medicament for the treatment and/or prophylaxis of acute coronary syndrome (ACS), venous thromboembolisms, venous thromboses, pulmonary embolisms, stroke and/or thrombosis prophylaxis in the context of surgical interventions in patients suffering from cancer comprising the compound of claim 1 in combination with an inert, nontoxic, pharmaceutically suitable excipient.

\* \* \* \* \*